US006168948B1

(12) United States Patent
Anderson et al.

(10) Patent No.: US 6,168,948 B1
(45) Date of Patent: Jan. 2, 2001

(54) MINIATURIZED GENETIC ANALYSIS SYSTEMS AND METHODS

(75) Inventors: Rolfe C. Anderson, Saratoga; Robert J. Lipshutz, Palo Alto; Richard P. Rava, Redwood City; Stephen P. A. Fodor, Palo Alto, all of CA (US)

(73) Assignee: Affymetrix, Inc., Santa Clara, CA (US)

( * ) Notice: Under 35 U.S.C. 154(b), the term of this patent shall be extended for 0 days.

(21) Appl. No.: 09/005,985

(22) Filed: Jan. 12, 1998

Related U.S. Application Data

(63) Continuation-in-part of application No. 08/992,025, filed on Dec. 17, 1997, now abandoned, and a continuation-in-part of application No. 08/589,027, filed on Jan. 19, 1996, now Pat. No. 5,856,174, and a continuation-in-part of application No. 08/671,928, filed on Jun. 27, 1996, now Pat. No. 5,922,591.

(60) Provisional application No. 60/000,703, filed on Jun. 29, 1995, provisional application No. 60/000,859, filed on Jul. 5, 1995, and provisional application No. 60/043,490, filed on Apr. 10, 1997.

(51) Int. Cl.[7] .................................................... C12M 1/34

(52) U.S. Cl. ....................... 435/287.2; 435/6; 435/287.9; 435/288.6

(58) Field of Search ............................... 435/6, 7.1, 7.92, 435/287.1, 287.2, 287.9, 288.6; 436/518, 523, 527, 528, 530, 89, 90, 94; 422/68.1, 100, 101, 102; 536/25.4, 75.41; 210/656, 198.2

(56) References Cited

U.S. PATENT DOCUMENTS

| | | | |
|---|---|---|---|
| 4,426,451 | 1/1984 | Columbus . | |
| 4,490,216 | 12/1984 | McConnell . | |
| 4,591,550 | 5/1986 | Hafeman et al. . | |
| 4,676,274 | 6/1987 | Brown . | |
| 4,704,353 | 11/1987 | Humphries et al. . | |
| 4,758,786 | 7/1988 | Hafeman . | |
| 4,789,628 | * 12/1988 | Nayak . | |
| 4,790,640 | * 12/1988 | Nason . | |
| 4,849,330 | 7/1989 | Humphries et al. . | |
| 4,883,579 | 11/1989 | Humphries et al. . | |
| 4,911,794 | 3/1990 | Parce et al. . | |
| 4,915,812 | 4/1990 | Parce et al. . | |
| 4,963,815 | 10/1990 | Hafeman . | |
| 5,126,022 | 6/1992 | Soane et al. . | |
| 5,143,854 | 9/1992 | Pirrung et al. . | |
| 5,164,319 | 11/1992 | Hafeman et al. . | |
| 5,171,132 | 12/1992 | Miyazaki et al. . | |
| 5,188,963 | 2/1993 | Stapleton . | |
| 5,229,297 | * 7/1993 | Schnipelsky et al. | 436/94 |
| 5,230,866 | 7/1993 | Shartle et al. . | |
| 5,252,294 | 10/1993 | Kroy et al. . | |
| 5,271,724 | 12/1993 | van Lintel . | |

(List continued on next page.)

FOREIGN PATENT DOCUMENTS

| | | |
|---|---|---|
| WO 90/04645 | 5/1990 | (WO) . |
| WO 90/15070 | 12/1990 | (WO) . |
| WO 92/10092 | 6/1992 | (WO) . |
| WO 93/09668 | 5/1993 | (WO) . |
| WO 94/03791 | 2/1994 | (WO) . |
| WO 94/05414 | 3/1994 | (WO) . |
| WO 98/52691 | 11/1998 | (WO) . |

OTHER PUBLICATIONS

Anderson et al., "Miniaturized genetic–analysis system," *Technical Digest of 1996 Solid–State Sensor and Actuator Workshop*, Hilton Head Island, South Carolina, pp. 258–261 (1996).

(List continued on next page.)

*Primary Examiner*—William H. Beisner
(74) *Attorney, Agent, or Firm*—Townsend and Townsend and Crew LLP

(57) ABSTRACT

The present invention provides a miniaturized integrated nucleic acid diagnostic device and system which includes a nucleic acid extraction zone including nucleic acid binding sites.

6 Claims, 62 Drawing Sheets

U.S. PATENT DOCUMENTS

| | | | | |
|---|---|---|---|---|
| 5,277,556 | | 1/1994 | van Lintel . | |
| 5,281,516 | | 1/1994 | Stapleton et al. . | |
| 5,296,375 | | 3/1994 | Kricka et al. . | |
| 5,304,487 | | 4/1994 | Wilding et al. . | |
| 5,346,672 | | 9/1994 | Stapleton et al. . | |
| 5,375,979 | | 12/1994 | Trah . | |
| 5,382,511 | | 1/1995 | Stapleton . | |
| 5,384,261 | | 1/1995 | Winkler et al. . | |
| 5,395,503 | | 3/1995 | Parce et al. . | |
| 5,424,186 | | 6/1995 | Fodor et al. . | |
| 5,436,129 | | 7/1995 | Stapleton . | |
| 5,451,500 | | 9/1995 | Stapleton . | |
| 5,486,335 | | 1/1996 | Wilding et al. . | |
| 5,498,392 | | 3/1996 | Wilding et al. . | |
| 5,500,188 | | 3/1996 | Hafeman et al. . | |
| 5,580,523 | * | 12/1996 | Bard | 422/50 |
| 5,587,128 | | 12/1996 | Wilding et al. . | |
| 5,589,350 | | 12/1996 | Bochner . | |
| 5,653,939 | | 8/1997 | Hollis et al. . | |
| 5,660,993 | | 8/1997 | Cathey et al. . | |
| 5,726,026 | * | 3/1998 | Wilding et al. | 435/7.21 |
| 5,843,767 | * | 12/1998 | Beattie | 435/287.1 |
| 5,858,195 | | 1/1999 | Ramsey . | |
| 5,863,801 | * | 1/1999 | Southgate | 436/63 |
| 5,876,918 | * | 3/1999 | Wainwright et al. | 435/287.9 |
| 5,952,173 | * | 9/1999 | Hansmann et al. . | |
| 5,976,336 | | 11/1999 | Dubrow et al. . | |
| 6,001,229 | | 12/1999 | Ramsey . | |
| 6,001,231 | | 12/1999 | Kopf-Sill . | |
| 6,010,607 | | 1/2000 | Ramsey . | |
| 6,010,608 | | 1/2000 | Ramsey . | |
| 6,033,546 | | 3/2000 | Ramsey . | |

OTHER PUBLICATIONS

Anderson et al., "Microfluidic biochemical analysis system," *Technical Digest of Transducers '97, International Conference on Solid–State Sensors and Actuators*. Chicago, p. 477–480 (1997).

Anderson et al., "Microfluidic Genetic Analysis Systems: Improvements and Methods," *Solid–State Sensor and Actuator Workshop*, (Jun. 7–11, 1998) 4 pages total.

Anderson et al., "Microfluidic Genetic Analysis Systems: Improvements and Methods," *Abstract for 1998 Solid–State Sensor and Actuator Workshop*, (Jun. 7–11, 1998) 4 pages total.

Andersson et al., *Technical Digest of Transducers '97, International Conference on Solid–State Sensors and Actuators*, Chicago, p. 1311–1314 (1997).

Bart et al., "Microfabricated Electrohydrodynamic Pumps," *Sensors and Actuators*, A21–A23:193–197 (1990).

Bousse et al., "Biosensors for Detection of Enzymes Immobilized in Microvolume Reaction Chambers," *Sensors and Actuators*, B1:555–560 (1990).

Effenhauser et al., "Glass Chips for High–Speed Capillary Electrophoresis Separations with Submicrometer Plate Heights," *Anal. Chem.*, 65:2637–2642 (1993).

Effenhauser et al., "High–Speed Separation of Antisense Oligonucelotides on a Micromachined Capillary Electrophoresis Device," *Anal. Chem.*, 66:2949–2953 (1994).

Fodor et al., "Light–Directed, Spatially Addressable Parallel Chemical Synthesis," *Science*, 251:767–777 (1991).

Ghandi, "Lithographic processes," *VLSI Fabrication Principles*, 2nd ed., John Wiley & Sons, Inc., Ch. 10, pp. 662–703 (1994).

Harrison et al., "Micromachining a Miniaturized Capillary Electrophoresis–Based Chemical Analysis System on a Chip," *Science*, 261:895–897 (1993).

Harrison et al., "Immunoassay Systems on Chip," *Technical Digest of 1996 Solid–State Sensor and Actuator Workshop*, Hilton Head Island, South Carolina, p. 5 (1996).

Horowitz and Hill, "Measurements and signal processing," *The Art of Electronics*, 2nd ed., Cambridge University Press, Ch. 15, pp. 987–1041 (1994).

Jacobsen et al., "High–Speed Separations on a Microchip," *Anal. Chem.*, 66:1114–1118 (1994).

Li et al., "Transport, manipulation, and reaction of biological cells on–chip using electrokinetic effects," *Anal. Chem.*, 69(8) :1564–1568 (1997).

Luckey et al., "A model for the mobility of single–stranded DNA in capillary gel electrophoresis," *Electroophoresis*, 14:492–501 (1993).

Man et al., "Microfluidic Plastic Capillaries on Silicon Substrates: A New Inexpensive Technology for Bioanalysis Chips," *Proceedings IEEE Tenth Annual International Workshop on Mechanical Systems*, Nagoya, Japan, (Jan. 26–30, 1997) pp. 311–316.

Manz et al., "Planar chips technology for miniaturization and integration of separation techniques into monitoring systems: Capillary electrophoresis on a chip," *J. Chromatog.*, 593:253–258 (1992).

Nyborg, "Acoustical streaming," *Physical Acoustics, Principles and Methods*, vol. 2, Part B, Mason, ed., Academic Press, Chapt. 11, pp. 265–333, (1965).

Owicki et al., "The Light–Addressable Potentiometric Sensor: Principles and Biological Applications," *Annu. Rev. Biophys. Biomol. Struct.* 23:87–113 (1994).

Pease et al., "Light–generated oligonucleotide arrays for rapid DNA sequence analysis," *PNAS*, 91:5022–5026 (1994).

*Piezoelectric Technology, Data for Engineers*, Clevite Corp., pp. 1–44. No Date Provided.

Richter et al., "An Electrohydrodynamic Micropump," *Third IEEE Workshop on Micro Electro Mechanical Systems*, Napa Valley (Feb. 12–14, 1990) pp. 99–104.

Richter et al., "A micromachined electrohydrodynamic (EHD) pump," *Sensors and Actuators*, 29:159–165 (1991).

Wooley and Mathies, "Ultra high–speed DNA fragment separations using microfabricated capillary array electrophoresis chips," *PNAS*, 91:11348–11352 (1994).

Wooley et al., "Functional integration of PCR amplification and capillary electrophoresis in a microfabricated DNA analysis device," *Anal. Chem.*, 68(23):4081–4086 (1996).

* cited by examiner

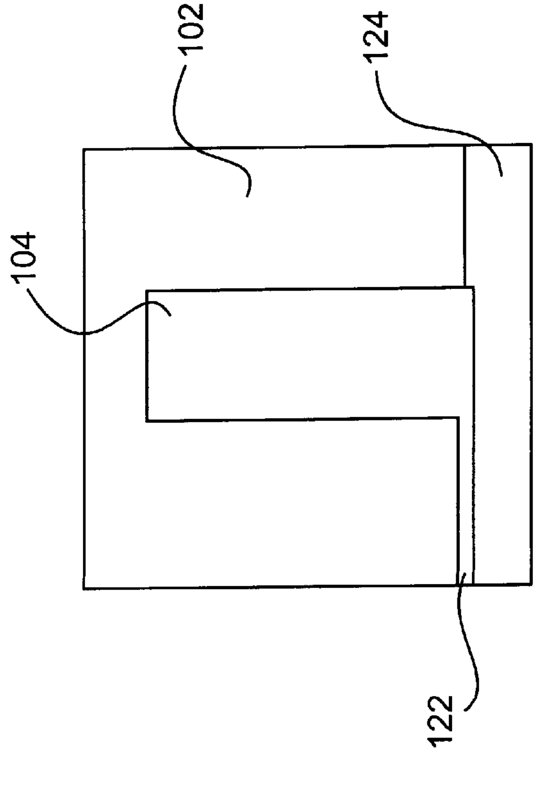
FIG. 2a
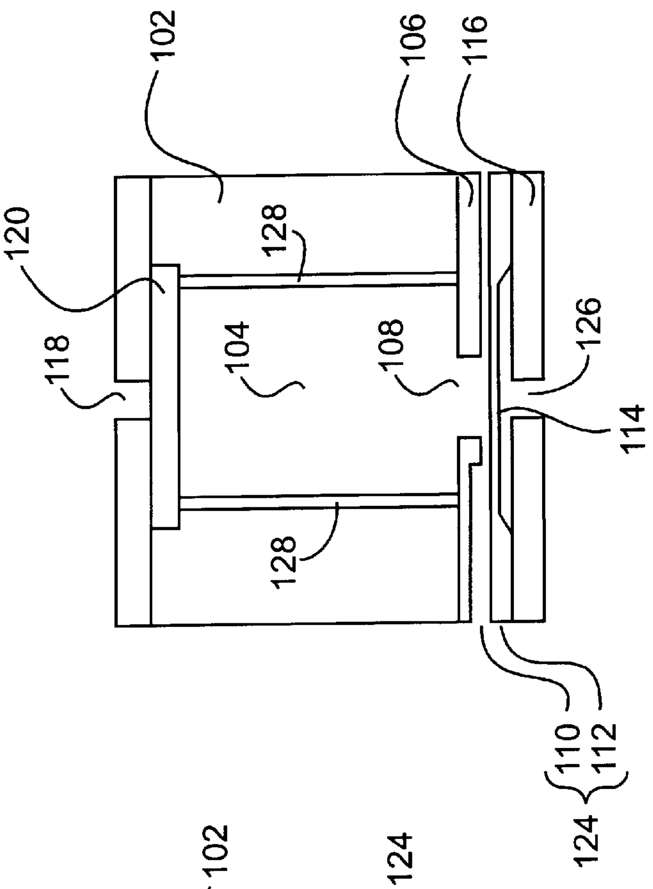
FIG. 2b
FIG. 2a & 2b

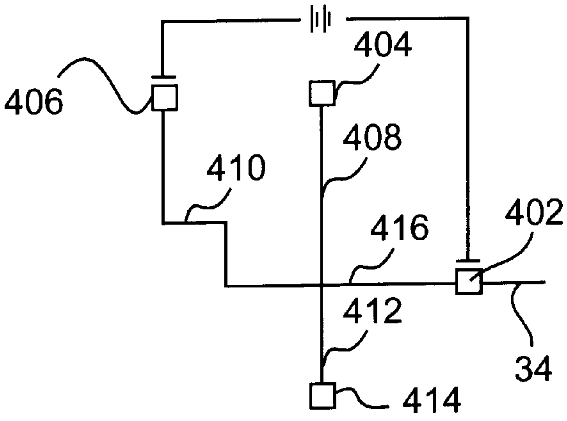
FIG. 4a
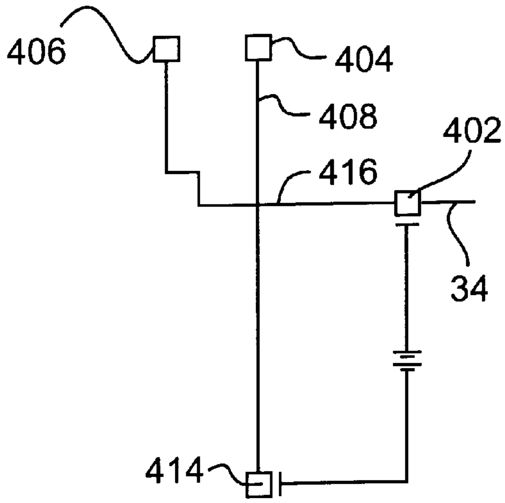
FIG. 4b
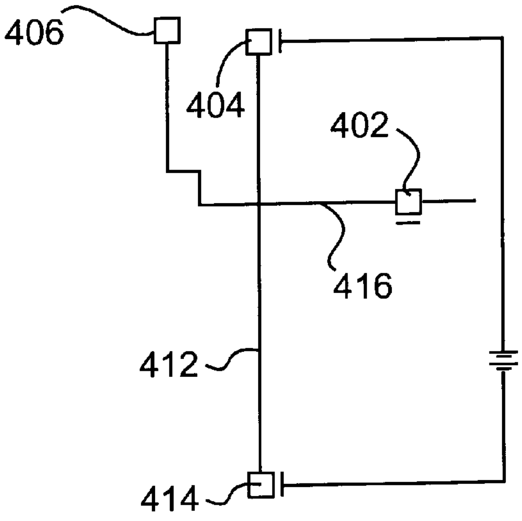
FIG. 4c
FIG. 4a-4c

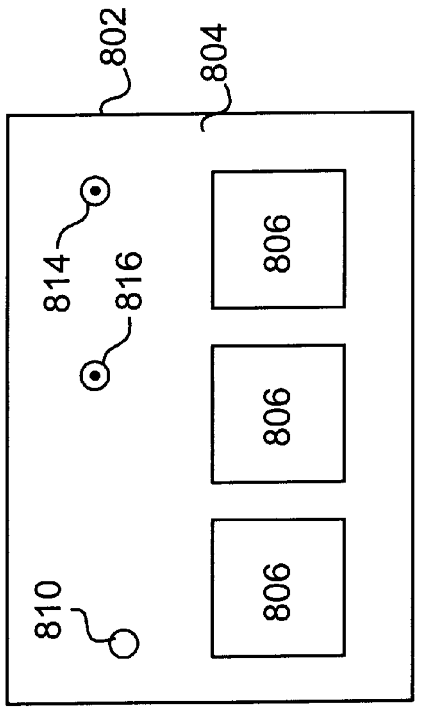
FIG. 8b
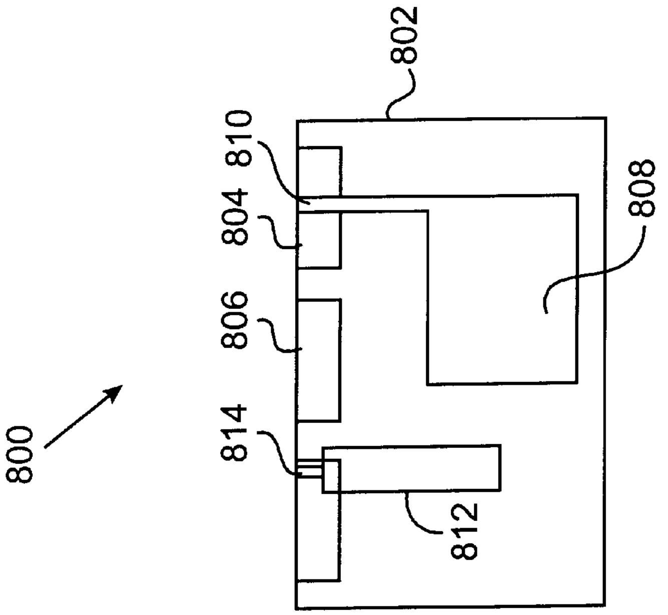
FIG. 8a
FIG. 8a & 8b t = 0 5 10 30 60 120 minutes

Correct Call Rates:

74% 95.8% 95.9%

95.9% 95.5% 83%

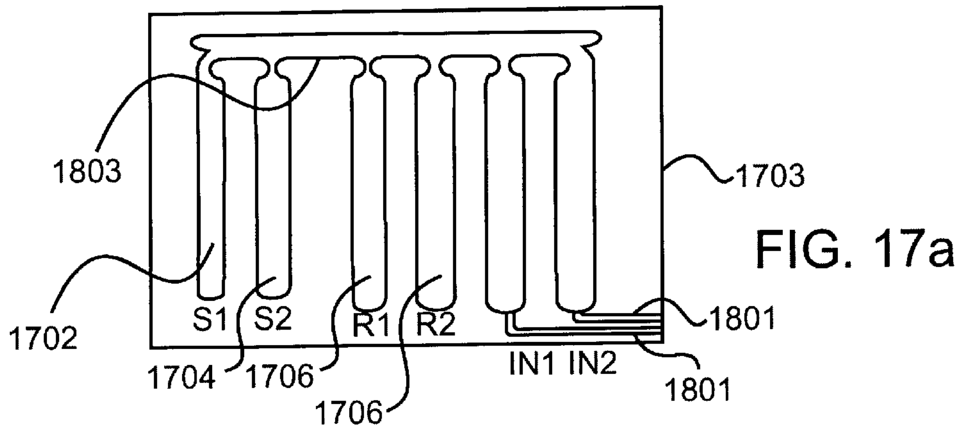
FIG. 17a
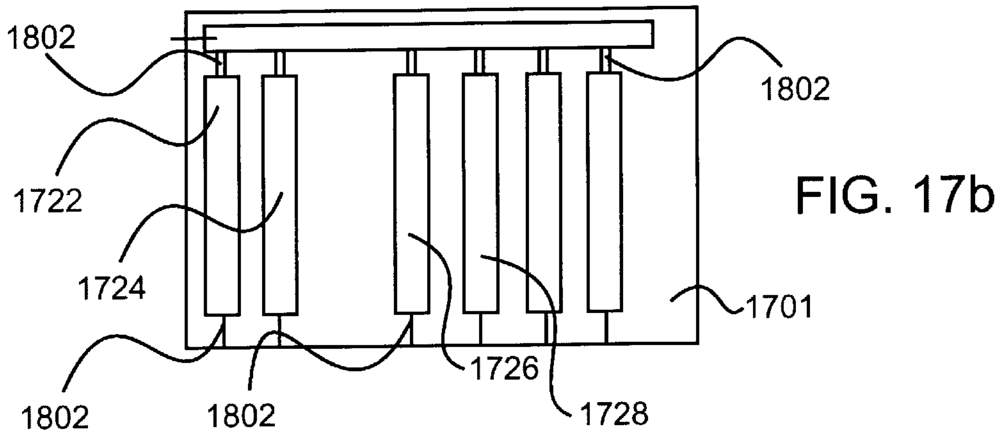
FIG. 17b
FIG. 17
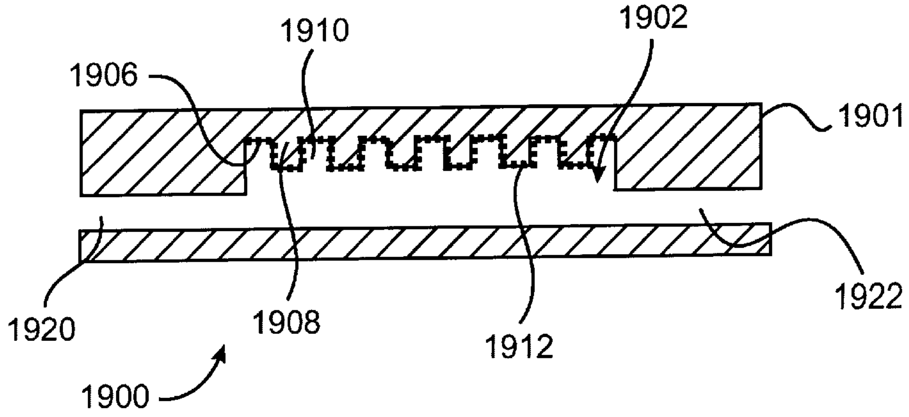
FIG. 18

MINIATURIZED GENETIC ANALYSIS SYSTEMS AND METHODS

CROSS REFERENCE TO RELATED APPLICATIONS

This application claims the benefit of U.S. Provisional Application No. 60/043,490, filed Apr. 10, 1997. This application is a continuation-in-part of U.S. application Ser. No. 08/992,025, filed Dec. 17, 1997, now abandoned; and is a continuation-in-part of U.S. application Ser. No. 08/589,027, filed Jan. 19, 1996, now U.S. Pat. No. 5,856,174; and is a continuation-in-part of U.S. application Ser. No. 08/671,928, filed Jun. 27, 1996, now U.S. Pat. No. 5,922,591, which claims the benefit of U.S. Provisional Application No. 60/000,703, filed Jun. 29, 1995, and U.S. Provisional Application No. 60/000,859, filed Jul. 5, 1995. Each of these applications is incorporated herein by reference in its entirety for all purposes.

GOVERNMENT RIGHTS

Portions of the present invention were made with U.S. Government support under ATP Grant No. 70NANB5H1031. The government may have certain rights in this invention.

BACKGROUND OF THE INVENTION

The relationship between structure and function of macromolecules is of fundamental importance in the understanding of biological systems. These relationships are important to understanding, for example, the functions of enzymes, structure of signaling proteins, ways in which cells communicate with each other, as well as mechanisms of cellular control and metabolic feedback.

Genetic information is critical in continuation of life processes. Life is substantially informationally based and its genetic content controls the growth and reproduction of the organism. The amino acid sequences of polypeptides, which are critical features of all living systems, are encoded by the genetic material of the cell. Further, the properties of these polypeptides, e.g., as enzymes, functional proteins, and structural proteins, are determined by the sequence of amino acids which make them up. As structure and function are integrally related, many biological functions may be explained by elucidating the underlying structural features which provide those functions, and these structures are determined by the underlying genetic information in the form of polynucleotide sequences. In addition to encoding polypeptides, polynucleotide sequences can also be specifically involved in, for example, the control and regulation of gene expression.

The study of this genetic information has proved to be of great value in providing a better understanding of life processes, as well as diagnosing and treating a large number of disorders. In particular, disorders which are caused by mutations, deletions or repeats in specific portions of the genome, may be readily diagnosed and/or treated using genetic techniques. Similarly, disorders caused by external agents may be diagnosed by detecting the presence of genetic material which is unique to the external agent, e.g., bacterial or viral DNA.

While current genetic methods are generally capable of identifying these genetic sequences, such methods generally rely on a multiplicity of distinct processes to elucidate the nucleic acid sequences, with each process introducing a potential for error into the overall process. These processes also draw from a large number of distinct disciplines, including chemistry, molecular biology, medicine and others. It would therefore be desirable to integrate the various process used in genetic diagnosis, in a single process, at a minimum cost, and with a maximum ease of operation.

Interest has been growing in the fabrication of microfluidic devices. Typically, advances in the semiconductor manufacturing arts have been translated to the fabrication of micromechanical structures, e.g., micropumps, microvalves, and the like, and microfluidic devices including miniature chambers and flow passages.

A number of researchers have attempted to employ these microfabrication techniques in the miniaturization of some of the processes involved in genetic analysis in particular. For example, published PCT Application No. WO 94/05414, to Northrup and White, incorporated herein by reference in its entirety for all purposes, reports an integrated micro-PCR apparatus for collection and amplification of nucleic acids from a specimen. However, there remains a need for an apparatus which combines the various processing and analytical operations involved in nucleic acid analysis. The present invention meets these and other needs.

SUMMARY OF THE INVENTION

The present invention generally provides miniature integrated fluidic systems for carrying out a variety of preparative and analytical operations, as well as methods of operating these systems and methods of using these systems.

BRIEF DESCRIPTION OF THE DRAWINGS

FIGS. 2A and 2B show schematic representations of two alternate reaction chamber designs from a cut-away view.

FIGS. 4A–C show a representation of a microcapillary electrophoresis device. FIGS. 4A and 4B show the microcapillary configured for carrying out alternate loading strategies for the microcapillary whereas FIG. 4C illustrates the microcapillary in running mode.

FIG. 6 shows schematic illustrations of pneumatic control manifolds for transporting fluid within a miniature integrated device. FIG. 6A shows a manifold configuration suitable for application of negative pressure, or vacuum, whereas

FIGS. 8A and 8B are schematic illustrations of a side and top view of a base-unit for use with a miniature integrated device.

FIG. 11A shows an embodiment of a single chamber employing this system. FIG. 11B is a schematic illustration of a debubbling chamber for linking discrete fluid plugs that are separated by a gas bubble. FIG. 11C schematically illustrates this system in an integrated device having numerous chambers, including degassing chamber, dosing or volumetric chamber, storage and reaction chambers.

FIG. 14 shows a demonstration of integrated reactions in a microfabricated polycarbonate device.

FIG. 17A is a top plan view of the pneumatic portion of the reactor device of FIG. 16.

FIG. 17B is a top plan view of the fluid portion of the reactor device of FIG. 16.

FIG. 18 schematically illustrates an affinity based nucleic acid extraction device incorporating a textured wall.

DETAILED DESCRIPTION OF THE INVENTION

I. General

Figure 1:
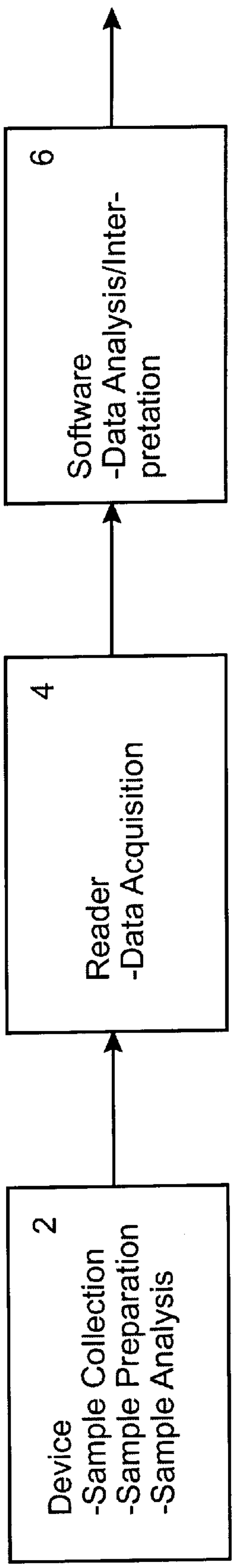
FIG. 1 shows a schematic representation of a nucleic acid diagnostic system for analysis of nucleic acids from samples.

It is a general object of the present invention to provide a miniaturized integrated nucleic acid diagnostic devices and systems incorporating these devices. The devices of the invention are generally capable of performing one or more sample acquisition and preparation operations, as may be integrated with one or more sample analysis operations. For example, the devices can integrate several or all of the operations involved in sample acquisition and storage, sample preparation and sample analysis, within a single, miniaturized, integrated unit. The devices are useful in a variety of applications and most notably, nucleic acid based diagnostic applications and de novo sequencing applications.

The devices of the invention will typically be one component of a larger diagnostic system which further includes reader device for scanning and obtaining the data from the device, and a computer based interface for controlling the device and/or interpretation of the data derived from the device.

To carry out their primary functions, one embodiment of the devices of the invention will typically incorporate a plurality of distinct reaction chambers for carrying out the sample acquisition, preparation and analysis operations. In particular, a sample to be analyzed is introduced into the device whereupon it will be delivered to one of these distinct reaction chambers which are designed for carrying out a variety of reactions as a prelude to analysis of the sample. These preparative reactions generally include, e.g., sample extraction, PCR amplification, nucleic acid fragmentation and labeling, extension reactions, transcription reactions and the like.

Following sample preparation, the sample can be subjected to one or more different analysis operations. A variety of analysis operations may generally be performed, including size based analysis using, e.g., microcapillary electrophoresis, and/or sequence based analysis using, e.g., hybridization to an oligonucleotide array. In addition to the various reaction chambers, the device will generally comprise a series of fluid channels which allow for the transportation of the sample or a portion thereof, among the various reaction chambers. Further chambers and components may also be included to provide reagents, buffers, sample manipulation, e.g., mixing, pumping, fluid direction (i.e., valves) heating and the like.

II. Integratable Operations

A. Sample Acquisition

The sample collection portion of the device of the present invention generally provides for the identification of the sample, while preventing contamination of the sample by external elements, or contamination of the environment by the sample. Generally, this is carried out by introducing a sample for analysis, e.g., preamplified sample, tissue, blood, saliva, etc., directly into a sample collection chamber within the device. Typically, the prevention of cross-contamination of the sample may be accomplished by directly injecting the sample into the sample collection chamber through a sealable opening, e.g., an injection valve, or a septum. Generally, sealable valves are preferred to reduce any potential threat of leakage during or after sample injection. Alternatively, the device may be provided with a hypodermic needle integrated within the device and connected to the sample collection chamber, for direct acquisition of the sample into the sample chamber. This can substantially reduce the opportunity for contamination of the sample.

In addition to the foregoing, the sample collection portion of the device may also include reagents and/or treatments for neutralization of infectious agents, stabilization of the specimen or sample, pH adjustments, and the like. Stabilization and pH adjustment treatments may include, e.g., introduction of heparin to prevent clotting of blood samples, addition of buffering agents, addition of protease or nuclease inhibitors, preservatives and the like. Such reagents may generally be stored within the sample collection chamber of the device or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

B. Sample Preparation

In between introducing the sample to be analyzed into the device, and analyzing that sample, e.g., on an oligonucleotide array, it will often be desirable to perform one or more sample preparation operations upon the sample. Typically, these sample preparation operations will include such manipulations as extraction of intracellular material, e.g., nucleic acids from whole cell samples, viruses and the like, amplification of nucleic acids, fragmentation, transcription, labeling and/or extension reactions. One or more of these various operations may be readily incorporated into the device of the present invention.

C. NA Extraction

For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like.

Liberation of nucleic acids from the sample cells or viruses, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within the extraction chamber, a separate accessible chamber or externally introduced.

Alternatively, physical methods may be used to extract the nucleic acids and denature DNA binding proteins. U.S. Pat.

No. 5,304,487, incorporated herein by reference in its entirety for all purposes, discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g., employing a channel with restricted cross-sectional dimension which causes cell lysis when the sample is passed through the channel with sufficient flow pressure.

Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to effect cell lysis/extraction, including, e.g., subjecting cells to ultrasonic agitation, or forcing cells through microgeometry apertures, thereby subjecting the cells to high shear stress resulting in rupture.

Following extraction, it will often be desirable to separate the nucleic acids from other elements of the crude extract, e.g., denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the devices of the present invention, and is commercially available from, e.g., Pharmacia and Sigma Chemical.

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g., charged groups, affinity binding groups and the like, i.e., poly-T oligonucleotides for mRNA purification.

Alternatively, desalting methods may generally take advantage of the high electrophoretic mobility and negative charge of DNA compared to other elements. Electrophoretic methods may also be utilized in the purification of nucleic acids from other cell contaminants and debris. In one example, a separation channel or chamber of the device is fluidly connected to two separate "field" channels or chambers having electrodes, e.g., platinum electrodes, disposed therein. The two field channels are separated from the separation channel using an appropriate barrier or "capture membrane" which allows for passage of current without allowing passage of nucleic acids or other large molecules. The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g., acting as a salt junction). Such barriers may include, e.g., dialysis membranes, dense gels, PEI filters, or other suitable materials. Upon application of an appropriate electric field, the nucleic acids present in the sample will migrate toward the positive electrode and become trapped on the capture membrane. Sample impurities remaining free of the membrane are then washed from the chamber by applying an appropriate fluid flow. Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use.

In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

For a number of applications, it may be desirable to extract and separate messenger RNA from cells, cellular debris, and other contaminants. As such, the device of the present invention may, in some cases, include an mRNA purification chamber or channel. In general, such purification takes advantage of the poly-A tails on mRNA. In particular and as noted above, poly-T oligonucleotides may be immobilized within a chamber or channel of the device to serve as affinity ligands for mRNA. Poly-T oligonucleotides may be immobilized upon a solid support incorporated within the chamber or channel, or alternatively, may be immobilized upon the surface(s) of the chamber or channel itself. Immobilization of oligonucleotides on the surface of the chambers or channels may be carried out by methods described herein including, e.g., oxidation and silanation of the surface followed by standard DMT synthesis of the oligonucleotides.

In operation, the lysed sample is introduced into this chamber or channel in an appropriate salt solution for hybridization, whereupon the mRNA will hybridize to the immobilized poly-T. Hybridization may also be enhanced through incorporation of mixing elements, also as described herein. After enough time has elapsed for hybridization, the chamber or channel is washed with clean salt solution. The mRNA bound to the immobilized poly-T oligonucleotides is then washed free in a low ionic strength buffer. The surface area upon which the poly-T oligonucleotides are immobilized may be increased through the use of etched structures within the chamber or channel, e.g., ridges, grooves or the like. Such structures also aid in the agitation of the contents of the chamber or channel, as described herein. Alternatively, the poly-T oligonucleotides may be immobilized upon porous surfaces, e.g., porous silicon, zeolites, silica xerogels, cellulose, sintered particles, or other solid supports.

D. Amplification and In Vitro Transcription

Following sample collection and nucleic acid extraction, the nucleic acid portion of the sample is typically subjected to one or more preparative reactions. These preparative reactions include in vitro transcription, labeling, fragmentation, amplification and other reactions. Nucleic acid amplification increases the number of copies of the target nucleic acid sequence of interest. A variety of amplification methods are suitable for use in the methods and device of the present invention, including for example, the polymerase chain reaction method or (PCR), the ligase chain reaction (LCR), self sustained sequence replication (3SR), and nucleic acid based sequence amplification (NASBA).

The latter two amplification methods involve isothermal reactions based on isothermal transcription, which produce both single stranded RNA (ssRNA) and double stranded DNA (dsDNA) as the amplification products in a ratio of approximately 30 or 100 to 1, respectively. As a result, where these latter methods are employed, sequence analysis may be carried out using either type of substrate, i.e., complementary to either DNA or RNA.

In particularly preferred aspects, the amplification step is carried out using PCR techniques that are well known in the art. See *PCR Protocols: A Guide to Methods and Applications* (Innis, M., Gelfand, D., Sninsky, J. and White, T., eds.) Academic Press (1990), incorporated herein by reference in its entirety for all purposes. PCR amplification generally involves the use of one strand of the target nucleic acid sequence as a template for producing a large number of complements to that sequence. Generally, two primer sequences complementary to different ends of a segment of the complementary strands of the target sequence hybridize with their respective strands of the target sequence, and in the presence of polymerase enzymes and deoxy-nucleoside triphosphates, the primers are extended along the target sequence. The extensions are melted from the target sequence and the process is repeated, this time with the additional copies of the target sequence synthesized in the preceding steps. PCR amplification typically involves repeated cycles of denaturation, hybridization and extension reactions to produce sufficient amounts of the target nucleic acid. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In PCR methods, strand separation is normally achieved by heating the reaction to a sufficiently high temperature for a sufficient time to cause the denaturation of the duplex but not to cause an irreversible denaturation of the polymerase enzyme (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology,* 43:63–67; and Radding, 1982, *Ann. Rev. Genetics* 16:405–436, each of which is incorporated herein by reference). Other embodiments may achieve strand separation by application of electric fields across the sample. For example, Published PCT Application Nos. WO 92/04470 and WO 95/25177, incorporated herein by reference, describe electrochemical methods of denaturing double stranded DNA by application of an electric field to a sample containing the DNA. Structures for carrying out this electrochemical denaturation include a working electrode, counter electrode and reference electrode arranged in a potentiostat arrangement across a reaction chamber (See, Published PCT Application Nos. WO 92/04470 and WO 95/25177, each of which is incorporated herein by reference for all purposes). Such devices may be readily miniaturized for incorporation into the devices of the present invention utilizing the microfabrication techniques described herein.

Template-dependent extension of primers in PCR is catalyzed by a polymerizing agent in the presence of adequate amounts of at least 4 deoxyribonucleotide triphosphates (typically selected from DATP, dGTP, dCTP, dUTP and dTTP) in a reaction medium which comprises the appropriate salts, metal cations, and pH buffering system. Reaction components and conditions are well known in the art (See *PCR Protocols: A Guide to Methods and Applications* (Innis, M., Gelfand, D., Sninsky, J. and White, T., eds.) Academic Press (1990), previously incorporated by reference). Suitable polymerizing agents are enzymes known to catalyze template-dependent DNA synthesis.

Published PCT Application No. WO 94/05414, to Northrup and White, discusses the use of a microPCR chamber which incorporates microheaters and micropumps in the thermal cycling and mixing during the PCR reactions.

The amplification reaction chamber of the device may comprise a sealable opening for the addition of the various amplification reagents. However, in preferred aspects, the amplification chamber will have an effective amount of the various amplification reagents described above, predisposed within the amplification chamber, or within an associated reagent chamber whereby the reagents can be readily transported to the amplification chamber upon initiation of the amplification operation. By "effective amount" is meant a quantity and/or concentration of reagents required to carry out amplification of a targeted nucleic acid sequence. These amounts are readily determined from known PCR protocols. See, e.g., Sambrook, et al. *Molecular Cloning: A Laboratory Manual,* (2nd ed.) Vols. 1–3, Cold Spring Harbor Laboratory, (1989) and *PCR Protocols: A Guide to Methods and Applications* (Innis, M., Gelfand, D., Sninsky, J. and White, T., eds.) Academic Press (1990), both of which are incorporated herein by reference for all purposes in their entirety. For those embodiments where the various reagents are predisposed within the amplification or adjacent chamber, it will often be desirable for these reagents to be in lyophilized forms, to provide maximum shelf life of the overall device. Introduction of the liquid sample to the chamber then reconstitutes the reagents in active form, and the particular reactions may be carried out.

In some aspects, the polymerase enzyme may be present within the amplification chamber, coupled to a suitable solid support, or to the walls and surfaces of the amplification chamber. Suitable solid supports include those that are well known in the art, e.g., agarose, cellulose, silica, divinylbenzene, polystyrene, etc. Coupling of enzymes to solid supports has been reported to impart stability to the enzyme in question, which allows for storage of days, weeks or even months without a substantial loss in enzyme activity, and without the necessity of lyophilizing the enzyme. The 94 kd, single subunit DNA polymerase from Thermus aquaticus (or taq polymerase) is particularly suited for the PCR based amplification methods used in the present invention, and is generally commercially available from, e.g., Promega, Inc., Madison, Wis. In particular, monoclonal antibodies are available which bind the enzyme without affecting its polymerase activity. Consequently, covalent attachment of the active polymerase enzyme to a solid support, or the walls of the amplification chamber can be carried out by using the antibody as a linker between the enzyme and the support.

In addition to PCR and IVT reactions, the methods and devices of the present invention are also applicable to a number of other reaction types, e.g., reverse transcription, nick translation, cDNAse generation, and the like.

In one embodiment, acoustic microstructures may be used for hybridization mixing. A description of an acoustic mixer may be found in X. Zhu and E. S. Kim "Microfluidic Motion Generation With Loosely-Focused Acoustic Waves", 1997 Int'l. Conference on Solid-State Sensors and Actuators, Jun. 16–19, 1997, Chicago, Ill.

E. Labeling and Fragmentation

The nucleic acids in a sample will generally be labeled to facilitate detection in subsequent steps. Labeling may be carried out during the amplification, in vitro transcription or nick translation processes. In particular, amplification, in vitro transcription or nick translation may incorporate a label into the amplified or transcribed sequence, either through the use of labeled primers or the incorporation of labeled dNTPs or NTPs into the amplified sequence.

Labeling may also be carried out by attaching an appropriately labeled (e.g. FICT, or biotin), dNTP to the 3'-end of DNAase fragmented PCR product using terminal deoxytransferase (TdT).

In an alternative embodiment, Poly(A) polymerase will "tail" any RNA molecule with polyA and therefore be used for radiolabeling RNA. Used in conjunction with a biotin-, fluorophore-, gold particle-(or other detectable moiety)-ATP conjugate, poly (A) polymerase can be used for direct 3'-end labelling of RNA targets for detecting hybridization to DNA probe arrays. The nucleotide conjugate may carry the detectable moiety attached, through a linker (or not) to positions on either the nucleotide base or sugar. With regard to relative incorporation efficiency, the enzyme may exhibit a preference for one or more of these positions. The nucleotide may be a 2', 3'-dideoxynucleotide, in which case only a single label will be added to the 3'-end of the RNA. A preferred format is to tail the RNA with 5-Bromo-UTP, and then detect hybridization indirectly using a labeled anti-bromouridine. This would closely parallel a currently favored assay format used for expression monitoring applications using biotinylated RNA and phycoerythrin-streptavidin "staining".

Alternatively, the nucleic acids in the sample may be labeled following amplification. Post amplification labeling typically involves the covalent attachment of a particular detectable group upon the amplified sequences. Suitable labels or detectable groups include a variety of fluorescent or radioactive labeling groups well known in the art. These labels may also be coupled to the sequences using methods that are well known in the art. See, e.g., Sambrook, et al.

In addition, amplified sequences may be subjected to other post amplification treatments. For example, in some cases, it may be desirable to fragment the sequence prior to hybridization with an oligonucleotide array, in order to provide segments which are more readily accessible to the probes, which avoid looping and/or hybridization to multiple probes. Fragmentation of the nucleic acids may generally be carried out by physical, chemical or enzymatic methods that are known in the art. These additional treatments may be performed within the amplification chamber, or alternatively, may be carried out in a separate chamber. For example, physical fragmentation methods may involve moving the sample containing the nucleic acid over pits or spikes in the surface of a reaction chamber or fluid channel. The motion of the fluid sample, in combination with the surface irregularities produces a high shear rate, resulting in fragmentation of the nucleic acids. In one aspect, this may be accomplished in a miniature device by placing a piezoelectric element, e.g., a PZT ceramic element adjacent to a substrate layer that covers a reaction chamber or flow channel, either directly, or through a liquid layer, as described herein. The substrate layer has pits, spikes or apertures manufactured in the surface which are within the chamber or flow channel. By driving the PZT element in the thickness mode, a standing wave is set up within the chamber. Cavitation and/or streaming within the chamber results in substantial shear. Similar shear rates may be achieved by forcing the nucleic acid containing fluid sample through restricted size flow passages, e.g., apertures having a cross-sectional dimension in the micron or submicron scale, thereby producing a high shear rate and fragmenting the nucleic acid.

A number of sample preparation operations may be carried out by adjusting the pH of the sample, such as cell lysis, nucleic acid fragmentation, enzyme denaturation and the like. Similarly, pH control may also play a role in a wide variety of other reactions to be carried out in the device, i.e., for optimizing reaction conditions, neutralizing acid or base additions, denaturing exogenously introduced enzymes, quenching reactions, and the like. Such pH monitoring and control may be readily accomplished using well known methods. For example, pH may be monitored by incorporation of a pH sensor or indicator within a particular chamber. Control may then be carried out by titration of the chamber contents with an appropriate acid or base.

Fragmentation may also be carried out enzymatically using, for example, DNAase or RNAase or restriction enzymes.

F. Sample Analysis

Following the various sample preparation operations, the sample will generally be subjected to one or more analysis operations. Particularly preferred analysis operations include, e.g., sequence based analyses using an oligonucleotide array and/or size based analyses using, e.g., microcapillary array electrophoresis.

1. Oligonucleotide Probe Array

In one aspect, following sample preparation, the nucleic acid sample is probed using an array of oligonucleotide probes. Oligonucleotide arrays generally include a substrate having a large number of positionally distinct oligonucleotide probes attached to the substrate. These oligonucleotide arrays, also described as "Genechip™ arrays," have been generally described in the art, for example, U.S. Pat. No. 5,143,854 and PCT patent publication Nos. WO 90/15070 and 92/10092. These pioneering arrays may be produced using mechanical or light directed synthesis methods which incorporate a combination of photolithographic methods and solid phase oligonucleotide synthesis methods. See Fodor et al., *Science,* 251:767–777 (1991), Pirrung et al., U.S. Pat. No. 5,143,854 (see also PCT Application No. WO 90/15070) and Fodor et al., PCT Publication No. WO 92/10092, all incorporated herein by reference. These references disclose methods of forming vast arrays of peptides, oligonucleotides and other polymer sequences using, for example, light-directed synthesis techniques. Techniques for the synthesis of these arrays using mechanical synthesis strategies are described in, e.g., PCT Publication No. 93/09668 and U.S.

Pat. No. 5,384,261, each of which is incorporated herein by reference in its entirety for all purposes. Incorporation of these arrays in injection molded polymeric casings has been described in Published PCT Application No. 95/33846.

The basic strategy for light directed synthesis of oligonucleotide arrays is as follows. The surface of a solid support, modified with photosensitive protecting groups is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask, to expose additional hydroxyl groups for coupling. A second selected nucleotide (e.g., 5'-protected, 3'-O-phosphoramidite-activated deoxynucleoside) is presented to the surface. The selective deprotection and coupling cycles are repeated until the desired set of products is obtained. Since photolithography is used, the process can be readily miniaturized to generate high density arrays of oligonucleotide probes. Furthermore, the sequence of the oligonucleotides at each site is known. See, Pease, et al. Mechanical synthesis methods are similar to the light directed methods except involving mechanical direction of fluids for deprotection and addition in the synthesis steps.

Typically, the arrays used in the present invention will have a site density of greater than 100 different probes per $cm^2$. Preferably, the arrays will have a site density of greater than $500/cm^2$, more preferably greater than about $1000/cm^2$, and most preferably, greater than about $10,000/cm^2$. Preferably, the arrays will have more than 100 different probes on a single substrate, more preferably greater than about 1000 different probes still more preferably, greater than about 10,000 different probes and most preferably, greater than 100,000 different probes on a single substrate.

For some embodiments, oligonucleotide arrays may be prepared having all possible probes of a given length. Such arrays may be used in such areas as sequencing or sequence checking applications, which offer substantial benefits over traditional methods. The use of oligonucleotide arrays in such applications is described in, e.g., U.S. patent application Ser. No. 08/505,919, filed Jul. 24, 1995, now abandoned, and U.S. patent application Ser. No. 08/284,064, filed Aug. 2, 1994, now abandoned, each of which is incorporated herein by reference in its entirety for all purposes. These methods typically use a set of short oligonucleotide probes of defined sequence to search for complementary sequences on a longer target strand of DNA. The hybridization pattern of the target sequence on the array is used to reconstruct the target DNA sequence. Hybridization analysis of large numbers of probes can be used to sequence long stretches of DNA.

One strategy of de novo sequencing can be illustrated by the following example. A 12-mer target DNA sequence is probed on an array having a complete set of octanucleotide probes. Five of the 65,536 octamer probes will perfectly hybridize to the target sequence. The identity of the probes at each site is known. Thus, by determining the locations at which the target hybridizes on the array, or the hybridization pattern, one can determine the sequence of the target sequence. While these strategies have been proposed and utilized in some applications, there has been difficulty in demonstrating sequencing of larger nucleic acids using these same strategies. Accordingly, in preferred aspects, SBH methods utilizing the devices described herein use data from mismatched probes, as well as perfectly matching probes, to supply useful sequence data, as described in U.S. patent application Ser. No. 08/505,919, now abandoned, incorporated herein by reference.

While oligonucleotide probes may be prepared having every possible sequence of length n, it will often be desirable in practicing the present invention to provide an oligonucleotide array which is specific and complementary to a particular nucleic acid sequence. For example, in particularly preferred aspects, the oligonucleotide array will contain oligonucleotide probes which are complementary to specific target sequences, and individual or multiple mutations of these. Such arrays are particularly useful in the diagnosis of specific disorders which are characterized by the presence of a particular nucleic acid sequence. For example, the target sequence may be that of a particular exogenous disease causing agent, e.g., human immunodeficiency virus (see, U.S. application Ser. No. 08/284,064, now abandoned, previously incorporated herein by reference), or alternatively, the target sequence may be that portion of the human genome which is known to be mutated in instances of a particular disorder, i.e., sickle cell anemia (see, e.g., U.S. application Ser. No. 08/082,937, now abandoned, previously incorporated herein by reference) or cystic fibrosis.

In such an application, the array generally comprises at least four sets of oligonucleotide probes, usually from about 9 to about 21 nucleotides in length. A first probe set has a probe corresponding to each nucleotide in the target sequence. A probe is related to its corresponding nucleotide by being exactly complementary to a subsequence of the target sequence that includes the corresponding nucleotide. Thus, each probe has a position, designated an interrogation position, that is occupied by a complementary nucleotide to the corresponding nucleotide in the target sequence. The three additional probe sets each have a corresponding probe for each probe in the first probe set, but substituting the interrogation position with the three other nucleotides. Thus, for each nucleotide in the target sequence, there are four corresponding probes, one from each of the probe sets. The three corresponding probes in the three additional probe sets are identical to the corresponding probe from the first probe or a subsequence thereof that includes the interrogation position, except that the interrogation position is occupied by a different nucleotide in each of the four corresponding probes.

Some arrays have fifth, sixth, seventh and eighth probe sets. The probes in each set are selected by analogous principles to those for the probes in the first four probe sets, except that the probes in the fifth, sixth, seventh and eighth sets exhibit complementarity to a second reference sequence. In some arrays, the first set of probes is complementary to the coding strand of the target sequence while the second set is complementary to the noncoding strand. Alternatively, the second reference sequence can be a subsequence of the first reference sequence having a substitution of at least one nucleotide.

In some applications, the target sequence has a substituted nucleotide relative to the probe sequence in at least one undetermined position, and the relative specific binding of the probes indicates the location of the position and the nucleotide occupying the position in the target sequence.

Following amplification and/or labeling, the nucleic acid sample is incubated with the oligonucleotide array in the hybridization chamber. Hybridization between the sample nucleic acid and the oligonucleotide probes upon the array is then detected, using, e.g., epifluorescence confocal microscopy. Typically, sample is mixed during hybridization to enhance hybridization of nucleic acids in the sample to nucleic acid probes on the array. Again, mixing may be carried out by the methods described herein, e.g., through the use of piezoelectric elements, electrophoretic methods, or physical mixing by pumping fluids into and out of the hybridization chamber, i.e., into an adjoining chamber. Generally, the detection operation will be performed using a reader device external to the diagnostic device. However, it may be desirable in some cases, to incorporate the data gathering operation into the diagnostic device itself. Novel systems for direct electronic detection of hybridization locations on the array will be set forth herein.

The hybridization data is next analyzed to determine the presence or absence of a particular sequence within the sample, or by analyzing multiple hybridizations to determine the sequence of the target nucleic acid using the SBH techniques already described.

In some cases, hybridized oligonucleotides may be labeled following hybridization. For example, where biotin labeled dNTPs are used in, e.g., amplification or transcription, streptavidin linked reporter groups may be used to label hybridized complexes. Such operations are readily integratable into the systems of the present invention, requiring the use of various mixing methods as is necessary.

2. Capillary Electrophoresis

In some embodiments, it may be desirable to provide an additional, or alternative means for analyzing the nucleic acids from the sample. In one embodiment, the device of the invention will optionally or additionally comprise a micro capillary array for analysis of the nucleic acids obtained from the sample.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, e.g., Woolley and Mathies, *Proc. Nat'l Acad. Sci. USA* (1994) 91:11348–11352. Microcapillary array electrophoresis generally provides a rapid method for size based sequencing, PCR product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods.

Microfabrication of microfluidic devices including microcapillary electrophoretic devices has been discussed in detail in, e.g., Jacobsen, et al., *Anal. Chem.* (1994) 66:1114–1118, Effenhauser, et al., *Anal. Chem.* (1994) 66:2949–2953, Harrison, et al., *Science* (1993) 261:895–897, Effenhauser, et al. *Anal. Chem.* (1993) 65:2637–2642, and Manz, et al., *J. Chromatog.* (1992) 593:253–258. Typically, these methods comprise photolithographic etching of micron scale channels on a silica, silicon or other rigid substrate or chip, and can be readily adapted for use in the miniaturized devices of the present invention. In some embodiments, the capillary arrays may be fabricated from the same polymeric materials described for the fabrication of the body of the device, using the injection molding techniques described herein. In such cases, the capillary and other fluid channels may be molded into a first planar element. A second thin polymeric member having ports corresponding to the termini of the capillary channels disposed therethrough, is laminated or sonically welded onto the first to provide the top surface of these channels. Electrodes for electrophoretic control are disposed within these ports/wells for application of the electrical current to the capillary channels. Through use of a relatively this sheet as the covering member of the capillary channels, heat generated during electrophoresis can be rapidly dissipated. Additionally, the capillary channels may be coated with more thermally conductive material, e.g., glass or ceramic, to enhance heat dissipation.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Gel matrices may be introduced and polymerized within the capillary channel. However, in some cases, this may result in entrapment of bubbles within the channels which can interfere with sample separations. Accordingly, it is often desirable to place a preformed separation matrix within the capillary channel(s), prior to mating the planar elements of the capillary portion. Fixing the two parts, e.g., through sonic welding, permanently fixes the matrix within the channel. Polymerization outside of the channels helps to ensure that no bubbles are formed. Further, the pressure of the welding process helps to ensure a void-free system. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

In addition to its use in nucleic acid "fingerprinting" and other sized based analyses, the capillary arrays may also be used in sequencing applications. In particular, gel based sequencing techniques may be readily adapted for capillary array electrophoresis. For example, capillary electrophoresis may be combined with the Sanger dideoxy chain termination sequencing methods as discussed in Sambrook, et al. (See also Brenner, et al., *Proc. Nat'l Acad. Sci.* (1989) 86:8902–8906). In these methods, the sample nucleic acid is amplified in the presence of fluorescent dideoxynucleoside triphosphates in an extension reaction. The random incorporation of the dideoxynucleotides terminates transcription of the nucleic acid. This results in a range of transcription products differing from another member by a single base. Comparative size based separation then allows the sequence of the nucleic acid to be determined based upon the last dideoxy nucleotide to be incorporated.

G. Data Gathering and Analysis

Gathering data from the various analysis operations, e.g., oligonucleotide and/or microcapillary arrays, will typically be carried out using methods known in the art. For example, the arrays may be scanned using lasers to excite fluorescently labeled targets that have hybridized to regions of probe arrays, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection. Particularly preferred scanning devices are generally described in, e.g., U.S. Pat. Nos. 5,143,854 and 5,424,186.

Following the data gathering operation, the data will typically be reported to a data analysis operation. To facilitate the sample analysis operation, the data obtained by the reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like, as described in, e.g., U.S. patent application Ser. No. 08/327,525, filed Oct. 21, 1994, and incorporated herein by reference.

III. The Nucleic Acid Diagnostic System

A. Analytical System

A schematic of a representative analytical system based upon the device of the invention is shown in FIG. 1. The system includes the diagnostic device 2 which performs one or more of the operations of sample collection, preparation and/or analysis using, e.g., hybridization and/or size based separation. The diagnostic device is then placed in a reader device 4 to detect the hybridization and or separation information present on the device. The hybridization and/or separation data is then reported from the reader device to a computer 6 which is programmed with appropriate software for interpreting the data obtained by the reader device from the diagnostic device. Interpretation of the data from the diagnostic device may be used in a variety of ways, including nucleic acid sequencing which is directed toward a particular disease causing agent, such as viral or bacterial infections, e.g., AIDS, malaria, etc., or genetic disorders, e.g., sickle cell anemia, cystic fibrosis, Fragile X syndrome, Duchenne muscular dystrophy, gene expression and the like. Alternatively, the device can be employed in de novo sequencing applications to identify the nucleic acid sequence of a previously unknown sequence.

B. The Diagnostic Device

1. Generally

As described above, the device of the present invention is generally capable of carrying out a number of preparative and analytical reactions on a sample. To achieve this end, the device generally comprises a number of discrete reaction, storage and/or analytical chambers disposed within a single unit or body. While referred to herein as a "diagnostic device," those of skill in the art will appreciate that the device of the invention will have a variety of applications outside the scope of diagnostics, alone. Such applications include sequencing applications, sample identification and characterization applications (for, e.g., taxonomic studies, forensic applications, i.e., criminal investigations, and the like).

Typically, the body of the device defines the various reaction chambers and fluid passages in which the above described operations are carried out. Fabrication of the body, and thus the various chambers and channels disposed within the body may generally be carried out using one or a combination of a variety of well known manufacturing techniques and materials. Generally, the material from which the body is fabricated will be selected so as to provide maximum resistance to the full range of conditions to which the device will be exposed, e.g., extremes of temperature, salt, pH, application of electric fields and the like, and will also be selected for compatibility with other materials used in the device. Additional components may be later introduced, as necessary, into the body. Alternatively, the device may be formed from a plurality of distinct parts that are later assembled or mated. For example, separate and individual chambers and fluid passages may be assembled to provide the various chambers of the device.

As a miniaturized device, the body of the device will typically be approximately 1 to 20 cm in length by about 1 to 10 cm in width by about 0.1 to about 2 cm thick. Although indicative of a rectangular shape, it will be readily appreciated that the devices of the invention may be embodied in any number of shapes depending upon the particular need. Additionally, these dimensions will typically vary depending upon the number of operations to be performed by the device, the complexity of these operations and the like. As a result, these dimensions are provided as a general indication of the size of the device. The number and size of the reaction chambers included within the device will also vary depending upon the specific application for which the device is to be used. Generally, the device will include at least two distinct reaction chambers, and preferably, at least three, four or five distinct reaction chambers, all integrated within a single body. Individual reaction chambers will also vary in size and shape according to the specific function of the reaction chamber. For example, in some cases, circular reaction chambers may be employed. Alternatively, elongate reaction chambers may be used. In general however, the reaction chambers will be from about 0.05 to about 20 mm in width or diameter, preferably from about 0.1 to about 2.0 mm in width or diameter and about 0.05 to about 5 mm deep, and preferably 0.05 to about 1 mm deep. For elongate chambers, length will also typically vary along these same ranges. Fluid channels, on the other hand, are typically distinguished from chambers in having smaller dimensions relative to the chambers, and will typically range from about 10 to about 1000 $\mu$m wide, preferably, 100 to 500 $\mu$m wide and about 1 to 500 $\mu$m deep. Although described in terms of reaction chambers, it will be appreciated that these chambers may perform a number of varied functions, e.g., as storage chambers, incubation chambers, mixing chambers and the like.

In some cases, a separate chamber or chambers may be used as volumetric chambers, e.g., to precisely measure fluid volumes for introduction into a subsequent reaction chamber. In such cases, the volume of the chamber will be dictated by volumetric needs of a given reaction. Further, the device may be fabricated to include a range of volumetric chambers having varied, but known volumes or volume ratios (e.g., in comparison to a reaction chamber or other volumetric chambers).

As described above, the body of the device is generally fabricated using one or more of a variety of methods and materials suitable for microfabrication techniques. For example, in preferred aspects, the body of the device may comprise a number of planar members that may individually be injection molded parts fabricated from a variety of polymeric materials, or may be silicon, glass, or the like. In the case of substrates like silica, glass or silicon, methods for etching, milling, drilling, etc., may be used to produce wells and depressions which make up the various reaction chambers and fluid channels within the device. Microfabrication techniques, such as those regularly used in the semiconductor and microelectronics industries are particularly suited to these materials and methods. These techniques include, e.g., electrodeposition, low-pressure vapor deposition, photolithography, wet chemical etching, reactive ion etching (RIE), laser drilling, and the like. Where these methods are used, it will generally be desirable to fabricate the planar members of the device from materials similar to those used in the semiconductor industry, i.e., silica, silicon, gallium arsenide, polyimide substrates. U.S. Pat. No. 5,252,294, to Kroy, et al., incorporated herein by reference in its entirety for all purposes, reports the fabrication of a silicon based multiwell apparatus for sample handling in biotechnology applications.

Photolithographic methods of etching substrates are particularly well suited for the microfabrication of these substrates and are well known in the art. For example, the first sheet of a substrate may be overlaid with a photoresist. An electromagnetic radiation source may then be shone through a photolithographic mask to expose the photoresist in a pattern which reflects the pattern of chambers and/or channels on the surface of the sheet. After removing the exposed photoresist, the exposed substrate may be etched to produce the desired wells and channels. Generally preferred photoresists include those used extensively in the semiconductor industry. Such materials include polymethyl methacrylate (PMMA) and its derivatives, and electron beam resists such as poly(olefin sulfones) and the like (more fully discussed in, e.g., Ghandi, "*VLSI Fabrication Principles,*" Wiley (1983) Chapter 10, incorporated herein by reference in its entirety for all purposes).

As an example, the wells manufactured into the surface of one planar member make up the various reaction chambers of the device. Channels manufactured into the surface of this or another planar member make up fluid channels which are used to fluidly connect the various reaction chambers. Another planar member is then placed over and bonded to the first, whereby the wells in the first planar member define cavities within the body of the device which cavities are the various reaction chambers of the device. Similarly, fluid channels manufactured in the surface of one planar member, when covered with a second planar member define fluid passages through the body of the device. These planar members are bonded together or laminated to produce a fluid tight body of the device.

Bonding of the planar members of the device may generally be carried out using a variety of methods known in the art and which may vary depending upon the materials used. For example, adhesives may generally be used to bond the planar members together. Where the planar members are, e.g., glass, silicon or combinations thereof, thermal bonding, anodic/electrostatic or silicon fusion bonding methods may be applied. For polymeric parts, a similar variety of methods may be employed in coupling substrate parts together, e.g., heat with pressure, solvent based bonding. Generally, acoustic welding techniques are generally preferred. In a related aspect, adhesive tapes may be employed as one portion of the device forming a thin wall of the reaction chamber/channel structures.

Although primarily described in terms of producing a fully integrated body of the device, the above described methods can also be used to fabricate individual discrete components of the device which are later assembled into the body of the device.

In additional embodiments, the body may comprise a combination of materials and manufacturing techniques described above. In some cases, the body may include some parts of injection molded plastics, and the like, while other portions of the body may comprise etched silica or silicon planar members, and the like. For example, injection molding techniques may be used to form a number of discrete cavities in a planar surface which define the various reaction chambers, whereas additional components, e.g., fluid channels, arrays, etc, may be fabricated on a planar glass, silica or silicon chip or substrate. Lamination of one set of parts to the other will then result in the formation of the various reaction chambers, interconnected by the appropriate fluid channels.

In particularly preferred embodiments, the body of the device is made from at least one injection molded, press molded or machined polymeric part that has one or more wells or depressions manufactured into its surface to define several of the walls of the reaction chamber or chambers. Molds or mold faces for producing these injection molded parts may generally be fabricated using the methods described herein for, e.g., conventional machining or silicon molds. Examples of suitable polymers for injection molding or machining include, e.g., polycarbonate, polystyrene, polypropylene, polyethylene, acrylic, and commercial polymers such as Kapton, Valox, Teflon, ABS, Delrin and the like. A second part that is similarly planar in shape is mated to the surface of the polymeric part to define the remaining wall of the reaction chamber(s). Published PCT Application No. 95/33846, incorporated herein by reference, describes a device that is used to package individual oligonucleotide arrays. The device includes a hybridization chamber disposed within a planar body. The chamber is fluidly connected to an inlet port and an outlet port via flow channels in the body of the device. The body includes a plurality of injection molded planar parts that are mated to form the body of the device, and which define the flow channels and hybridization chamber.

The surfaces of the fluid channels and reaction chambers which contact the samples and reagents may also be modified to better accommodate a desired reaction. Surfaces may be made more hydrophobic or more hydrophilic depending upon the particular application. Alternatively, surfaces may be coated with any number of materials in order to make the overall system more compatible to the reactions being carried out. For example, in the case of nucleic acid analyses, it may be desirable to coat the surfaces with a non-stick coating, e.g., a Teflon, parylene or silicon, to prevent adhesion of nucleic acids to the surface. Additionally, insulator coatings may also be desirable in those instances where electrical leads are placed in contact with fluids, to prevent shorting out, or excess gas formation from electrolysis. Such insulators may include those well known in the art, e.g., silicon oxide, ceramics or the like. Additional surface treatments are described in greater detail below.

FIGS. 2A and 2B show a schematic representation of one embodiment of a reaction chamber for inclusion in the device of the invention. The reaction chamber includes a machined or injection molded polymeric part 102 which has a well 104 manufactured, i.e., machined or molded, into its surface. This well may be closed at the end opposite the well opening as shown in FIG. 2A, or optionally, may be supplied with an additional opening 118 for inclusion of an optional vent, as shown in FIG. 2B.

The reaction chamber is also provided with additional elements for transporting a fluid sample to and from the reaction chamber. These elements include one or more fluid channels (122 and 110 in FIGS. 2A and 2B, respectively) which connect the reaction chamber to an inlet/outlet port for the overall device, additional reaction chambers, storage chambers or one or more analytical chambers.

A second part 124, typically planar in structure, is mated to the polymeric part to define a closure for the reaction chamber. This second part may incorporate the fluid channels, as shown in FIGS. 2A and 2B, or may merely define a further wall of the fluid channels provided in the surface of the first polymeric part (not shown). Typically, this second part will comprise a series of fluid channels manufactured into one of its surfaces, for fluidly connecting the reaction chamber to an inlet port in the overall device or to another reaction or analytical chamber. Again, this second part may be a second polymeric part made by injection molding or machining techniques. Alternatively, this second part may be manufactured from a variety of other materials, including glass, silica, silicon or other crystalline substrates. Microfabrication techniques suited for these substrates are generally well known in the art and are described above.

In a first preferred embodiment, the reaction chamber is provided without an inlet/outlet valve structure, as shown in FIG. 2A. For these embodiments, the fluid channels 122 may be provided in the surface of the second part that is mated with the surface of the polymeric part such that upon mating the second part to the first polymeric part, the fluid channel 122 is fluidly connected to the reaction chamber 104.

Alternatively, in a second preferred embodiment, the reaction chamber may be provided with an inlet/outlet valve structure for sealing the reaction chamber to retain a fluid sample therein. An example of such a valve structure is shown in FIG. 2B. In particular, the second part 124 mated to the polymeric part may comprise a plurality of mated planar members, wherein a first planar member 106 is mated with the first polymeric part 102 to define a wall of the reaction chamber. The first planar member 106 has an opening 108 disposed therethrough, defining an inlet to the reaction chamber. This first planar member also includes a fluid channel 110 etched in the surface opposite the surface that is mated with the first polymeric part 102. The fluid channel terminates adjacent to, but not within the reaction chamber inlet 108. The first planar member will generally be manufactured from any of the above described materials, using the above-described methods. A second planar member 112 is mated to the first and includes a diaphragm valve 114 which extends across the inlet 108 and overlaps with the fluid channel 110 such that deflection of the diaphragm results in a gap between the first and second planar members, thereby creating a fluid connection between the reaction chamber 104 and the fluid channel 110, via the inlet 108. Deflection of the diaphragm valve may be carried out by a variety of methods including, e.g., application of a vacuum, electromagnetic and/or piezoelectric actuators coupled to the diaphragm valve, and the like. To allow for a deflectable diaphragm, the second planar member will typically be fabricated, at least in part, from a flexible material, e.g., silicon, silicone, latex, Mylar, polyimide, Teflon or other flexible polymers. As with the reaction chambers and fluid channels, these diaphragms will also be of miniature scale. Specifically, valve and pump diaphragms used in the device will typically range in size depending upon the size of the chamber or fluid passage to which they are fluidly connected. In general, however, these diaphragms will be in the range of from about 0.5 to about 5 mm for valve diaphragms, and from about 1 to about 20 mm in diameter for pumping diaphragms. As shown in FIG. 2B, second part 124 includes an additional planar member 116 having an opening 126 for application of pressure or vacuum for deflection of valve 114.

Where reagents involved in a particular analysis are incompatible with the materials used to manufacture the device, e.g., silicon, glass or polymeric parts, a variety of coatings may be applied to the surfaces of these parts that contact these reagents. For example, components that have silicon elements may be coated with a silicon nitride layer or a metallic layer of, e.g., gold or nickel, may be sputtered or electroplated on the surface to avoid adverse reactions with these reagents. Similarly, inert polymer coatings, e.g., Teflon and the like, parylene coatings, or surface silanation modifications may also be applied to internal surfaces of the chambers and/or channels.

The reaction/storage chamber 104 shown in FIG. 2B is also shown with an optional vent 118, for release of displaced gas present in the chamber when the fluid is introduced. In preferred aspects, this vent may be fitted with a gas permeable fluid barrier 120, which permits the passage of gas without allowing for the passage of fluid, e.g., a poorly wetting filter plug. A variety of materials are suitable for use as poorly wetting filter plugs including, e.g., porous hydrophobic polymer materials, such as spun fibers of acrylic, polycarbonate, Teflon, pressed polypropylene fibers, or any number commercially available filter plugs (American Filtrona Corp., Richmond, Va., Gelman Sciences, and the like). Alternatively, a hydrophobic membrane can be bonded over a thru-hole to supply a similar structure. Modified acrylic copolymer membranes are commercially available from, e.g., Gelman Sciences (Ann Arbor, Mich.) and particle-track etched polycarbonate membranes are available from Poretics, Inc. (Livermore, Calif.). Venting of heated chambers may incorporate barriers to evaporation of the sample, e.g., a reflux chamber or a mineral oil layer disposed within the chamber, and over the top surface of the sample, to permit the evolution of gas while preventing excessive evaporation of fluid from the sample.

As described herein, the overall geometry of the device of the invention may take a number of forms. For example, the device may incorporate a plurality of reaction chambers, storage chambers and analytical chambers, arranged in series, whereby a fluid sample is moved serially through the chambers, and the respective operations performed in these chambers. Alternatively, the device may incorporate a central fluid distribution channel or chamber having the various reaction/storage/analytical chambers arranged around and fluidly connected to the central channel or chamber, which central channel or chamber acts as a conduit or hub for sample redistribution to the various chambers.

Figure 3:
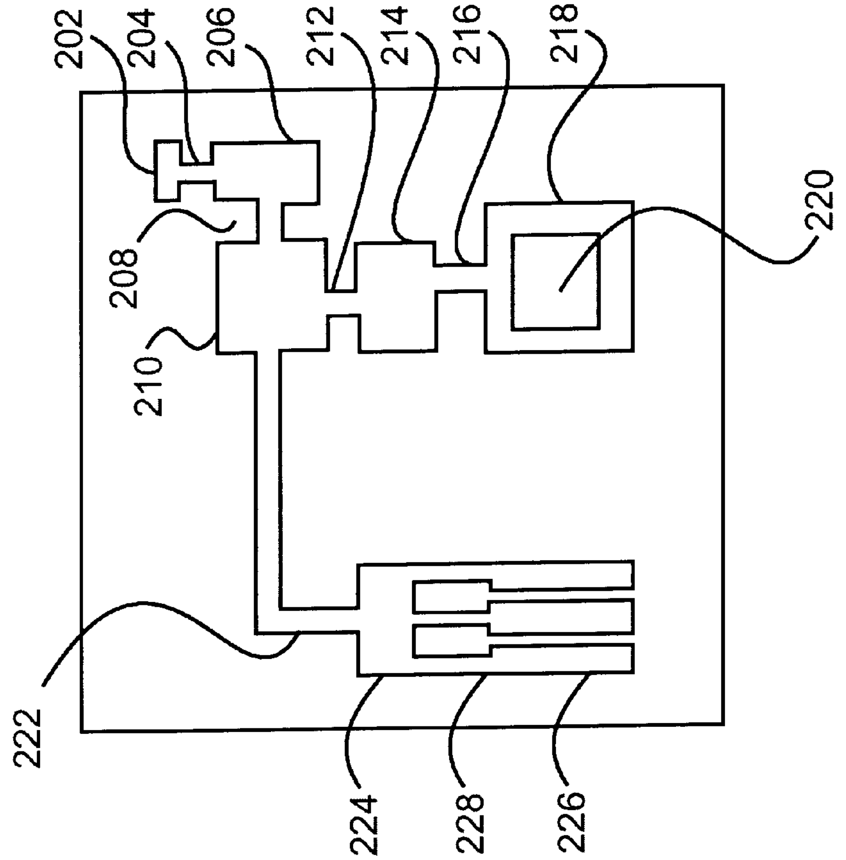
FIG. 3 shows a schematic representation of a miniature integrated diagnostic device having a number of reaction chambers arranged in a serial geometry.

An example of the serial geometry of the device is shown in FIG. 3. In particular, the illustrated device includes a plurality of reaction/storage/analytical chambers for performing a number of the operations described above, fluidly connected in series.

The schematic representation of the device in FIG. 3 shows a device that comprises several reaction chambers arranged in a serial geometry. Specifically, the body of the device 200 incorporates reaction chambers 202, 206, 210, 214 and 218. These chambers are fluidly connected in series by fluid channels 208, 212 and 216, respectively.

In carrying out the various operations outlined above, each of these reaction chambers is assigned one or more different functions. For example, reaction chamber 202 may be a sample collection chamber which is adapted for receiving a fluid sample, i.e., a cell containing sample. For example, this chamber may include an opening to the outside of the device adapted for receipt of the sample. The opening will typically incorporate a sealable closure to prevent leakage of the sample, e.g., a valve, check-valve, or septum, through which the sample is introduced or injected. In some embodiments, the apparatus may include a hypodermic needle or other sample conduit, integrated into the body of the device and in fluid connection with the sample collection chamber, for direct transfer of the sample from the host, patient, sample vial or tube, or other origin of the sample to the sample collection chamber.

Additionally, the sample collection chamber may have disposed therein, a reagent or reagents for the stabilization of the sample for prolonged storage, as described above. Alternatively, these reagents may be disposed within a reagent storage chamber adjacent to and fluidly connected with the sample collection chamber.

The sample collection chamber is connected via a first fluid channel 204 to second reaction chamber 206 in which the extraction of nucleic acids from the cells within the sample may be performed. This is particularly suited to analytical operations to be performed where the samples include whole cells. The extraction chamber will typically be connected to sample collection chamber, however, in some cases, the extraction chamber may be integrated within and exist as a portion of the sample collection chamber. As previously described, the extraction chamber may include physical and or chemical means for extracting nucleic acids from cells.

The extraction chamber is fluidly connected via a second fluid channel 208, to third reaction chamber 210 in which amplification of the nucleic acids extracted from the sample is carried out. The amplification process begins when the sample is introduced into the amplification chamber. As described previously, amplification reagents may be exogenously introduced, or will preferably be predisposed within the reaction chamber. However, in alternate embodiments, these reagents will be introduced to the amplification chamber from an optional adjacent reagent chamber or from an external source through a sealable opening in the amplification chamber.

For PCR amplification methods, denaturation and hybridization cycling will preferably be carried out by repeated heating and cooling of the sample. Accordingly, PCR based amplification chambers will typically include a temperature controller for heating the reaction to carry out the thermal cycling. For example, a heating element or temperature control block may be disposed adjacent the external surface of the amplification chamber thereby transferring heat to the amplification chamber. In this case, preferred devices will include a thin external wall for chambers in which thermal control is desired. This thin wall may be a thin cover element, e.g., polycarbonate sheet, or high temperature tape, i.e. silicone adhesive on Kapton tape (commercially available from, e.g., 3M Corp.). Micro-scale PCR devices have been previously reported. For example, published PCT Application No. WO 94/05414, to Northrup and White reports a miniaturized reaction chamber for use as a PCR chamber, incorporating microheaters, e.g., resistive heaters. The high surface area to volume ratio of the chamber allows for very rapid heating and cooling of the reagents disposed therein. Similarly, U.S. Pat. No. 5,304,487 to Wilding et al., previously incorporated by reference, also discusses the use of a microfabricated PCR device.

In preferred embodiments, the amplification chamber will incorporate a controllable heater disposed within or adjacent to the amplification chamber, for thermal cycling of the sample. Thermal cycling is carried out by varying the current supplied to the heater to achieve the desired temperature for the particular stage of the reaction. Alternatively, thermal cycling for the PCR reaction may be achieved by transferring the fluid sample among a number of different reaction chambers or regions of the same reaction chamber, having different, although constant temperatures, or by flowing the sample through a serpentine channel which travels through a number of varied temperature 'zones'. Heating may alternatively be supplied by exposing the amplification chamber to a laser or other light or electromagnetic radiation source.

The amplification chamber is fluidly connected via a fluid channel, e.g., fluid channel 212, to an additional reaction chamber 214 which can carry out additional preparative operations, such as labeling or fragmentation.

A fourth fluid channel 216 connects the labeling or fragmentation chamber to an analytical chamber 218. As shown, the analytical chamber includes an oligonucleotide array 220 as the bottom surface of the chamber. The analytical system may optionally, or additionally comprise a microcapillary electrophoresis device 226 and additional preparative reaction chambers, e.g., 224 for performing, e.g., extension reactions, fluidly connected to, e.g., chamber 210. The analytical chamber will typically have as at least one surface, a transparent window for observation or scanning of the particular analysis being performed.

FIGS. 4A–C illustrate an embodiment of a microcapillary electrophoresis device. In this embodiment, the sample to be analyzed is introduced into sample reservoir 402. This sample reservoir may be a separate chamber, or may be merely a portion of the fluid channel leading from a previous reaction chamber. Reservoirs 404, 406 and 414 are filled with sample/running buffer. FIG. 4A illustrates the loading of the sample by plug loading, where the sample is drawn across the intersection of loading channel 416 and capillary channel 412, by application of an electrical current across buffer reservoir 406 and sample reservoir 402. In alternative embodiments, the sample is "stack" loaded by applying an electrical current across sample reservoir 402 and waste reservoir 414, as shown in FIG. 4B. Following sample loading, an electrical field is applied across buffer reservoir 404 and waste reservoir 414, electrophoresing the sample through the capillary channel 412. Running of the sample is shown in FIG. 4C. Although only a single capillary is shown in FIGS. 4A–C, the device of the present invention may typically comprise more than one capillary, and more typically, will comprise an array of four or more capillaries, which are run in parallel. Fabrication of the microcapillary electrophoresis device may generally be carried using the methods described herein and as described in e.g., Woolley and Mathies, Proc. Nat'l Acad. Sci. USA 91:11348–11352 (1994), incorporated herein by reference in its entirety for all purposes. Typically, each capillary will be fluidly connected to a separate extension reaction chamber for incorporation of a different dideoxynucleotide.

An alternate layout of the reaction chambers within the device of the invention, as noted above, includes a centralized geometry having a central chamber for gathering and distribution of a fluid sample to a number of separate reaction/storage/analytical chambers arranged around, and fluidly connected to the central chamber. An example of this centralized geometry is shown in FIG. 5. In the particular device shown, a fluid sample is introduced into the device through sample inlet 502, which is typically fluidly connected to a sample collection chamber 504. The fluid sample is then transported to a central chamber 508 via fluid channel 506. Once within the central chamber, the sample may be transported to any one of a number of reaction/storage/analytical chambers (510, 512, 514) which are arranged around and fluidly connected to the central chamber. As shown, each of reaction chambers 510, 512 and 514, includes a diaphragm 516, 518 and 520, respectively, as shown in FIG. 2B, for opening and closing the fluid connection between the central chamber 508 and the reaction chamber. Additional reaction chambers may be added fluidly connected to the central chamber, or alternatively, may be connected to any of the above described reaction chambers.

In certain aspects, the central chamber may have a dual function as both a hub and a pumping chamber. In particular, this central pumping chamber can be fluidly connected to one or more additional reaction and/or storage chambers and one or more analytical chambers. The central pumping chamber again functions as a hub for the various operations to be carried out by the device as a whole as described above. This embodiment provides the advantage of a single pumping chamber to deliver a sample to numerous operations, as well as the ability to readily incorporate additional sample preparation operations within the device by opening another valve on the central pumping chamber.

In particular, the central chamber 508 may incorporate a diaphragm pump as one surface of the chamber, and in preferred aspects, will have a zero displacement when the diaphragm is not deflected. The diaphragm pump will generally be similar to the valve structure described above for the reaction chamber. For example, the diaphragm pump will generally be fabricated from any one of a variety of flexible materials, e.g., silicon, latex, Teflon, Mylar, silicone, and the like. In particularly preferred embodiments, the diaphragm pump is silicon.

Figure 5A:
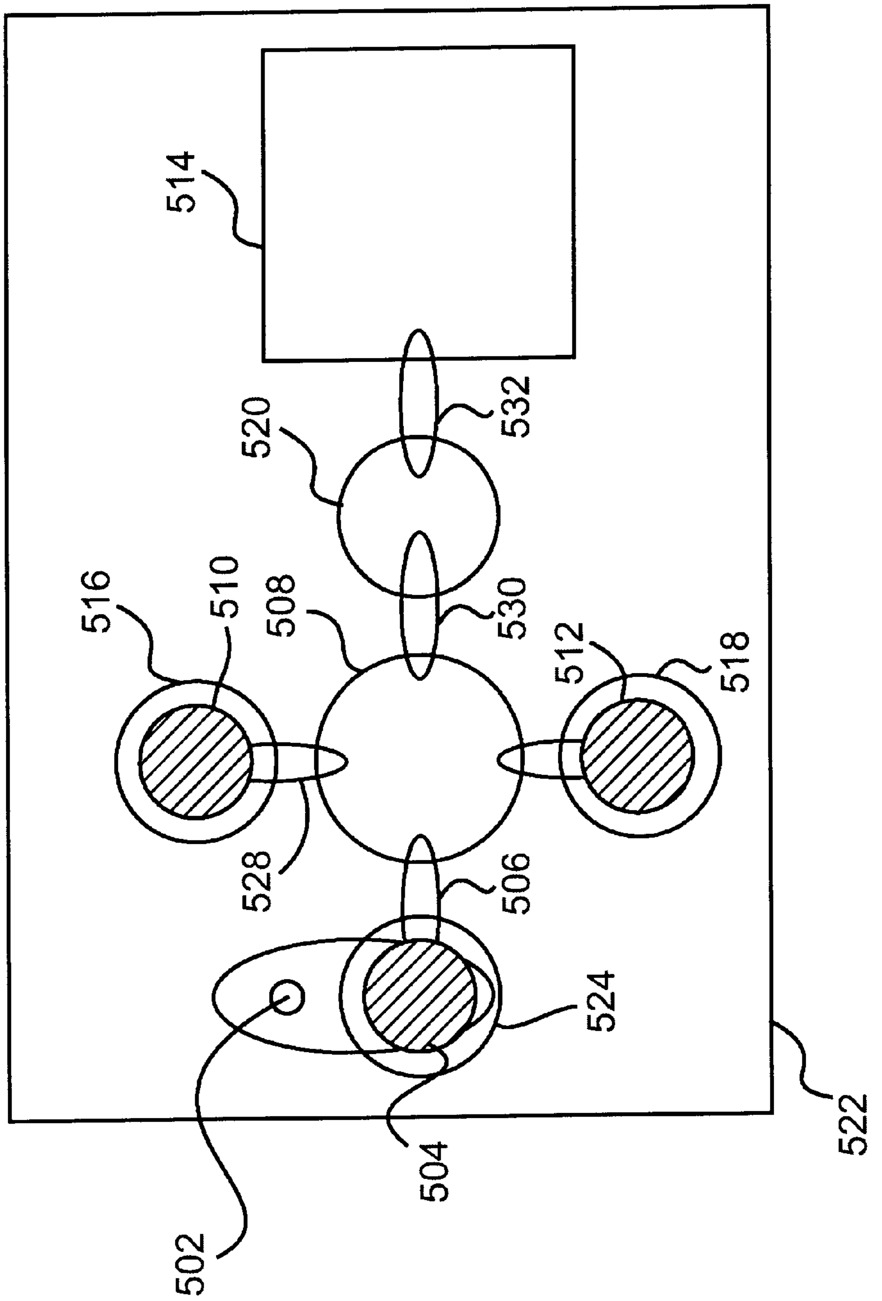
FIG. 5A illustrates a top view of a miniature integrated device which employs a centralized geometry.
Figure 5B:
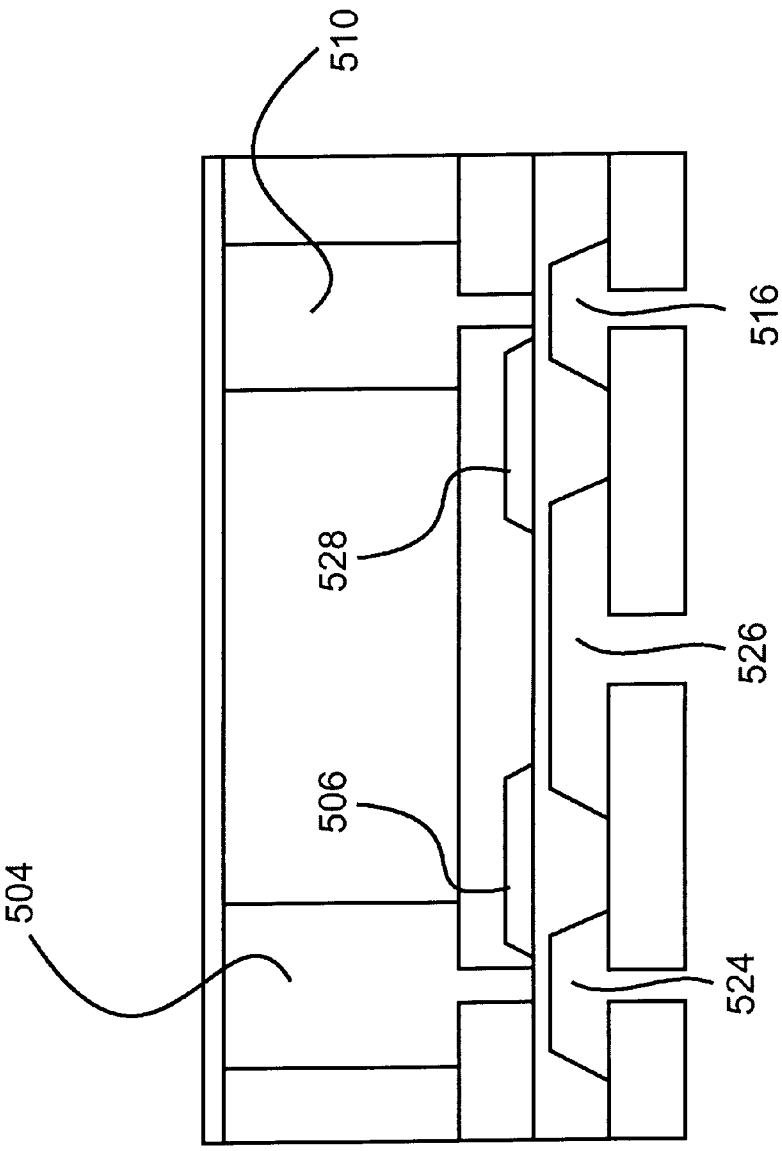
FIG. 5B shows a side view of the same device wherein the central chamber is a pumping chamber, and employing diaphragm valve structures for sealing reaction chambers.

With reference to both FIGS. 5A and 5B, central chamber 508 is fluidly connected to sample collection chamber 504, via fluid channel 506. The sample collection chamber end of fluid channel 506 includes a diaphragm valve 524 for arresting fluid flow. A fluid sample is typically introduced into sample collection chamber through a sealable opening 502 in the body of the device, e.g., a valve or septum. Additionally, sample chamber 504 may incorporate a vent to allow displacement of gas or fluid during sample introduction identically to FIG. 2B.

Once the sample is introduced into the sample collection chamber, it may be drawn into the central pumping chamber 508 by the operation of pump diaphragm 526. Specifically, opening of sample chamber valve 524 opens fluid channel 506. Subsequent pulling or deflection of pump diaphragm 526 creates negative pressure within pumping chamber 508, thereby drawing the sample through fluid channel 506 into the central chamber. Subsequent closing of the sample chamber valve 524 and relaxation of pump diaphragm 526, creates a positive pressure within pumping chamber 508, which may be used to deliver the sample to additional chambers in the device. For example, where it is desired to add specific reagents to the sample, these reagents may be stored in liquid or solid form within an adjacent storage chamber 510. Opening valve 516 opens fluid channel 528, allowing delivery of the sample into storage chamber 510 upon relaxation of the diaphragm pump. The operation of pumping chamber may further be employed to mix reagents, by repeatedly pulling and pushing the sample/reagent mixture to and from the storage chamber. This has the additional advantage of eliminating the necessity of including additional mixing components within the device. Additional chamber/valve/fluid channel structures may be provided fluidly connected to pumping chamber 508 as needed to provide reagent storage chambers, additional reaction chambers or additional analytical chambers. FIG. 5A illustrates an additional reaction/storage chamber 514 and valve 520, fluidly connected to pumping chamber 508 via fluid channel 530. This will typically vary depending upon the nature of the sample to be analyzed, the analysis to be performed, and the desired sample preparation operation. Following any sample preparation operation, opening valve 520 and closure of other valves to the pumping chamber, allows delivery of the sample through fluid channels 530 and 532 to reaction chamber 514, which may include an analytical device such as an oligonucleotide array for determining the hybridization of nucleic acids in the sample to the array, or a microcapillary electrophoresis device for performing a size based analysis of the sample.

The transportation of fluid within the device of the invention may be carried out by a number of varied methods. For example, fluid transport may be affected by the application of pressure differentials provided by either external or internal sources. Alternatively, internal pump elements which are incorporated into the device may be used to transport fluid samples through the device.

In a first embodiment, fluid samples are moved from one reaction/storage/analytical chamber to another chamber via fluid channels by applying a positive pressure differential from the originating chamber, the chamber from which the sample is to be transported, to the receiving chamber, the chamber to which the fluid sample is to be transported. In order to apply the pressure differentials, the various reaction chambers of the device will typically incorporate pressure inlets connecting the reaction chamber to the pressure source (positive or negative). For ease of discussion, the application of a negative pressure, i.e., to the receiving chamber, will generally be described herein. However, upon reading the instant disclosure, one of ordinary skill in the art will appreciate that application of positive pressure, i.e., to the originating chamber, will be as effective, with only slight modifications, which will be illustrated as they arise herein.

In one method, application of the pressure differential to a particular reaction chamber may generally be carried out by selectively lowering the pressure in the receiving chamber. Selective lowering of the pressure in a particular receiving chamber may be carried out by a variety of methods. For example, the pressure inlet for the reaction chambers may be equipped with a controllable valve structure which may be selectively operated to be opened to the pressure source. Application of the pressure source to the sample chamber then forces the sample into the next reaction chamber which is at a lower pressure.

Typically, the device will include a pressure/vacuum manifold for directing an external vacuum source to the various reaction/storage/analytical chambers. A particularly elegant example of a preferred vacuum pressure manifold is illustrated in FIGS. 6A, 6B and 6C.

The vacuum/pressure manifold produces a stepped pressure differential between each pair of connected reaction chambers. For example, assuming ambient pressure is defined as having a value of 1, a vacuum is applied to a first reaction chamber, which may be written $1-3x$, where x is an incremental pressure differential. A vacuum of $1-2x$ is applied to a second reaction chamber in the series, and a vacuum of $1-x$ is applied to a third reaction chamber. Thus, the first reaction chamber is at the lowest pressure and the third is at the highest, with the second being at an intermediate level. All chambers, however, are below ambient pressure, e.g., atmospheric. The sample is drawn into the first reaction chamber by the pressure differential between ambient pressure (1) and the vacuum applied to the reaction chamber ($1-3x$), which differential is $-3x$. The sample does not move to the second reaction chamber due to the pressure differential between the first and second reaction chambers ($1-3x$ vs. $1-2x$, respectively). Upon completion of the operation performed in the first reaction chamber, the vacuum is removed from the first chamber, allowing the first chamber to come to ambient pressure, e.g., 1. The sample is then drawn from the first chamber into the second by the pressure difference between the ambient pressure of the first reaction chamber and the vacuum of the second chamber, e.g., 1 vs. $1-2x$. Similarly, when the operation to be performed in the second reaction chamber is completed, the vacuum to this chamber is removed and the sample moves to the third reaction chamber.

Figure 6A:
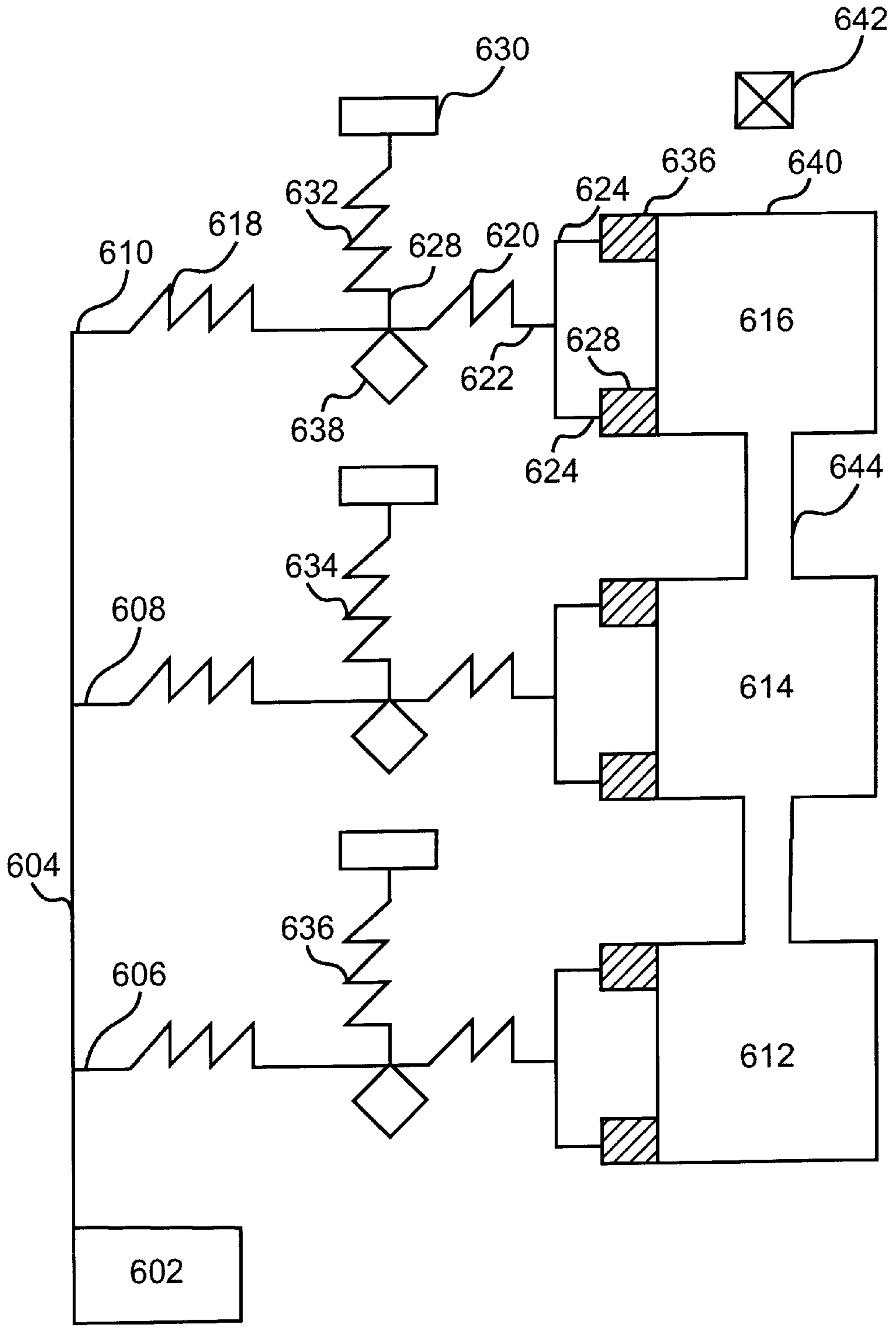
Figure 6B:
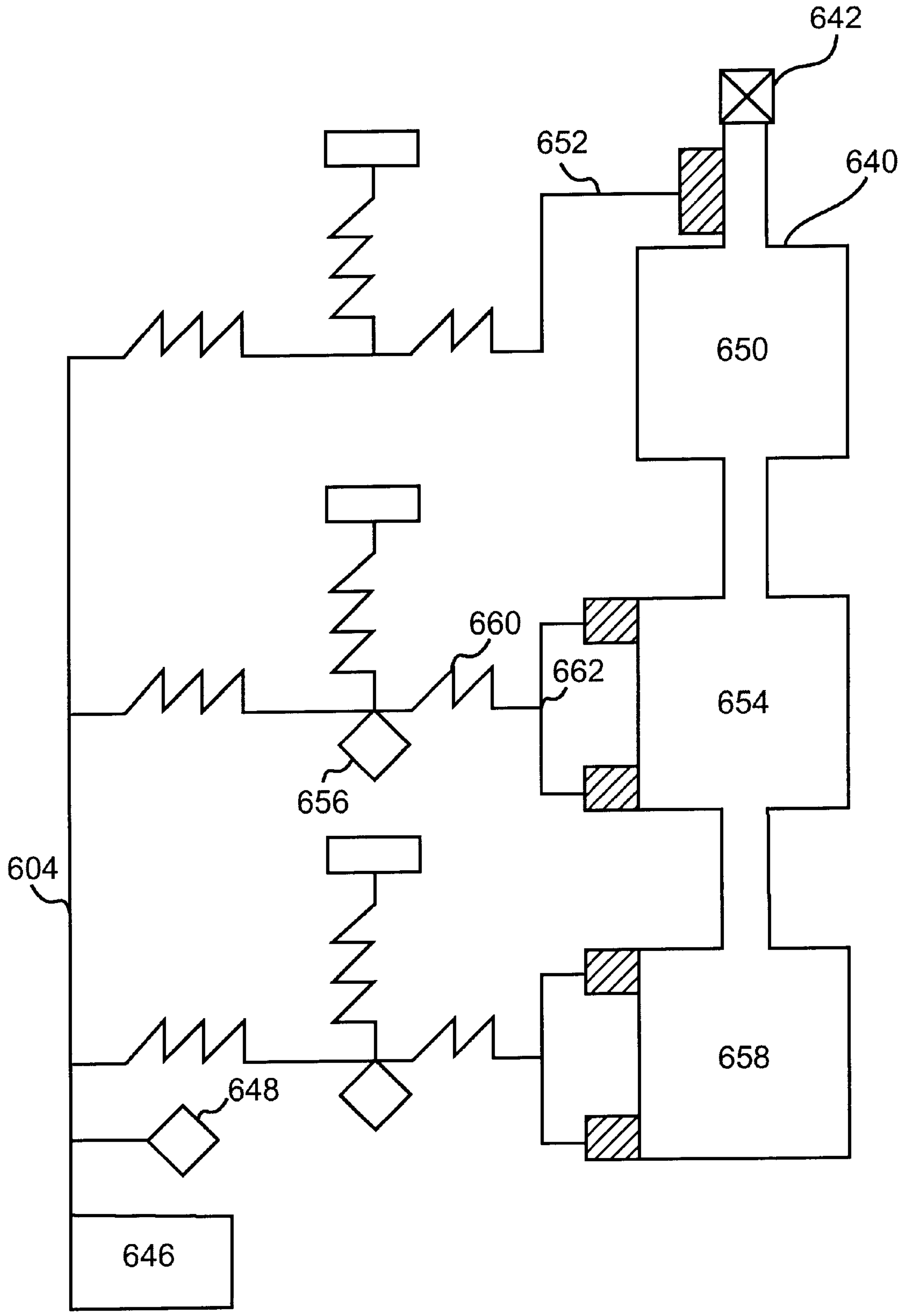
FIG. 6B shows a manifold configuration for application of positive pressures.
Figure 6C:
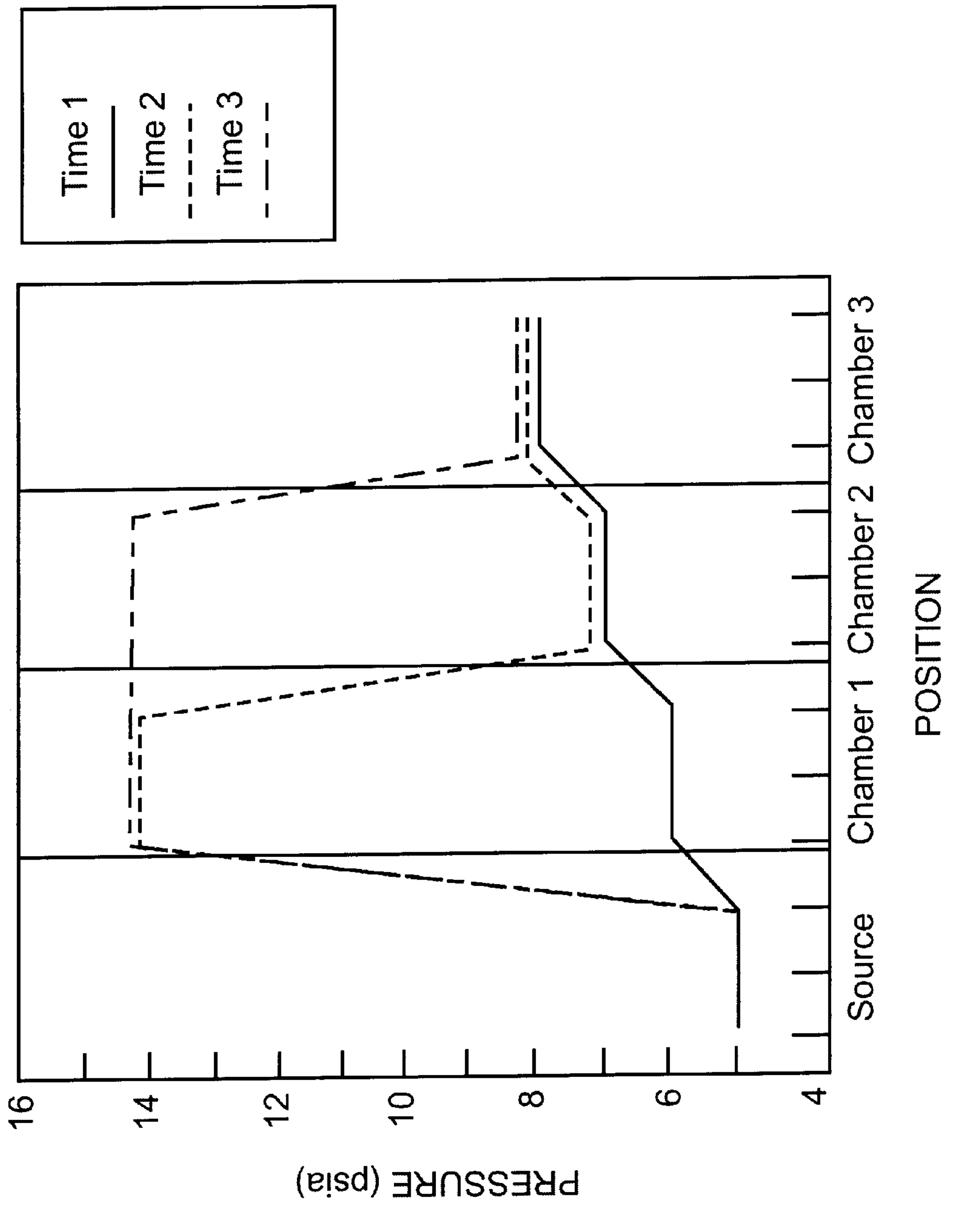
FIG. 6C illustrates a pressure profile for moving fluids among several reaction chambers.

A schematic representation of a pneumatic manifold configuration for carrying out this pressure differential fluid transport system is shown in FIG. 6A. The pneumatic manifold includes a vacuum source 602 which is coupled to a main vacuum channel 604. The main vacuum channel is connected to branch channels 606, 608 and 610, which are in turn connected to reaction chambers 612, 614 and 616, respectively, which reaction chambers are fluidly connected, in series. The first reaction chamber in the series 616 typically includes a sample inlet 640 which will typically include a sealable closure for retaining the fluid sample and the pressure within the reaction chamber. Each branch channel is provided with one or more fluidic resistors 618 and 620 incorporated within the branch channel. These fluidic resistors result in a transformation of the pressure from the pressure/vacuum source, i.e., a step down of the gas pressure or vacuum being applied across the resistance. Fluidic resistors may employ a variety of different structures. For example, a narrowing of the diameter or cross-sectional area of a channel will typically result in a fluidic resistance through the channel. Similarly, a plug within the channel which has one or more holes disposed therethrough, which effectively narrow the channel through which the pressure is applied, will result in a fluidic resistance, which resistance can be varied depending upon the number and/or size of the holes in the plug. Additionally, the plug may be fabricated from a porous material which provides a fluidic resistance through the plug, which resistance may be varied depending upon the porosity of the material and/or the number of plugs used. Variations in channel length can also be used to vary fluidic resistance.

Each branch channel will typically be connected at a pressure node 622 to the reaction chamber via pressure inlets 624. Pressure inlets 624 will typically be fitted with poorly wetting filter plugs 626, to prevent drawing of the sample into the pneumatic manifold in the case of vacuum based methods. Poorly wetting filter plugs may generally be prepared from a variety of materials known in the art and as described above. Each branch channel is connected to a vent channel 628 which is opened to ambient pressure via vent 630. A differential fluidic resistor 632 is incorporated into vent channel 628. The fluidic resistance supplied by fluidic resistor 632 will be less than fluidic resistance supplied by fluidic resistor 634 which will be less than fluidic resistance supplied by fluidic resistor 636. As described above, this differential fluidic resistance may be accomplished by varying the diameter of the vent channel, varying the number of channels included in a single vent channel, varying channel length, or providing a plug in the vent channel having a varied number of holes disposed therethrough.

The varied fluidic resistances for each vent channel will result in a varied level of vacuum being applied to each reaction chamber, where, as described above, reaction chamber 616 may have a pressure of 1−3x, reaction chamber 614 may have a pressure of 1−2x and reaction chamber 612 may have a pressure of 1−x. The pressure of a given reaction chamber may be raised to ambient pressure, thus allowing the drawing of the sample into the subsequent chamber, by opening the chamber to ambient pressure. This is typically accomplished by providing a sealable opening 638 to ambient pressure in the branch channel. This sealable opening may be a controllable valve structure, or alternatively, a rupture membrane which may be pierced at a desired time to allow the particular reaction chamber to achieve ambient pressure, thereby allowing the sample to be drawn into the subsequent chamber. Piercing of the rupture membrane may be carried out by the inclusion of solenoid operated pins incorporated within the device, or the device's base unit (discussed in greater detail below). In some cases, it may be desirable to prevent back flow from a previous or subsequent reaction chamber which is at a higher pressure. This may be accomplished by equipping the fluid channels between the reaction chambers 644 with one-way check valves. Examples of one-way valve structures include ball and seat structures, flap valves, duck billed check valves, sliding valve structures, and the like.

A graphical illustration of the pressure profiles between three reaction chambers employing a vacuum based pneumatic manifold is shown in FIG. 6C. The solid line indicates the starting pressure of each reaction chamber/pressure node. The dotted line indicates the pressure profile during operation. The piercing of a rupture membrane results in an increase in the pressure of the reaction chamber to ambient pressure, resulting in a pressure drop being created between the particular chamber and the subsequent chamber. This pressure drop draws the sample from the first reaction chamber to the subsequent reaction chamber.

In a similar aspect, a positive pressure source may be applied to the originating chamber to push the sample into subsequent chambers. A pneumatic pressure manifold useful in this regard is shown in FIG. 6B. In this aspect, a pressure source 646 provides a positive pressure to the main channel 604. Before a sample is introduced to the first reaction chamber, controllable valve 648 is opened to vent the pressure from the pressure source and allow the first reaction chamber in the series 650 to remain at ambient pressure for the introduction of the sample. Again, the first chamber in the series typically includes a sample inlet 640 having a sealable closure 642. After the sample is introduced into the first reaction chamber 650, controllable valve 648 is closed, bringing the system up to pressure. Suitable controllable valves include any number of a variety of commercially available solenoid valves and the like. In this application, each subsequent chamber is kept at an incrementally higher pressure by the presence of the appropriate fluidic resistors and vents, as described above. A base pressure is applied at originating pressure node 652. When it is desired to deliver the sample to the second chamber 654, sealable opening 656 is opened to ambient pressure. This allows second chamber 654, to come to ambient pressure, allowing the pressure applied at the origin pressure node 652 to force the sample into the second chamber 654. Thus, illustrated as above, the first reaction chamber 650 is maintained at a pressure of 1+3x, by application of this pressure at originating pressure node 652. The second reaction chamber 654 is maintained at pressure 1+4x and the third reaction chamber 658 is maintained at a pressure of 1+5x. Opening sealable valve 656 results in a drop in the pressure of the second reaction chamber 654 to 1+2x. The pressure differential from the first to the second reaction chamber, x, pushes the sample from the first to the second reaction chamber and eventually to the third. Fluidic resistor 660 is provided between pressure node 662 and sealable valve 656 to prevent the escape of excess pressure when sealable valve 656 is opened. This allows the system to maintain a positive pressure behind the sample to push it into subsequent chambers.

In a related aspect, a controllable pressure source may be applied to the originating reaction vessel to push a sample through the device. The pressure source is applied intermittently, as needed to move the sample from chamber to chamber. A variety of devices may be employed in applying an intermittent pressure to the originating reaction chamber, e.g., a syringe or other positive displacement pump, or the like. Alternatively, for the size scale of the device, a thermopneumatic pump may be readily employed. An example of such a pump typically includes a heating element, e.g., a small scale resistive heater disposed in a pressure chamber. Also disposed in the chamber is a quantity of a controlled vapor pressure fluid, such as a fluorinated hydrocarbon liquid, e.g., fluorinert liquids available from 3M Corp. These liquids are commercially available having a wide range of available vapor pressures. An increase in the controllable temperature of the heater increases pressure in the pressure chamber, which is fluidly connected to the originating reaction chamber. This increase in pressure results in a movement of the sample from one reaction chamber to the next. When the sample reaches the subsequent reaction chamber, the temperature in the pressure chamber is reduced.

The inclusion of gas permeable fluid barriers, e.g., poorly wetting filter plugs or hydrophobic membranes, in these devices also permits a sensorless fluid direction and control system for moving fluids within the device. For example, as described above, such filter plugs, incorporated at the end of a reaction chamber opposite a fluid inlet will allow air or other gas present in the reaction chamber to be expelled during introduction of the fluid component into the chamber. Upon filling of the chamber, the fluid sample will contact the hydrophobic plug thus stopping net fluid flow. Fluidic resistances, as described previously, may also be employed as gas permeable fluid barriers, to accomplish this same result, e.g., using fluid passages that are sufficiently narrow as to provide an excessive fluid resistance, thereby effectively stopping or retarding fluid flow while permitting air or gas flow. Expelling the fluid from the chamber then involves applying a positive pressure at the plugged vent. This permits chambers which may be filled with no valve at the inlet, i.e., to control fluid flow into the chamber. In most aspects however, a single valve will be employed at the chamber inlet in order to ensure retention of the fluid sample within the chamber, or to provide a mechanism for directing a fluid sample to one chamber of a number of chambers connected to a common channel.

Figure 11A:
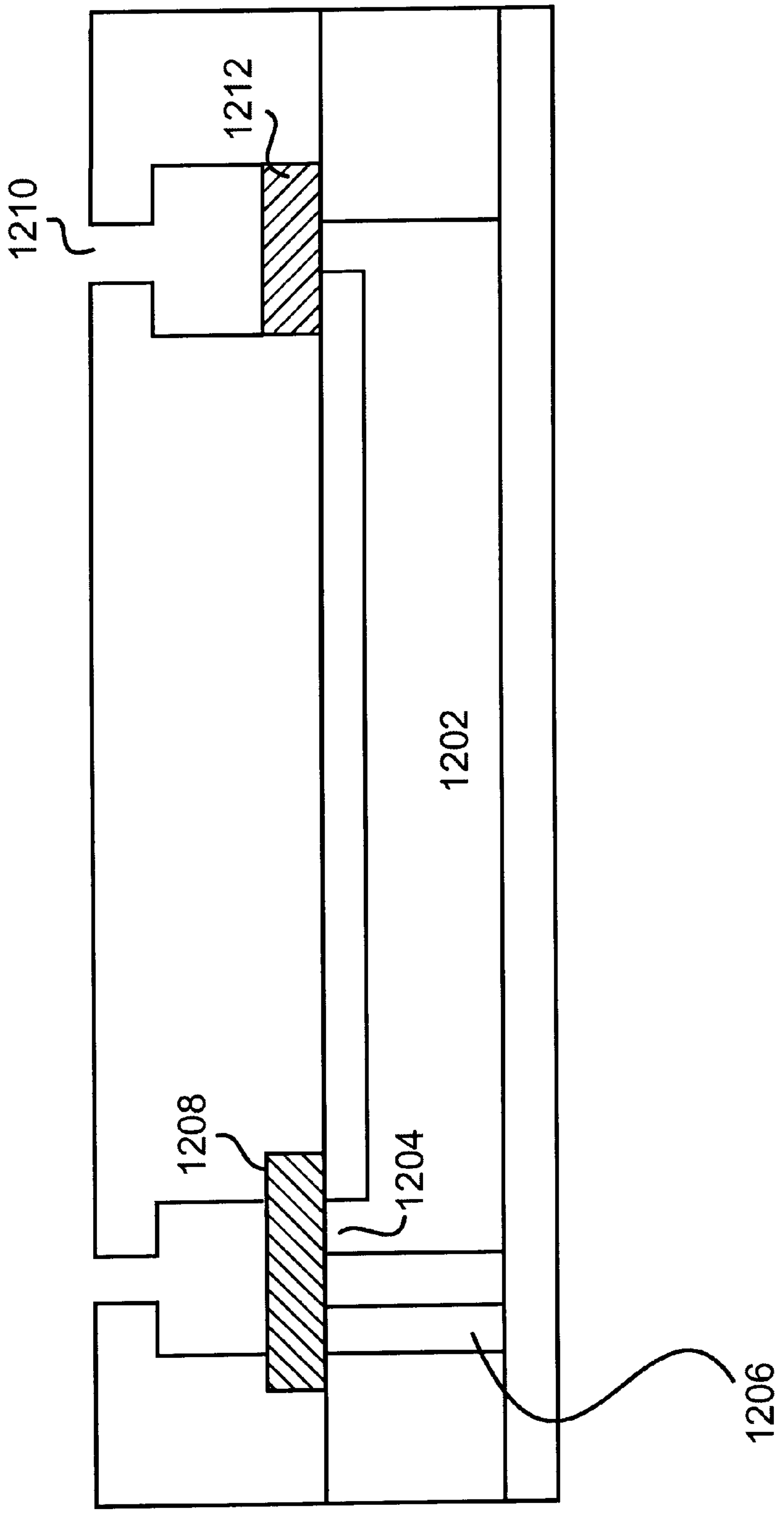
FIGS. 11A–C show a schematic representation of a miniature integrated device employing a pneumatic fluid direction system utilizing a gas permeable fluid barrier bound vents, e.g., a poorly wetting or hydrophobic membrane, and pneumatically controlled valves.
Figure 11B:
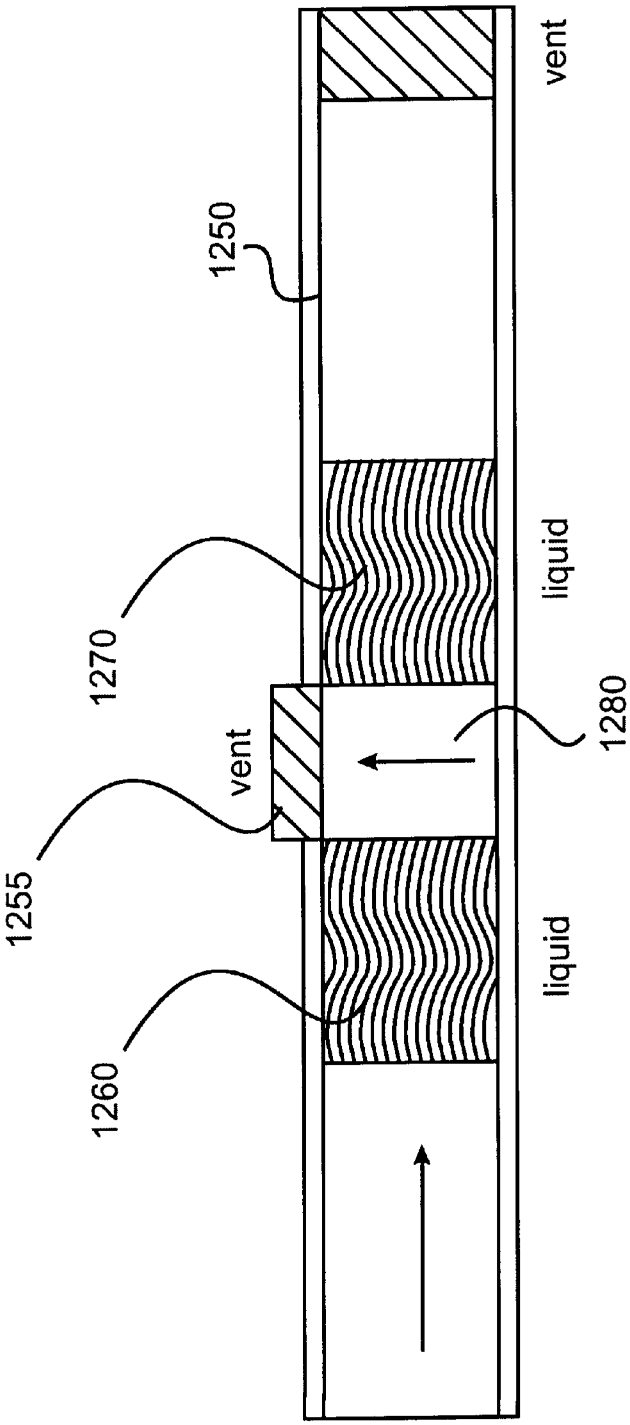

A schematic representation of a reaction chamber employing this system is shown in FIG. 11A. In brief, the reaction chamber 1202 includes a fluid inlet 1204 which is sealed from a fluid passage 1206 by a valve 1208. Typically, this valve can employ a variety of structures, as described herein, but is preferably a flexible diaphragm type valve which may be displaced pneumatically, magnetically or electrically. In preferred aspects, the valves are controlled pneumatically, e.g., by applying a vacuum to the valve to deflect the diaphragm away from the valve seat, thereby creating an opening into adjoining passages. At the end opposite from the inlet, is an outlet vent 1210, and disposed across this outlet vent is a porous hydrophobic membrane 1212. A number of different commercially available hydrophobic membranes may be used as described herein, including, e.g., Versapore 200 R membranes available from Gelman Sciences. Fluid introduced into the reaction chamber fills the chamber until it contacts the membrane 1212. Closure of the valve then allows performance of reactions within the reaction chamber without influencing or influence from elements outside of the chamber.

In another example, these vents or membranes may be used for degassing or debubbling fluids within the device. For degassing purposes, for example, a chamber may be provided with one or more vents or with one wall completely or substantially bounded by a hydrophobic membrane to allow the passage of dissolved or trapped gases. Additionally, vacuum may be applied on the external surface of the membrane to draw gases from the sample fluids. Due to the small cross sectional dimensions of reaction chambers and fluid passages, elimination of such gases takes on greater importance, as bubbles may interfere with fluid flow, and/or result in production of irregular data.

In a related aspect, such membranes may be used for removing bubbles purposely introduced into the device, i.e., for the purpose of mixing two fluids which were previously desired to be separated. For example, discrete fluids, e.g., reagents, may be introduced into a single channel or debubbling chamber, separated by a gas bubble which is sufficient to separate the fluid plugs but not to inhibit fluid flow. These fluid plugs may then be flowed along a channel having a vent disposed therein, which vent includes a hydrophobic membrane. As the fluid plugs flow past the membrane, the gas will be expelled across the membrane whereupon the two fluids will mix. A schematic illustration of such a debubbling chamber is shown in FIG. 12B where chamber 1250 has a vent 1255 disposed therein. Fluid plugs 1260 and 1270 can be moved together by way of increased pressure acting at opposite ends of chamber 1250 as air bubble 1280 is expelled through vent 1255.

Alternatively, dissolved gasses can be liberated by heating the liquid and positioning a vent along the entire length of the heating chamber.

Figure 11C:
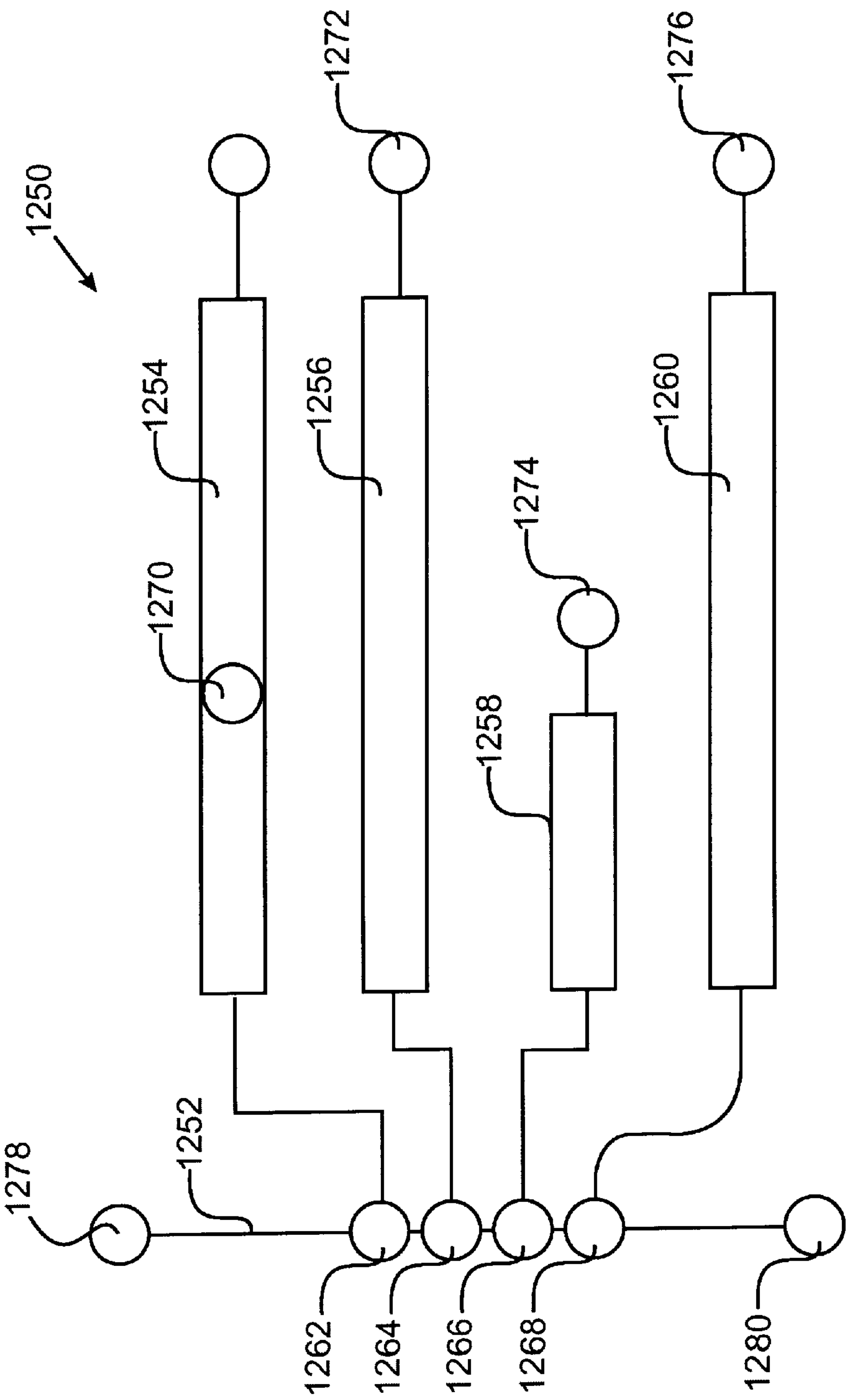

FIG. 11C shows a schematic illustration of a device employing a fluid flow system which utilizes hydrophobic membrane bound vents for control of fluid flow. As shown, the device 1250 includes a main channel (or common channel) 1252. The main channel is fluidly connected to a series of separate chambers 1254–1260. Each of these fluid connections with the main channel 1252 is mediated (opened or closed) by the inclusion of a separate valve 1262–1268, respectively, at the intersection of these fluid connections with the main channel. Further, each of the various chambers will typically include a vent port 1270–1276, which vent ports will typically be bounded by a hydrophobic or poorly wetting membrane. The basic design of this system is reflected in the device schematic shown in FIG. 5, as well, in that it employs a central distribution chamber or channel.

In operation, samples or other fluids may be introduced into the main channel 1252 via a valved or otherwise sealable liquid inlet 1278 or 1280. Application of a positive pressure to the fluid inlet, combined with the selective opening of the elastomeric valve at the fluid connection of a selected chamber with the main channel will force the fluid into that chamber, expelling air or other gases through the vent port at the terminus of the selected chamber, until that vent is contacted with the fluid, whereupon fluid flow is stopped. The valve to the selected chamber may then be returned to the closed position to seal the fluid within the chamber. As described above, the requisite pressure differential needed for fluid flow may alternatively or additionally involve the application of a negative pressure at the vent port to which fluid direction is sought.

As a specific example incorporating the device shown in FIG. 11C, a sample introduced into the main channel 1252, is first forced into the degassing chamber 1254 by opening valve 1262 and applying a positive pressure at inlet port 1278. Once the fluid has filled the degassing chamber, valve 1262 may then be closed. Degassing of the fluid may then be carried out by drawing a vacuum on the sample through the hydrophobic membrane disposed across the vent port 1270. Degassed sample may then be moved from the degassing chamber 1254 to, e.g., reaction chamber 1256, by opening valves 1262 and 1264, and applying a positive pressure to the degassing chamber vent port 1271. The fluid is then forced from the degassing chamber 1254, through main channel 1252, into reaction chamber 1256. When the fluid fills the reaction chamber, it will contact the hydrophobic membrane, thereby arresting fluid flow. As shown, the device includes a volumetric or measuring chamber 1258 as well as a storage chamber 1260, including similar valve:vent port arrangements 1266:1274 and 1268:1276, respectively. The fluid may then be selectively directed to other chambers as described.

Figure 11D:
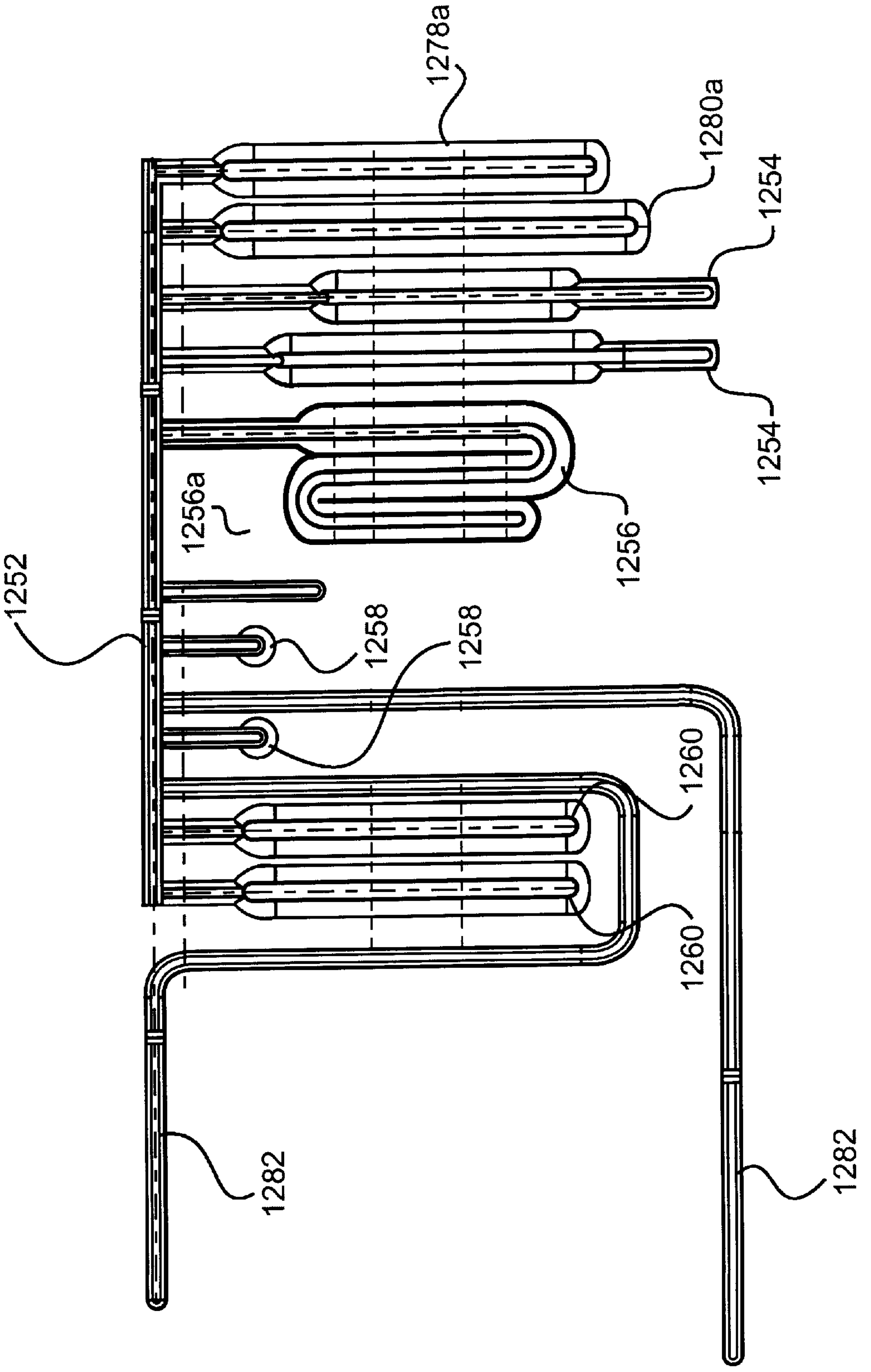
FIG. 11D is an illustration of an injection molded substrate which embodies the system schematically illustrated in FIG. 11C.

FIG. 11D shows a top view of a portion of an injection molded substrate for carrying out the operations schematically illustrated in FIG. 11C. As shown, this device includes liquid loading chambers 1278*a* and 1280*a* which are in fluid communication with the fluid inlets 1278 and 1280 (not shown). These fluid inlets may typically be fabricated into the injection molded portion, e.g., drilled into the loading chamber, or fabricated into an overlaying planar member (not shown). Also included are reaction chambers 1254, degassing chambers 1256 and 1256*a,* measuring chambers 1258, and storage chambers 1260. Each of these chambers is fluidly connected to main channel 1252.

A number of the operations performed by the various reaction chambers of the device require a controllable temperature. For example, PCR amplification, as described above, requires cycling of the sample among a strand separation temperature, an annealing reaction temperature and an extension reaction temperature. A number of other reactions, including extension, transcription and hybridization reactions are also generally carried out at optimized, controlled temperatures. Temperature control within the device of the invention is generally supplied by thin film resistive heaters which are prepared using methods that are well known in the art. For example, these heaters may be fabricated from thin metal films applied within or adjacent to a reaction chamber using well known methods such as sputtering, controlled vapor deposition and the like. The thin film heater will typically be electrically connected to a power source which delivers a current across the heater. The electrical connections will also be fabricated using methods similar to those described for the heaters.

Typically, these heaters will be capable of producing temperatures in excess of 100 degrees without suffering adverse effects as a result of the heating. Examples of resistor heaters include, e.g., the heater discussed in Published PCT Application No. WO 94/05414, laminated thin film NiCr/polyimide/copper heaters, as well as graphite heaters. These heaters may be provided as a layer on one surface of a reaction chamber, or may be provided as molded or machined inserts for incorporation into the reaction chambers. FIG. 2B illustrates an example of a reaction chamber 104 having a heater insert 128, disposed therein. The resistive heater is typically electrically connected to a controlled power source for applying a current across the heater. Control of the power source is typically carried out by an appropriate circuit or appropriately programmed computer. The above-described heaters may be incorporated within the individual reaction chambers by depositing a resistive metal film or insert within the reaction chamber, or alternatively, may be applied to the exterior of the device, adjacent to the particular reaction chamber, whereby the heat from the heater is conducted into the reaction chamber.

Temperature controlled reaction chambers will also typically include a miniature temperature sensor for monitoring the temperature of the chamber, and thereby controlling the application of current across the heater. A wide variety of microsensors are available for determining temperatures, including, e.g., thermocouples having a bimetallic junction which produces a temperature dependent electromotive force (EMF), resistance thermometers which include material having an electrical resistance proportional to the temperature of the material, thermistors, IC temperature sensors, quartz thermometers and the like. See, Horowitz and Hill, The Art of Electronics, Cambridge University Press 1994 (2nd Ed. 1994). One heater/sensor design that is particularly suited to the device of the present invention is described in, e.g., U.S. patent application Ser. No. 08/535,875, filed Sep. 28, 1995, and incorporated herein by reference in its entirety for all purposes. Control of reaction parameters within the reaction chamber, e.g., temperature, may be carried out manually, but is preferably controlled via an appropriately programmed computer. In particular, the temperature measured by the temperature sensor and the input for the power source will typically be interfaced with a computer which is programmed to receive and record this data, i.e., via an analog-digital/digital-analog (AD/DA) converter. The same computer will typically include programming for instructing the delivery of appropriate current for raising and lowering the temperature of the reaction chamber. For example, the computer may be programmed to take the reaction chamber through any number of predetermined time/temperature profiles, e.g., thermal cycling for PCR, and the like. Given the size of the devices of the invention, cooling of the reaction chambers will typically occur through exposure to ambient temperature, however additional cooling elements may be included if desired, e.g., coolant systems, peltier coolers, water baths, etc. Alternatively, thermoelectric coolers can be used to maintain the temperature by being pressed against the thin wall.

In addition to fluid transport and temperature control elements, one or more of the reaction chambers of the device may also incorporate a mixing function. For a number of reaction chambers, mixing may be applied merely by pumping the sample back and forth into and out of a particular reaction chamber. However, in some cases constant mixing within a single reaction/analytical chamber is desired, e.g., PCR amplification reactions and hybridization reactions.

Figure 7A:
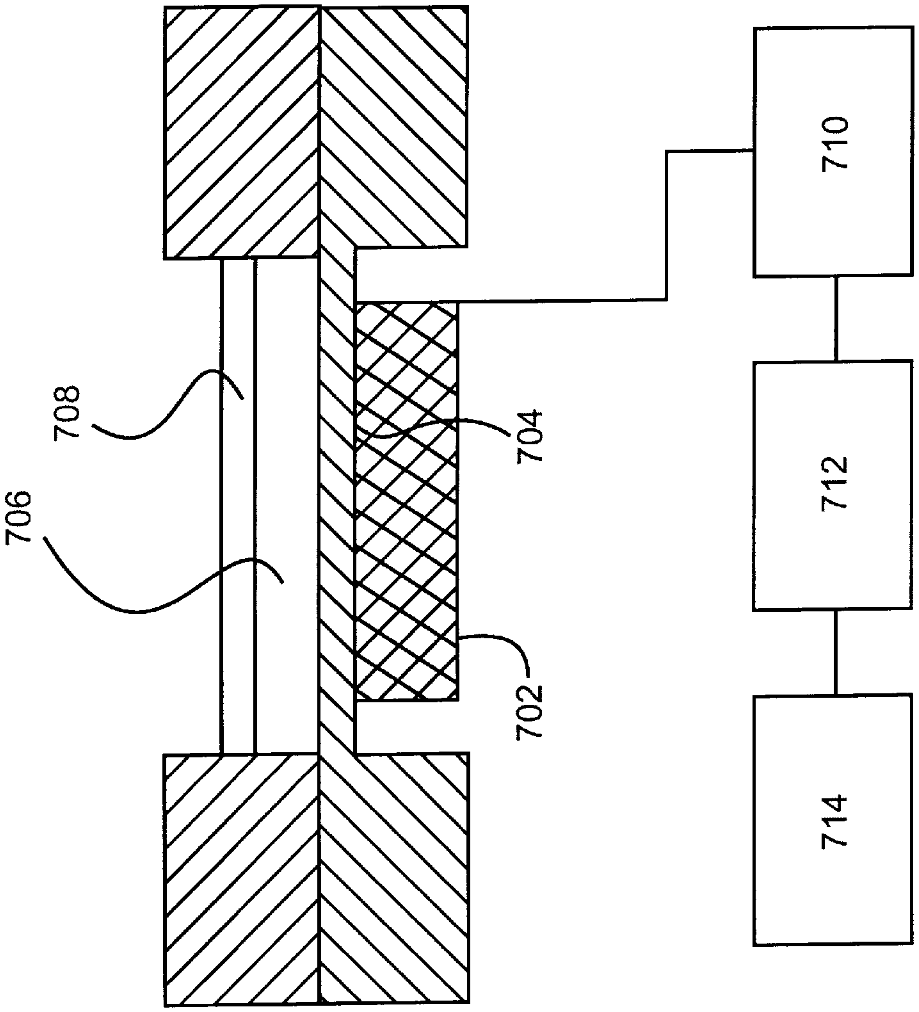
FIG. 7A shows a schematic illustration of a reaction chamber incorporating a PZT element for use in mixing the contents of the reaction chamber.

In preferred aspects, acoustic mixing is used to mix the sample within a given reaction chamber. In particular, a PZT element (element composed of lead, zirconium and titanium containing ceramic) or lithium niobate is contacted with the exterior surface of the device, adjacent to the reaction chamber, as shown in FIG. 7A. For a discussion of PZT elements for use in acoustic based methods, see, *Physical Acoustics, Principles and Methods,* Vol. I, (Mason ed., Academic Press, 1965), and Piezoelectric Technology, Data for Engineers, available from Clevite Corp. As shown, PZT element 702 is contacting the external surface 704 of hybridization chamber 706. The hybridization chamber includes as one internal surface, an oligonucleotide array 708. Application of a current to this element generates sonic vibrations which are translated to the reaction chamber whereupon mixing of the sample disposed therein occurs. The vibrations of this element result in substantial convection being generated within the reaction chamber. A symmetric mixing pattern generated within a micro reaction chamber incorporating this mixing system is shown FIG. 7B.

Incomplete contact (i.e., bonding) of the element to the device may result in an incomplete mixing of a fluid sample. As a result, the element will typically have a fluid or gel layer (not shown) disposed between the element 702 and the external surface of the device 704, e.g., water. This fluid layer will generally be incorporated within a membrane, e.g., a latex balloon, having one surface in contact with the external surface of the reaction chamber and another surface in contact with the PZT element. An appropriately programmed computer 714 may be used to control the application of a voltage to the PZT element, via a function generator 712 and RF amplifier 710 to control the rate and/or timing of mixing.

In alternate aspects, mixing may be supplied by the incorporation of ferromagnetic elements within the device which may be vibrated by supplying an alternating current to a coil adjacent the device. The oscillating current creates an oscillating magnetic field through the center of the coil which results in vibratory motion and rotation of the magnetic particles in the device, resulting in mixing, either by direct convection or acoustic streaming.

In addition to the above elements, the devices of the present invention may include additional components for optimizing sample preparation or analysis. For example, electrophoretic force may be used to draw target molecules into the surface of the array. For example, electrodes may be disposed or patterned on the surface of the array or on the surface opposite the array. Application of an appropriate electric field will either push or pull the targets in solution onto the array. A variety of similar enhancements can be included without departing from the scope of the invention.

Although it may often be desirable to incorporate all of the above described elements within a single disposable unit, generally, the cost of some of these elements and materials from which they are fabricated, may make it desirable to provide a unit that is at least partially reusable. Accordingly, in a particularly preferred embodiment, a variety of control elements for the device, e.g., temperature control, mixing and fluid transport elements may be supplied within a reusable base-unit.

For example, in a particularly preferred embodiment, the reaction chamber portion of the device can be mated with a reusable base unit that is adapted for receiving the device. As described, the base unit may include one or more heaters for controlling the temperature within selected reaction chambers within the device. Similarly, the base unit may incorporate mixing elements such as those described herein, as well as vacuum or pressure sources for providing sample mixing and transportation within the device.

As an example, the base unit may include a first surface having disposed thereon, one or more resistive heaters of the type described above. The heaters are positioned on the surface of the base unit such that when the reaction chamber device is mated to that surface, the heaters will be adjacent to and preferably contacting the exterior surface of the device adjacent to one or more reaction chambers in which temperature control is desired. Similarly, one or more mixing elements, such as the acoustic mixing elements described above, may also be disposed upon this surface of the base unit, whereby when mated with the reaction chamber device, the mixing elements contact the outer surface of the reaction/storage/analytical chambers in which such mixing is desired. For those reaction chambers in which both mixing and heating are desired, interspersed heaters and mixers may be provided on the surface of the base unit. Alternatively, the base unit may include a second surface which contacts the opposite surface of the device from the first surface, to apply heating on one exterior surface of the reaction chamber and mixing at the other.

Along with the various above-described elements, the base unit also typically includes appropriate electrical connections for linking the heating and mixing elements to an appropriate power source. Similarly, the base unit may also be used to connect the reaction chamber device itself to external power sources, pressure/vacuum sources and the like. In particular, the base unit can provide manifolds, ports and electrical connections which plug into receiving connectors or ports on the device to provide power, vacuum or pressure for the various control elements that are internal to the device. For example, mating of the device to the base unit may provide a connection from a vacuum source in the base unit to a main vacuum manifold manufactured into the device, as described above. Similarly, the base unit may provide electrical connectors which couple to complementary connectors on the device to provide electrical current to any number of operations within the device via electrical circuitry fabricated into the device. Similarly, appropriate connections are also provided for monitoring various operations of the device, e.g., temperature, pressure and the like.

For those embodiments employing a pneumatic manifold for fluid transport which relies on the piercing of rupture membranes within the device to move the sample to subsequent chambers, the base unit will also typically include one or more solenoid mounted rupture pins. The solenoid mounted rupture pins are disposed within receptacles which are manufactured into the surface of the base unit, which receptacles correspond to positions of the rupture membranes upon the device. The pins are retained below the surface of the base unit when not in operation. Activation of the solenoid extends the pin above the surface of the base unit, into and through the rupture membrane.

A schematic representation of one embodiment of a base unit is shown in FIG. 8. As shown in FIG. 8, the base unit 800 includes a body structure 802 having a mating surface 804. The body structure houses the various elements that are to be incorporated into the base unit. The base unit may also include one or more thermoelectric heating/cooling elements 806 disposed within the base unit such that when the reaction chamber containing portion of the apparatus is mated to the mating surface of the base unit, the reaction chambers will be in contact or immediately adjacent to the heating elements. For those embodiments employing a differential pressure based system for moving fluids within the device, as described above, the base unit may typically include a pressure source opening to the mating surface via the pressure source port 810. The base unit will also typically include other elements of these systems, such as solenoid 812 driven pins 814 for piercing rupture membranes. These pins are typically within recessed ports 816 in the mating surface 804. The base unit will also typically include mounting structures on the mating surface to ensure proper mating of the reaction chamber containing portion of the device to the base unit. Such mounting structures generally include mounting pins or holes (not shown) disposed on the mating surface which correspond to complementary structures on the reaction chamber containing portion of the device. Mounting pins may be differentially sized, and/or tapered, to ensure mating of the reaction chamber and base unit in an appropriate orientation. Alternatively, the base unit may be fabricated to include a well in which the reaction chamber portion mounts, which well has a nonsymmetrical shape, matching a nonsymmetrical shape of the reaction chamber portion. Such a design is similar to that used in the manufacture of audio tape cassettes and players.

In addition to the above described components, the device of the present invention may include a number of other components to further facilitate analyses. In particular, a number of the operations of sample transport, manipulation and monitoring may be performed by elements external to the device, per se. These elements may be incorporated within the above-described base unit, or may be included as further attachments to the device and/or base unit. For example, external pumps or fluid flow devices may be used to move the sample through the various operations of the device and/or for mixing, temperature controls may be applied externally to the device to maximize individual operations, and valve controls may be operated externally to direct and regulate the flow of the sample. In preferred embodiments, however, these various operations will be integrated within the device. Thus, in addition to the above described components, the integrated device of the invention will typically incorporate a number of additional components for sample transporting, direction, manipulation, and the like. Generally, this will include a plurality of micropumps, valves, mixers and heating elements.

Pumping devices that are particularly useful include a variety of micromachined pumps that have been reported in the art. For example, suitable pumps include pumps which having a bulging diaphragm, powered by a piezoelectric stack and two check valves, such as those described in U.S. Pat. Nos. 5,277,556, 5,271,724 and 5,171,132, or powered by a thermopneumatic element, as described in U.S. Pat. No. 5,126,022 piezoelectric peristaltic pumps using multiple membranes in series, and the like. The disclosure of each of these patents is incorporated herein by reference. Published PCT Application No. WO 94/05414 also discusses the use of a lamb-wave pump for transportation of fluid in micron scale channels.

Ferrofluidic fluid transport and mixing systems may also be incorporated into the device of the present invention. Typically, these systems incorporate a ferrofluidic substance which is placed into the apparatus. The ferrofluidic substance is controlled/directed externally through the use of magnetic fields produced by magnets or coils. In particular, the ferrofluidic substance provides a barrier which can be selectively moved to force the sample fluid through the apparatus, or through an individual operation of the apparatus. These ferrofluidic systems may be used for example, to reduce effective volumes where the sample occupies insufficient volume to fill the hybridization chamber. Insufficient sample fluid volume may result in incomplete hybridization with the array, and incomplete hybridization data. The ferrofluidic system is used to sandwich the sample fluid in a sufficiently small volume. This small volume is then drawn across the array in a manner which ensures the sample contacts the entire surface of the array. Ferrofluids are generally commercially available from, e.g., FerroFluidics Inc., New Hampshire.

Alternative fluid transport mechanisms for inclusion within the device of the present invention include, e.g. electrohydrodynamic pumps (see, e.g., Richter, et al. 3rd IEEE Workshop on Micro Electro Mechanical Systems, Feb. 12–14, 1990, Napa Valley, USA, and Richter et al., Sensors and Actuators 29:159–165 (1991), U.S. Pat. No. 5,126,022, each of which is incorporated herein by reference in its entirety for all purposes). Typically, such pumps employ a series of electrodes disposed across one surface of a channel or reaction/pumping chamber. Application of an electric field across the electrodes results in electrophoretic movement of nucleic acids in the sample. Indium-tin oxide films may be particularly suited for patterning electrodes on substrate surfaces, e.g., a glass or silicon substrate. These methods can also be used to draw nucleic acids onto an array. For example, electrodes may be patterned on the surface of an array substrate and modified with suitable functional groups for coupling nucleic acids to the surface of the electrodes. Application of a current between the electrodes on the surface of an array and an opposing electrode results in electrophoretic movement of the nucleic acids toward the surface of the array.

Electrophoretic pumping by application of transient electric fields can also be employed to avoid electrolysis at the surface of the electrodes while still causing sufficient sample movement. In particular, the electrophoretic mobility of a nucleic acid is not constant with the electric field applied. An increase in an electric field of from 50 to 400 v/cm results in a 30% increase in mobility of a nucleic acid sample in an acrylamide gel. By applying an oscillating voltage between a pair of electrodes capacitively coupled to the electrolyte, a net electrophoretic motion can be obtained without a net passage of charge. For example, a high electric field is applied in the forward direction of sample movement and a lower field is then applied in the reverse direction. See, e.g., Luckey, et al., Electrophoresis 14:492–501 (1993).

The above described micropumps may also be used to mix reagents and samples within the apparatus, by directing a recirculating fluid flow through the particular chamber to be mixed. Additional mixing methods may also be employed. For example, electrohydrodynamic mixers may be employed within the various reaction chambers. These mixers typically employ a traveling electric field for moving a fluid into which a charge has been introduced. See Bart, et al., *Sensors and Actuators* (1990) A21-A-23:193–197. These mixing elements can be readily incorporated into miniaturized devices. Alternatively, mixing may be carried out using thermopneumatic pumping mechanism. This typically involves the inclusion of small heaters, disposed behind apertures within a particular chamber. When the liquid in contact with the heater is heated, it expands through the apertures causing a convective force to be introduced into the chamber, thereby mixing the sample. Alternatively, a pumping mechanism retained behind two one way check valves, such as the pump described in U.S. Pat. No. 5,375,979 to Trah, incorporated herein by reference in its entirety for all purposes, can be employed to circulate a fluid sample within a chamber. In particular, the fluid is drawn into the pumping chamber through a first one-way check valve when the pump is operated in its vacuum or drawing cycle. The fluid is then expelled from the pump chamber through another one way check valve during the reciprocal pump cycle, resulting in a circular fluid flow within the reaction chamber. The pumping mechanism may employ any number of designs, as described herein, i.e., diaphragm, thermal pressure, electrohydrodynamic, etc.

It will typically be desirable to insulate electrical components of the device which may contact fluid samples, to prevent electrolysis of the sample at the surface of the component. Generally, any number of non-conducting insulating materials may be used for this function, including, e.g., Teflon coating, parylene, $SiO_2$, $Si_3N_4$, and the like. Preferably, insulating layers will be $SiO_2$, which may generally be sputtered over the surface of the component to provide an insulating layer.

The device of the present invention will also typically incorporate a number of microvalves for the direction of fluid flow within the device. A variety of microvalve designs are particularly well suited for the instant device. Examples of valves that may be used in the device are described in, e.g., U.S. Pat. No. 5,277,556 to van Lintel, incorporated herein by reference. Preferred valve structures for use in the present devices typically incorporate a membrane or diaphragm which may be deflected onto a valve seat. For example, the electrostatic valves, silicon/aluminum bimetallic actuated valves or thermopneumatic actuated valves can be readily adapted for incorporation into the device of the invention. Typically, these valves will be incorporated within or at one or both of the termini of the fluid channels linking the various reaction chambers, and will be able to withstand the pressures or reagents used in the various operations.

In alternative aspects, fluidic valves may also be employed. Such fluidic valves typically include a "liquid curtain" which comprises a fluid that is immiscible in the aqueous systems used in the device, e.g., silicone oil, ferrofluidic fluids, and the like. In operation, a fluidic valve having a range of 0.1 to 200 microns, and preferably 1 to 100 microns and more preferably, 25 to 50 microns, includes a shallow valving channel disposed transversely across and interrupting a deeper primary channel, having a range 1 to 500 microns, and preferably 10 to 250 microns, and more preferably, 150 to 200 microns. The valving channel is connected to at least one oil port. In operation, the valving channel is first filled with oil (or other appropriate fluid element), which is drawn into the channel by capillary action. When gas or liquid are forced through the primary channel, the oil, or "fluid curtain" moves aside and allows passage. In the absence of differential pressure along the primary channel, the oil will return to seal the fluid or gas behind a vapor barrier. In such cases, these fluidic valves are useful in the prevention of evaporation of fluid samples or reagents within the device. Additionally, in the case of other fluids, e.g., ferrofluids or oils with suspended metallic particles, application of an appropriate magnetic field at the valve position immobilizes the fluidic valve, thereby resisting fluid passage at pressures greater than 3–5 psi. Similarly, electrorheological effects may also be employed in controlling these fluidic valves. For example, the oil portion of the fluid valve may have suspended therein appropriate particles having high dielectric constants. Application of an appropriate electric field then increases the viscosity of the fluid thereby creating an appropriate barrier to fluid flow.

The device may also incorporate one or more filters for removing cell debris and protein solids from the sample. The filters may generally be within the apparatus, e.g., within the fluid passages leading from the sample preparation/extraction chamber. A variety of well known filter media may be incorporated into the device, including, e.g., cellulose, nitrocellulose, polysulfone, nylon, vinyl/acrylic copolymers, glass fiber, polyvinylchloride, and the like. Alternatively, the filter may be a structure fabricated into the device similar to that described in U.S. Pat. No. 5,304,487 to Wilding et al., previously incorporated herein. Similarly, separation chambers having a separation media, e.g., ion exchange resin, affinity resin or the like, may be included within the device to eliminate contaminating proteins, etc.

In addition to sensors for monitoring temperature, the device of the present invention may also contain one or more sensors within the device itself to monitor the progress of one or more of the operations of the device. For example, optical sensors and pressure sensors may be incorporated into one or more reaction chambers to monitor the progress of the various reactions, or within flow channels to monitor the progress of fluids or detect characteristics of the fluids, e.g., pH, temperature, fluorescence and the like.

As described previously, reagents used in each operation integrated within the device may be exogenously introduced into the device, e.g., through sealable openings in each respective chamber. However, in preferred aspects, these reagents will be predisposed within the device. For example, these reagents may be disposed within the reaction chamber which performs the operation for which the reagent will be used, or within the fluid channels leading to that reaction chamber. Alternatively, the reagents may be disposed within storage chambers adjacent to and fluidly connected to their respective reaction chambers, whereby the reagents can be readily transported to the appropriate chamber as needed. For example, the amplification chamber will typically have the appropriate reagents for carrying out the amplification reaction, e.g., primer probe sequences, deoxynucleoside triphosphates ("dNTPs"), nucleic acid polymerases, buffering agents and the like, predisposed within the amplification chamber. Similarly, sample stabilization reagents will typically be predisposed within the sample collection chamber.

2. Generic Sample Preparation Device

Figure 12:
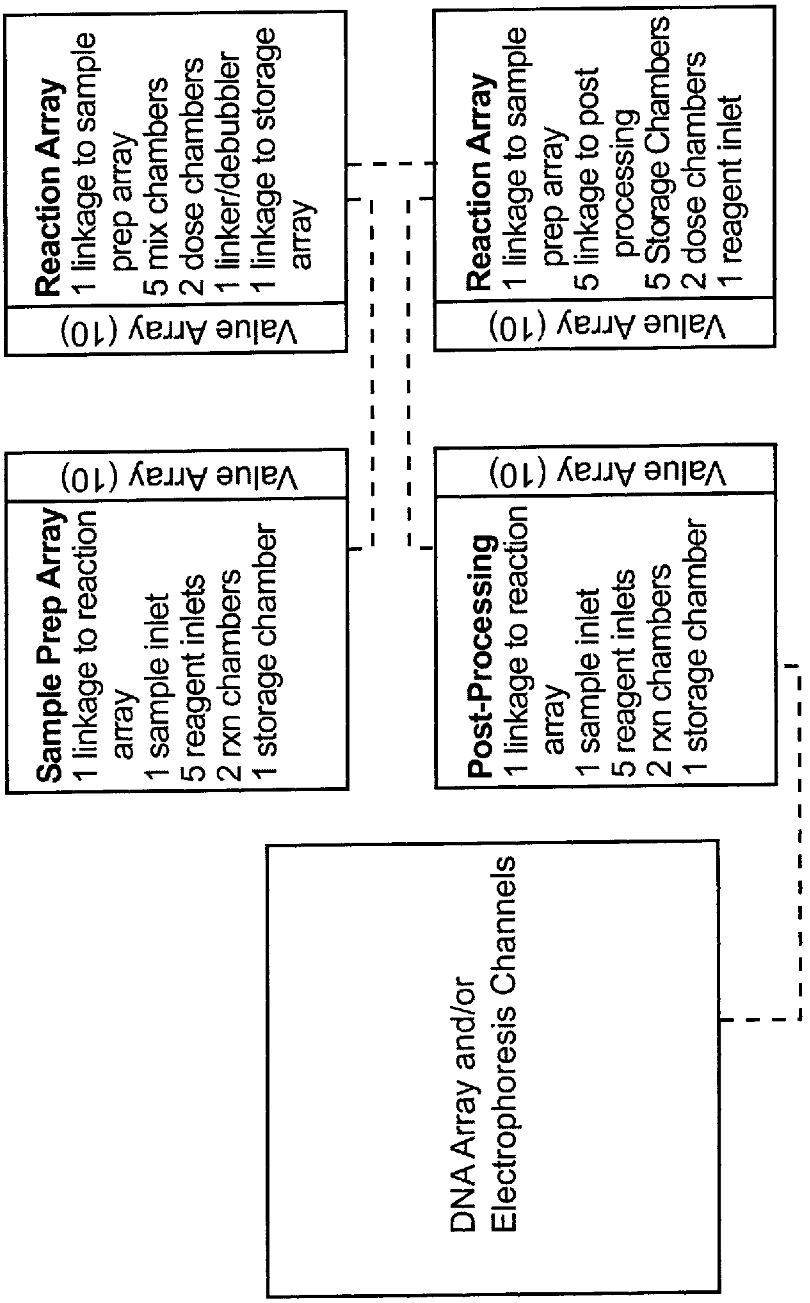
FIG. 12 is a schematic representation of a device configuration for carrying generic sample preparation reactions.

FIG. 12 shows a schematic illustration of a device configuration for performing sample preparation reactions, generally, utilizing the fluid direction systems described herein, e.g., employing external pressures, hydrophobic vents and pneumatic valves. In the configuration shown, four domains of the device are each addressed by an array of valves, e.g., a valve array, with its own common channel. The four domains may generally be defined as: (1) reagent storage; (2) reaction; (3) sample preparation; and (4) post processing, which are fluidically interconnected. The sample preparation domain is typically used to extract and purify nucleic acids from a sample. As shown, included in the sample preparation domain are 5 reagent inlets that are fluidly connected to larger volume storage vessels, e.g., within the base unit. Examples of such reagents for extraction reactions may include, e.g., 4M guanidine isothiocyanate, 1×TBE and 50:50 EtOH:$H_2O$. The two reaction chambers may include, e.g., affinity media for purification of nucleic acids such as glass wool, or beads coated with poly-T oligonucleotides.

The storage domain is linked to the sample preparation domain, and is used for storage of reagents and mixtures, e.g., PCR mix with FITC-dGTP and dUTP but no template, UNG reaction mix and IVT reaction mix without template. The reaction domain is also linked to the sample preparation domain as well as the storage domain and includes a number of reaction chambers (5), measuring chambers (2) and debubbling chambers (1). Both sample preparation and reaction domains may be addressed by a thermal controller, e.g., heaters or thermoelectric heater/cooler.

The post processing domain is typically linked to the reaction domain and includes a number of reagent inlets (5), reaction chambers (2), storage chambers (1) and sample inlets (1). The reagent inlets may be used to introduce buffers, e.g., 6×SSPE or water into the analytical element, e.g., an oligonucleotide array.

3. Generic Multiple Parallel System

Figure 13:
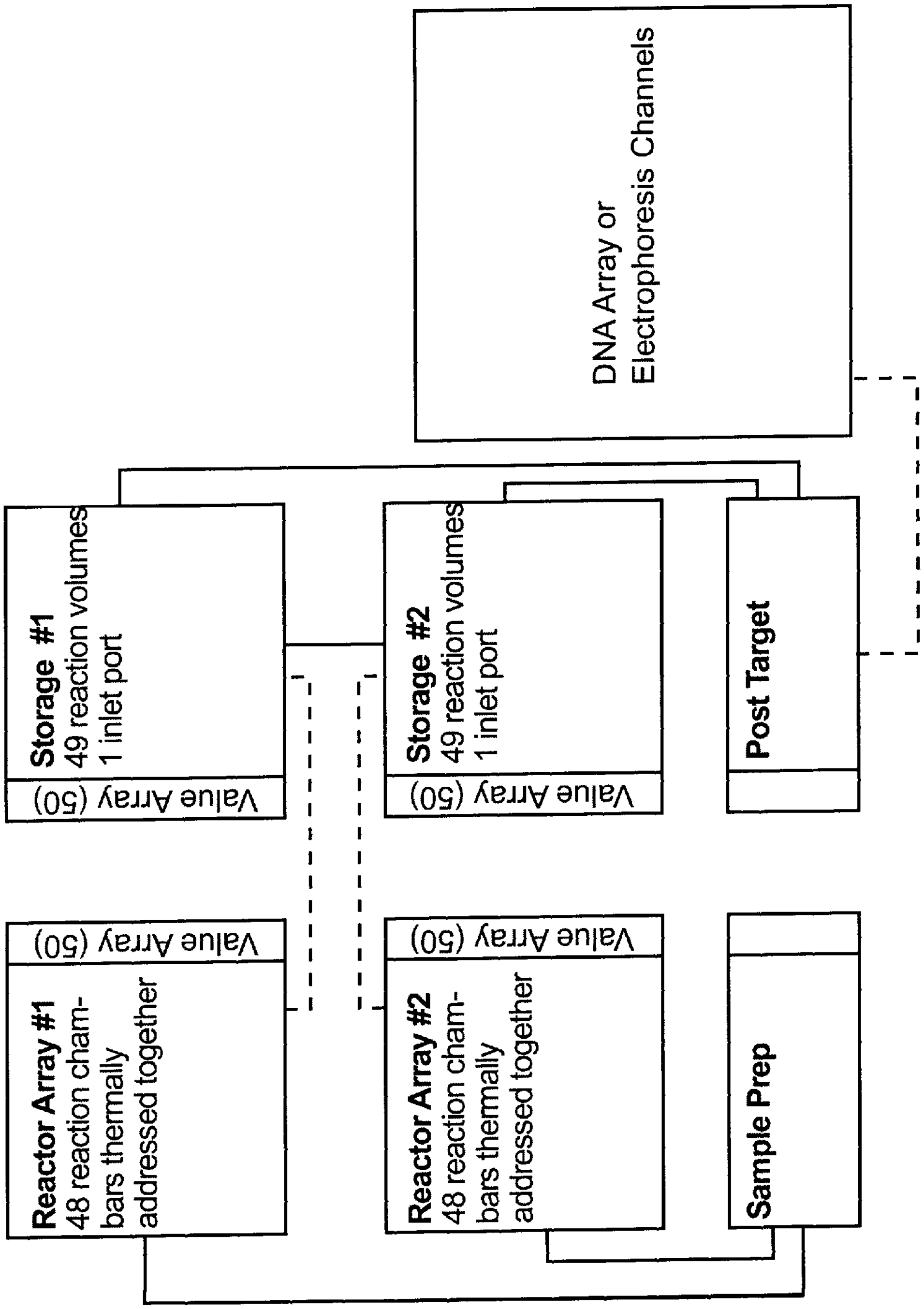
FIG. 13 is a schematic representation of a device configuration for carrying out multiple parallel reactions.

FIG. 13 is a schematic illustration of a device configuration for addressing situations where several reactions are to be carried out under the same thermal conditions, e.g., multiple parallel sample analyses, duplicating multiplex PCR by carrying out several PCR reactions with single primer pairs in parallel followed by recombining them, or cycle sequencing with a variety of primer pairs and/or templates.

In this configuration as shown, two storage domains supply reagents to two reaction domains, each being addressed by an array of 50 valves. The reaction and storage arrays each comprise a 4×12 matrix of reactors/chambers, each from 10 nl to 5 $\mu$l in volume. These chambers are addressed by 4 columns each of pneumatic ports. Two additional arrays of 10 valves address a sample preparation and post processing domain. A bank of solenoid valves may be used to drive the pneumatic ports and the valve arrays or alternatively, a pneumatic memory could be used as set forth as described in "Latched Valve Manifords for Efficient Control of Pneumatically Actuated Valve Arrays", Pan et al., *Transducers* '97, IEEE.

4. Nucleic Acid Extraction Devices

Figure 15:
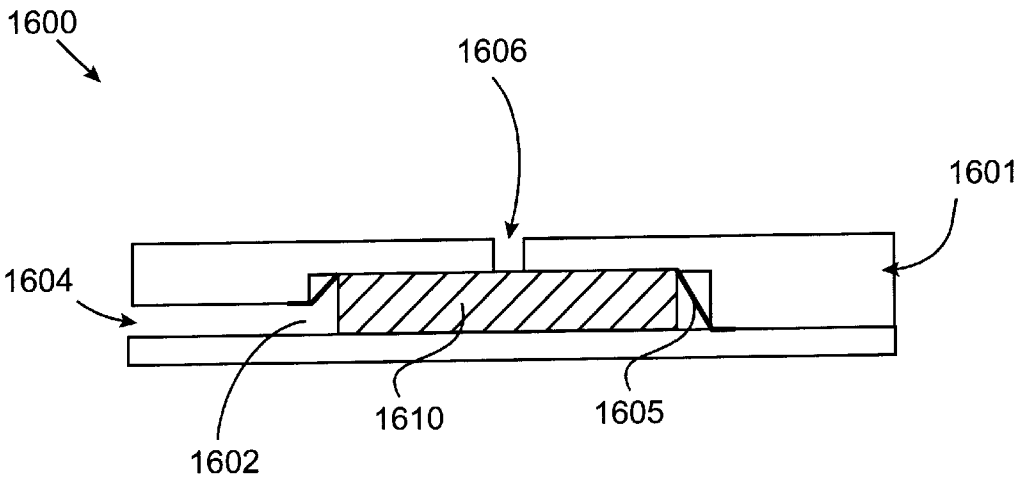
FIG. 15 schematically illustrates a deformable high capacity nucleic acid extraction device incorporating a porous material for extracting nucleic acids from samples.

FIG. 15 is a schematic illustration of a miniaturized nucleic acid extraction device for use with a genetic analysis system according to the present invention. The genetic analysis system may be useful for point-of-care diagnostics, forensic identification, large-scale clinical testing and other applications. Such a system is capable of accepting a patient sample such as blood, urine, spitum, or a cheek-swab suspension. In the past, the extraction of nucleic acids from these types of samples was typically carried out on a bench scale in a series of laborious steps. Some of the most complex procedures are those used to separate the nucleic acids from the lysed mixture. For example, messenger RNA comprises only a small fraction (–20%) of the total cell RNA. Purification of m-RNA would be of interest for messenger expression monitoring applications.

Figure 16:
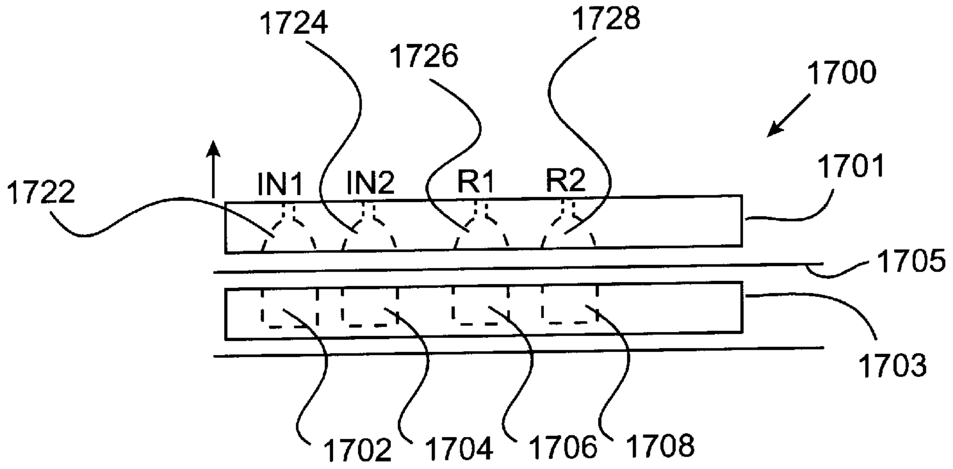
FIG. 16 is a side sectional view of a miniaturized reactor device incorporating a positive displacement fluid movement scheme.

As is set forth herein and also in Applicant's co-pending U.S. patent application Ser. Nos. 60/043,490, 08/671,928, now U.S. Pat. No. 5,922,591, U.S. Ser. No. 60/000,703, 60/000,859, and U.S. Pat. No. 5,856,174, which are incorporated herein by reference, miniaturized chambers with either glass walls (for total nucleic acid) or walls with poly-T oligo (for eukaryotic mRNA extraction) have been described. As the surface area is increased (e.g., by roughening the glass surface or by introducing glass wool), fluidic control can become difficult. FIG. 16 illustrates a structure for overcoming this difficulty. More, generally, however, the apparatus shown in FIG. 15 can be used to separate out selected portions of biological samples.

As shown, nucleic acid device 1600 comprises a base 1601 comprising a polymeric material such as polycarbonate. Base 1601 defines one or more chambers 1602, each having one or more inlet/outer channels 1604 and one or more pneumatically addressable ports 1606. A flexible diaphragm 1605, such as silicone, is introduced into the chamber 1602 and stretched across each pneumatic port 1606. The chamber may further include a hydrophobic vent, as described in detail above. The chamber 1602 is filled with a deformable porous material 1610 such as glass wool or open-cell foam. The glass wool can be used in its native condition for total nucleic acid binding or functionalized for nucleic acid binding, as set forth herein with poly-T oligos for mRNA extraction.

In use with the present invention, the porous material 1610 is first compressed by pressurizing through the pneumatic port 1606. In one embodiment, lysate is then drawn into the chamber 1602 by pulling a vacuum through the pneumatic port and flexing the diaphragm 1608 upwards. Alternatively, lysate may be flowed through porous material. After allowing sufficient time for extraction, the lysate is expelled by again applying pressure through the pneumatic port 1606. Wash and elutant solutions can be subsequently drawn into- and expelled from- the chamber by controlling the pneumatic port pressure. This design overcomes the problems of limited binding capacity with planar glass systems, and the fluidic problems encountered with high surface area packed systems.

The glass wool may be silated and linked to poly-T oligos for message capture, or pretreated with acid, base, silanes, or other material having nucleic acid binding properties such as silane, polysine, tethered antibodies, or poly-T DNA, to enhance its NA binding properties.

FIG. 18 is a schematic illustration of a miniaturized biological sample refinement device for use with a genetic analysis system according to the present invention. It would be desirable to extract nucleic acids from a subset of the cells or other particles in the initial sample. One way to do this is to reduce the sample's complexity by sorting the cells before lysis.

As shown in FIG. 18, biological sample refinement device 1900 comprises a base or cartridge 1901 made of a polymeric material such as polycarbonate (e.g. by injection molding), glass, silicon, etc. Base 1901 defines at least one chamber 1902 with one or more channels 1904. At least one wall 1906 of the chamber 1902 is textured to increase its surface area. In the example shown in FIG. 18, the wall 1906 includes a number of protrusions 1908 extending therefrom that form a number of recessed areas 1910 that increase the surface area of wall 1906. However, it will be understood that a variety of configurations are possible. For example, the wall 1906 may have a plurality of beads or particles (not shown), e.g., CTG, cellulose, or zeolite, adhesively attached thereto.

The textured wall 1906 (or beads) has binding agents 1912 thereto for attracting certain portions of a sample. In one embodiment, the binding agents 1912 bind to the corresponding cell receptors in the sample. In other embodiments, the binding agents 1912 may comprise oligonucleotides and/or organic or inorganic molecules, such as drugs or drug targets. In an exemplary embodiment, lymphocytes in whole blood are selected using antibodies such as one for the CD3 receptor.

In use, a sample such as whole blood is introduced into the chamber 1902 through an inlet channel 1920 under conditions so that the antibodies 1912 bind to the corresponding cell receptors within the sample. The chamber is washed while the cells remain attached, and then the cells are lysed by the introduction of a lysing agent, such as chaotropic salt. Alternatively, the cells may be lysed by heating them in a hypotonic solution, or adding an enzymatic lysing agent such as protenese K. The lysed cells are then drawn from chamber 1902 through inlet channel 1920 or a second outlet channel 1922. Extraction of the total nucleic acid from this lysate is carried out in a subsequent chamber, as discussed above in reference to FIG. 15. Alternatively, the nucleic acid extraction and subsequent amplification (i.e., PCR) may be performed in-situ within chamber 1902. Temperatures for affinity, washing, and lysis are controlled using a heating element (not shown) pressed against one wall of the cartridge 1901.

Figure 26:
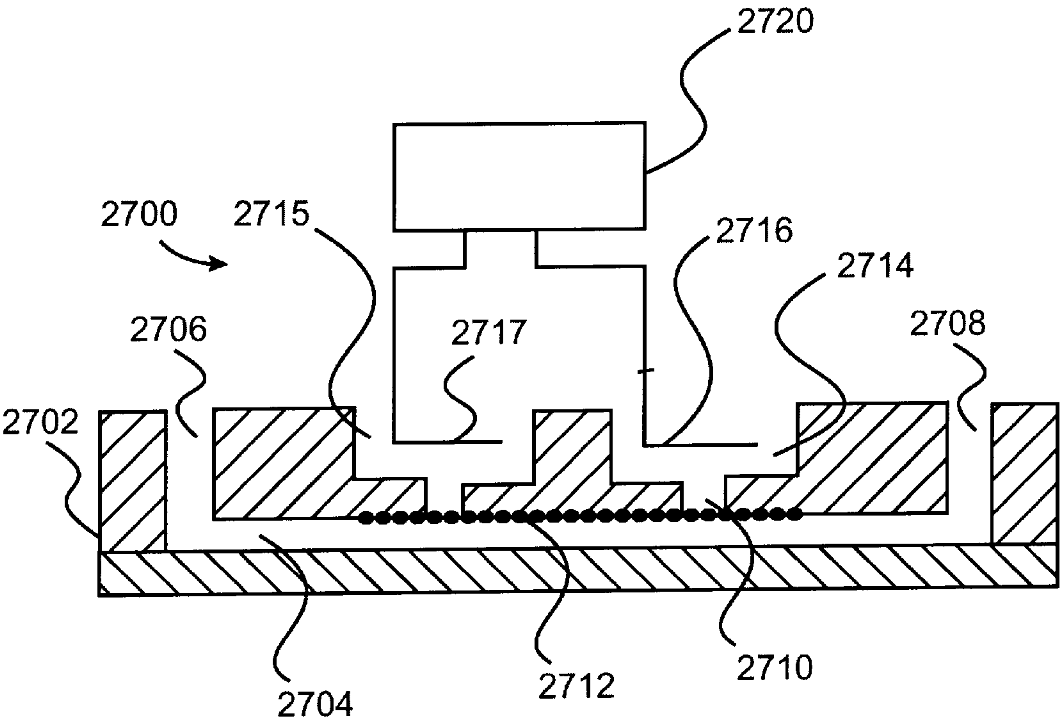
FIG. 26 is a cross-sectional view of an electrically controlled nucleic acid purification chamber.

In another embodiment shown in FIG. 26, nucleic acids are moved selectively in an applied electric field owing to their strong negative charge. These moving nucleic acids are captured on a barrier, e.g. a nanoporous material or dialysis membrane, by directing the field through this material. After capture, the cell debris and other undesirable material can be washed away. This process can be repeated to enhance purification.

As shown in FIG. 26, a nucleotide separation system 2700 includes a base 2702 defining a purification chamber 2704 with an inlet 2706, outlet 2708 and a plurality of "field" channels 2710. System 2700 further includes a barrier 2712 (e.g. a dialysis membrane), which blocks each of the field channels 2710 to create at least two electrolysis chambers 2714, 2715. Positive and negative platinum wire electrodes 2716, 2717 provided in electrolysis chambers 2714, 2715, respectively. Electrodes 2716, 2717 are each coupled to a voltage source 2720 for applying a potential between the electrolysis chambers.

In use, a lysed sample is introduced into purification chamber 2704 via inlet 2706. The voltage source 2720 is energized causing migration of the DNA and RNA of the lysed sample towards the positive electrode 2716. After sufficient time has passed (possibly with the assistance of convection), most of the DNA will be trapped on barrier 2712, which blocks the positively charged electrolysis chamber 2714. The remaining sample is then washed away with a buffer. Then, the voltage source 2720 is reversed driving the nucleotides to the other dialysis membrane blocking the negatively charged electrolysis chamber. After sufficient time and convection, the chamber is flushed. This procedure may be repeated for enhanced purification. The purified nucleotides are then released into a buffer solution by turning the voltage source 2720 off.

Alternatively, the barrier may comprise a dense gel or ultrafiltration filters. Base 2702 may comprise a polymer material such as acrylic or polyimide, or a silicon or glass material. Convection may be enhanced using pulse flow or acoustic agitation. The barrier or dialysis membrane may be placed on opposite sides of the channel and a coarse filter or gel may be placed over the membranes, or in the chamber, to reduce fouling.

In another embodiment of the present invention, a miniaturized m-RNA purification system and method are disclosed. Since messenger RNA comprises only a small fraction (e.g., about 20%) of the total cell RNA, it would be desirable to purify m-RNA from messenger expression monitoring applications. Messenger RNA can be distinguished by its poly-A tail. In this device, poly-T oligos are tethered on a high surface geometry. The messenger RNA will selectively hybridize to these oligonucleotides.

Figure 27:
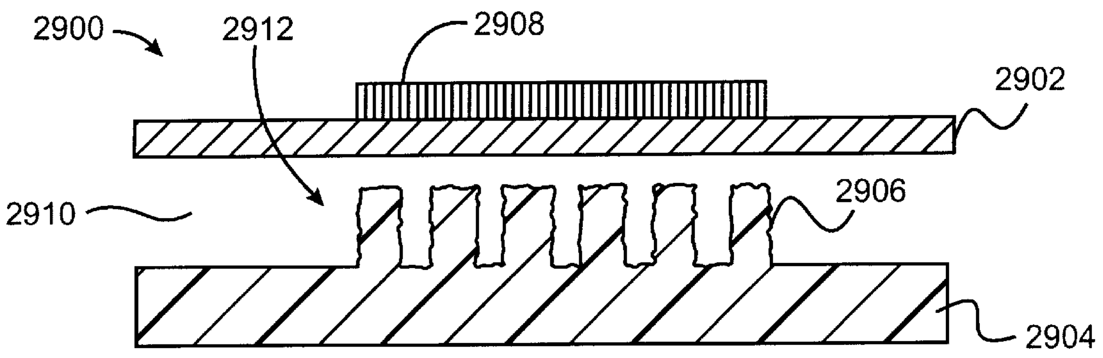
FIG. 27 is a cross-sectional view of a miniaturized m-RNA purification system.

Referring to FIG. 27, a messenger RNA purification system 2900 includes a sheet 2902, such as polycarbonate, glass, silicon, or polypropelene, polystyrene, polyethylene, acrylic, and commercial polymers, and a substrate 2904 (e.g., silicon) having a plurality of ridges 2906 between the sheet 2902 and substrate 2904. Preferably, sheet 2902 is a polymer and substrate 2904 is silicon, but such composition is not limiting as other workable compositions are equally possible. The ridges 2906 are preferably formed using reactive ion etching or other conventional techniques. Poly T oligos or other affinity treatment 2912 are attached to ridges 2906, as discussed below. A piezoelectric crystal 2908 is preferably mounted to the polymeric sheet 2902 opposite substrate 2904.

In use with the present invention, the polymeric sheet 2902 forms a reaction chamber 2910 between its lower surface and ridges 2906 of the silicon substrate. Poly-T oligonucleotides 2912 are tethered to the silicon surface by oxidation, silation and standard DMT chemistry. The piezoelectric crystal 2908 is used to enhance hybridization through acoustic streaming. A filtered nucleic acid containing solution is mixed with salt (e.g., 6×SSPE) to increase the ionic strength for hybridization. The salted sample is introduced into chamber 2910. After sufficient time has elapsed for hybridization, the chamber is washed with a clean salt solution, preferably at an elevated temperature. The m-RNA is removed using a weak buffer (or DI water). More, generally, however, the apparatus shown in FIG. 27 can be used to separate out selected portions of biological samples.

In an alternative embodiment, the oligonucleotides may be synthesized directly using either DMT or light activated phosphoramidites, or pre-synthesized oligonucleotides tethered to the surface using streptavidin/avidin coupling or thiol binding to gold. Although the high surface area is preferably formed by ridges 2906, it will be recognized that this high surface area may be formed by a variety of techniques, for example, the high surface area zone may comprise porous silicon, zeolite, RIE etched pillars, silica xerogel, etched glass, sintered particles, glass spheres or other particles.

Figure 28:
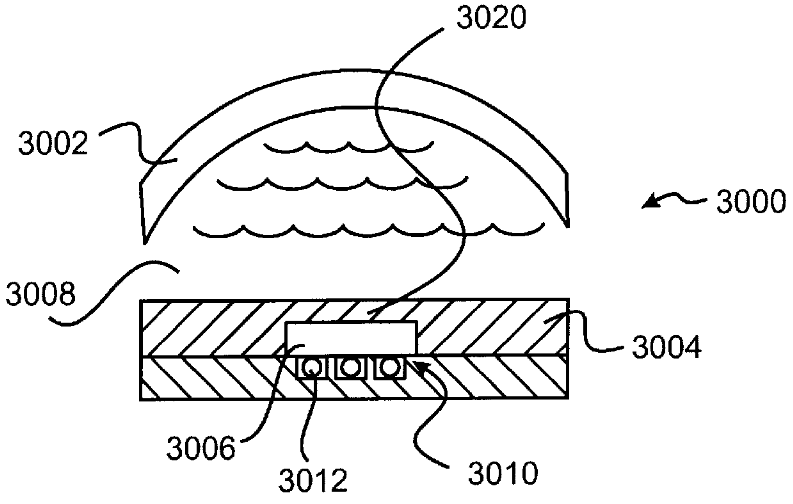
FIG. 28 is a sectional view of a cell lysis or nucleic acid fragmentization system incorporating acoustic energy.

Another embodiment for controlling the degree of lysis to select DNA and RNA from plasma, cytoplasma, or nucleus will now be described. In this embodiment, (shown in FIG. 28), a focused acoustic source, such as a piezoelectric crystal 3002 (preferably a lead-zirconium-titanate or lithium niobate piezoelectric ceramic in a focused shape) is coupled to a thinned wall 3020 of a polymeric base 3004 via a fluid filled balloon 3008. An injected molded chamber 3006 within base 3004 includes a plurality of grooves 3010 on a lower surface for enhancing the lysing effect. Alternatively, the channel wall may be shaped with pits, spikes or other structures and textures such as can be made on a glass, silicon, polycarbonate, polypropelene, polystyrene, polyethylene, acrylic, or commercial polymer such as Kapton, Valox, Teflon, ABS, Delrin and the like structure.

In use, piezoelectric ceramic crystal 3002 generates acoustic energy that is directed into chamber 3006. The cell suspension is introduced into chamber 3006 and the cells 3012 segregate into grooves on the lower surface of the chamber. When crystal 3002 is activated, a high shear rate is created in the grooves causing the cells to lyse. Regions of high fluidic shear rate, high pressure, and possibly cavitation are created by the interaction of the acoustic energy with the groove 3010 geometry. The acoustic energy may be operated at frequencies from 100 kHz to 5 Mhz. In addition, it should be noted that the thinned region 3004 may be replaced with adhesive tape or other thin film.

5. Electronically Controlled pH System

In addition to extracting the nucleic acids in a miniaturized genetic analysis system, it would also be desirable to control the degree of lysis in order to select a DNA or RNA source from within a mixture (e.g., plasma, cytoplasma or nucleus). In another embodiment of the present invention, a miniaturized device is provided for lysing cells using electrically controlled pH. In this method, an electrode is generally positioned near a reaction chamber while a counter electrode is located in a second chamber communicating with the reaction chamber. When current is passed between these two electrodes, the pH in the reaction chamber is altered through the electrolysis of water. A pH sensor is positioned within the reaction chamber so that feedback control can be used to control the chamber pH.

In an alternative aspect of the present invention, the device may include an electronically controlled pH system. In operation, an electrode is placed adjacent, e.g., in fluid contact, to a reaction chamber while a counter electrode is positioned within a second chamber or channel fluidly connected to the first. Upon application of current to these electrodes, the pH of the reaction chamber is altered through the electrolysis of water at the surface of the electrode, producing $O_2$ and hydrogen. A pH sensor may also be included within the reaction chamber to provide for monitoring and/or feedback control of the precise pH within the chamber.

Figure 10:
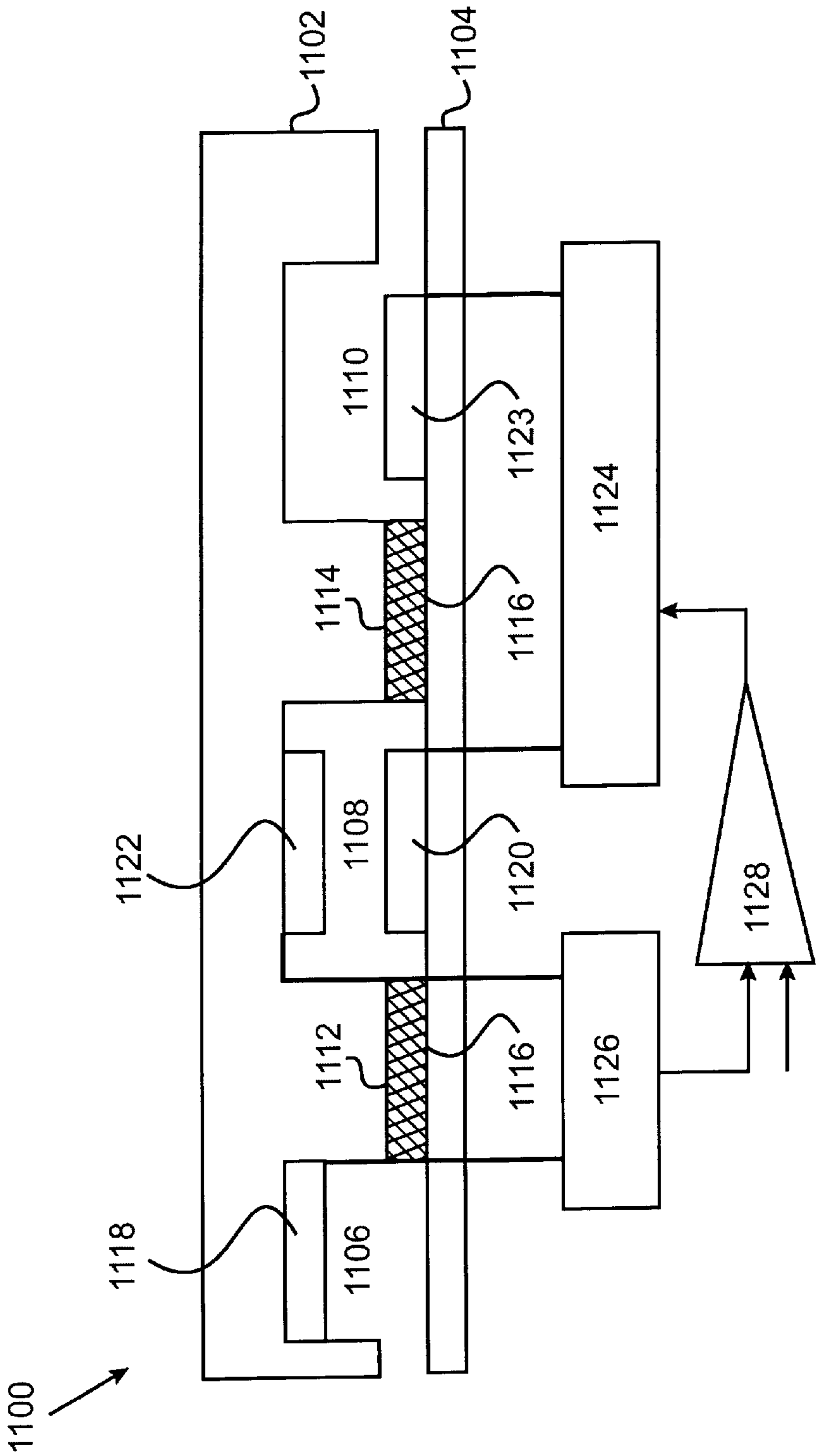
FIG. 10 shows an embodiment of a reaction chamber employing an electronic pH control system.

One example of a reaction chamber which can be used for cell lysis employing an electronic pH control system is shown in FIG. 10. As shown, a device 1100 fabricated from two planar members 1102 and 1104, includes three distinct chambers, a reference chamber 1106, a reaction chamber 1108, and a counter-electrode chamber 1110. Each of the reference chamber 1106 and counter-electrode chamber 1110 are fluidly connected to the reaction chamber 1108, e.g., via fluid passages 1112 and 1114. These passages are typically blocked by an appropriate barrier 1116, e.g., dialysis membrane, gel plug such as a polyacrylamide gel, or the like, to prevent the electrophoretic passage of sample elements between the chambers, and to minimize flow of fluid. Such restrictions are known to ones skilled in the art and include optimization of critical dimensions and the use of porous plugs.

The reference chamber 1106 typically includes a reference electrode 1118. The reference electrode may be fabricated, e.g., from a platinum, gold, nickel, or silver screen so that a reproduceable electrochemical function is formed. Examples include a platinum screen pressed with a mixture of Teflon and platinum black (producing a hydrogen electrode), and a silver wire or screen in a chloride containing buffer producing an $AgCl_2/Ag$ electrode. The reaction chamber 1108 typically includes an electrolysis electrode 1120, e.g., a platinum, gold, nickel or carbon screen, optionally coated with an appropriate barrier, e.g., polyacrylamide gel layer, and a hydrogen electrode 1122 (as described above), also protected with an appropriate barrier. The reference electrode 1118 and hydrogen electrode 1122 are connected to an electrometer 1126 for monitoring the pH within the reaction chamber. The counter-electrode chamber 1110 typically includes the counter-electrode 1123, e.g., a single platinum, gold or nickel screen electrode. The electrolysis electrode and counter-electrode are connected to an appropriate current source 1124.

In use, a cell suspension is introduced into reaction chamber 1108 and a current source 1124 is energized to thereby begin to alter the pH in reaction chamber 1108 by electrolysis. An electrometer 1126 compares the pH sensed by the voltage between reference electrode 1108 in reference chamber 1106 and hydrogen electrode 1122 in reaction chamber 1108. In an additional embodiment, the signal from electrometer 1126 is compared with a setpoint in a comparator 1128 and used to control current source 1124. The resulting system provides control of the reaction chamber pH by varying the setpoint signal. The reaction chamber can be cycled between acidic and basic conditions as desired, to create cell lysis, protein or nucleic acid denaturation, nucleic acid fragmentation, or enzyme deactivation. Alternatively, the system may be used to fragment DNA, RNA or to kill enzymes.

The pH sensor may be a fluorescent dye that is pH sensitive. In this embodiment, pH detection is carried out using a laser and photodiode or CCD. Alternatively, the pH sensor may be an ISFET or a LAPS device such as described in *The Light Addressable Potentimetric Sensor—Principles and Applications;* Owicki et. al., Annual Review of Biophysics and Biomolecular Structure, 1994, V23:87–113.; *Biosensors For Detection of Enzymes Immobilized in Microvolume Reaction Chambers,* Sensors and Actuators B-Chemical, 1990 Jan, V1 N1-6:555–560., Published PCT Applications WO94/03791 to Crawford et. al., WO 90/04645 to Humphries et. al.; U.S. Pat. Nos. 5,395,503, 4,911,794 and 4,15812 to Parce et. al.; U.S. Pat. Nos. 4,849,330 and 4,704,353 and 4,883,579 to Humphries et. al.; U.S. Pat. Nos. 4,758,786, 4,591,550, 4,963,815 and 5,164,319 to Hafeman et. al.; U.S. Pat. No. 4,490,216 to McConnell and Austrialian Patent No. 8825745 to Bousse et. al.

Device 1100 is preferably fabricated from silicon, glass, polycarbonate, polypropelene or other useful polymers as apparent to those skilled in the art. The electrodes are preferably fabricated from sputtered metal, such as gold, platinum, nickel or from conductive polymers.

In other embodiments, electrometer 1126 compares the pH sensed by the voltage between the reference and hydrogen electrodes. This signal is then compared to a set-point by appropriate means, e.g., an appropriately programmed computer or other microprocessor, and used to control the application of current. The resulting system allows the automated control of pH within the reaction chamber by varying the set-point signal.

In other embodiments, reference electrode 1106 is placed in either reaction chamber 1108 or counter-electrode chamber 1110 and reference chamber 1106 is eliminated.

6. Microfluidic Geometries for Linking Fluid Plugs

In this aspect of the invention, systems and methods are provided for removing bubbles and for linking together fluid plugs in microfluidic systems. Such systems and methods can be combined in the same or multiple chambers in a microfluidic device. The geometries described herein generally rely on surface tension, surface wetting properties, and gravity to act as gas-liquid separators, rather than porous membranes. Such porous membranes often are rendered ineffective when exposed to surfactants over time. In addition, these membranes typically involve the joining of two different materials, which can cause problems during thermal cycling.

Referring now to FIGS. 30–33, systems and methods for combining separate fluids in a miniature biological reactor will now be described. Current methods for mending two or more separate fluids typically involve the use of a long channel which contains venting membranes that pass gas and not fluid. By passing two separate fluids through this channel (with a vent between them), gas separating the two fluids can be expelled, thereby combining the fluids. Problems arise with this method when venting membranes get plugged with fluid and stop functioning.

Figure 30A:
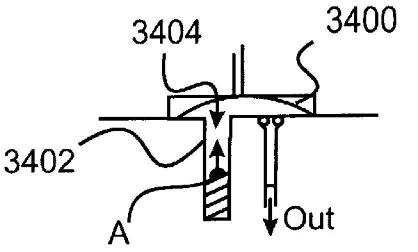
FIGS. 30A–30E illustrate a system and method for linking two fluid plugs.
Figure 30B:
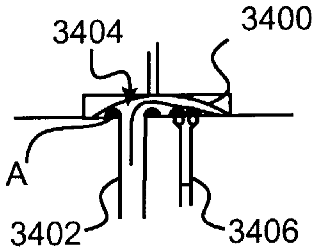
Figure 30C:
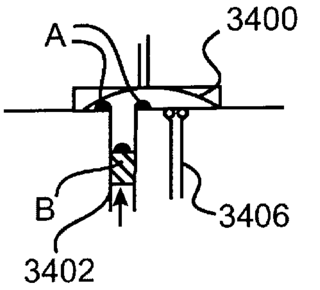
Figure 30D:
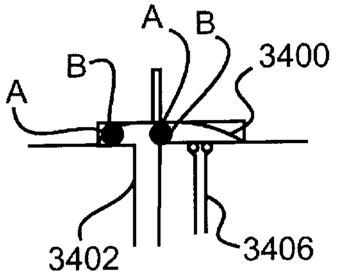
Figure 30E:
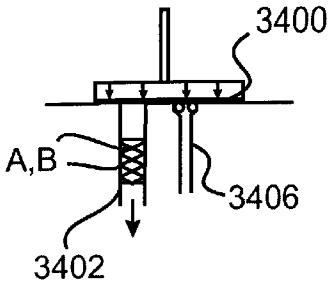
Figure 31A:
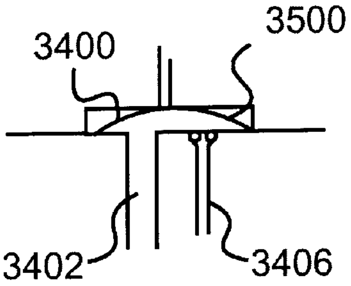
FIGS. 31A and 31B illustrate alternative embodiments of the system of FIGS. 30A–30E.
Figure 31B:
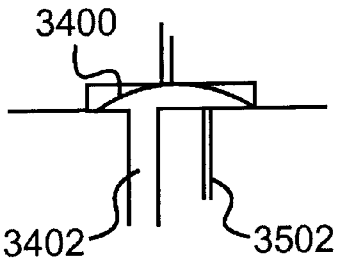

Referring to FIGS. 30A–30E, one embodiment of the present invention for combining two separate fluids will now be described. As shown in FIG. 30A, a vacuum is applied to pull up a flexible valve membrane 3400 and to pull a fluid plug A through a fluid passage 3402 to the edges of an opening 3404 below the membrane 3400. As shown in FIG. 30B, air continuously passes through a vent 3406 in the chamber leaving the fluid plug A behind. As shown in FIG. 30C, fluid B is then pushed through fluid passage 3402 where it combines with fluid A on the edges of opening 2404 (FIG. 30D). Pressure upon flexible valve member 3400 then causes the valve member to reduce the chamber volume to zero (FIG. 30E). The combined fluids A plus B are then expelled back downward through fluid passage 3402.

Figure 34:
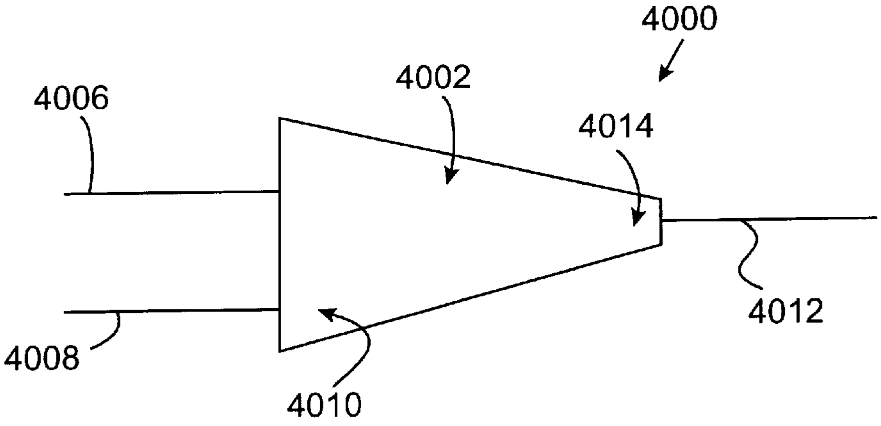
FIG. 34 illustrates a tapered chamber for linking fluid plugs with surface tension.

Referring now to FIG. 34, a fluid-gas separation system 4000 includes a chamber 4002 having a generally tear drop shape that tapers at one end. As shown, a pair of passages 4006, 4008 are coupled to an expanded end 4010 of chamber 4002 and a single passage 4012 is coupled to a tapered end 4014 opposite expanded end 4010. Of course, other geometries can be envisioned in this embodiment of the invention, such as multiple passages on either side of chamber 4002 or only single passages on either side. Liquid surface tension will tend to draw the liquid to the tapered end 4014 of chamber 4002.

Fluid-gas separation system 4000 can be operated in several modes. In a first dead-end mode, passage 4008 is not necessary (either absent or plugged) and passage 4006 comprises a dead-end ballast volume. Liquid plugs and the gases separating them are introduced into chamber 4002 through passage 4012. The gases pass through to passage 4006, while the liquids collect at tapered end 4014 of chamber 4002. Linked liquid can then be removed from the chamber by lowering the pressure at passage 4012.

In a second flow-by mode, liquids and gases are introduced through passage 4006 and gases pass through passage 4008. The linked liquids are removed through passage 4012 by applying a differential pressure between the passages.

In a third flow-through mode, passage 4006 is either absent or plugged. In this mode, liquids and gases are introduced through passage 4012 and gases escape through passage 4008. Linked fluids are then removed through passage 4006.

When using any of these operating modes, chamber 4100 can be oriented with narrow end 4014 downwardly, so that gravity aids in the de-bubbling process.

Figure 35A:
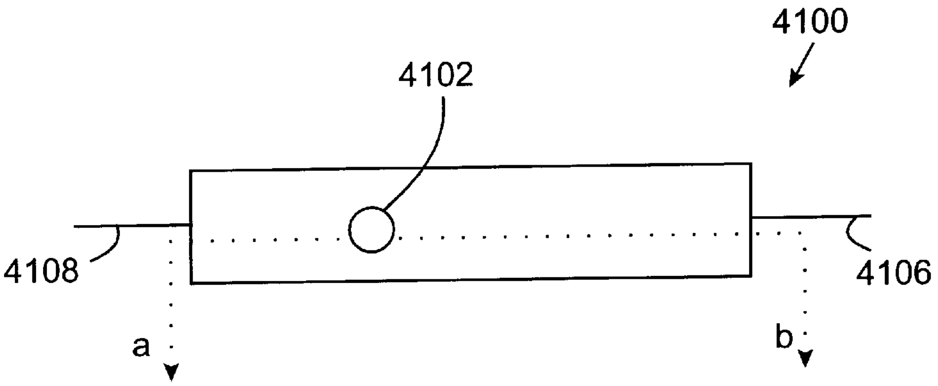
FIGS. 35A and 35B illustrate a stalactite chamber for linking fluid plugs with surface tension.
Figure 35B:
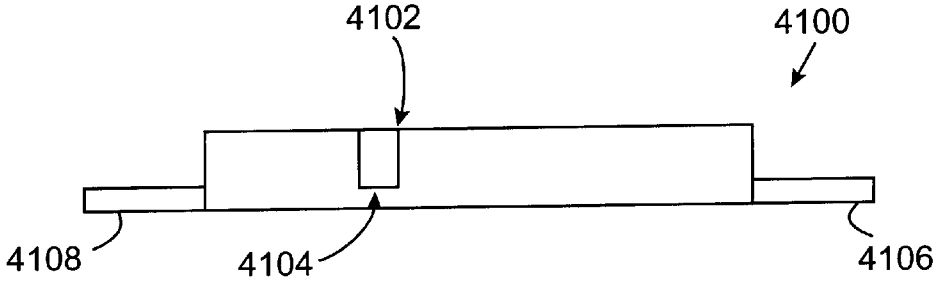
Figure 36A:
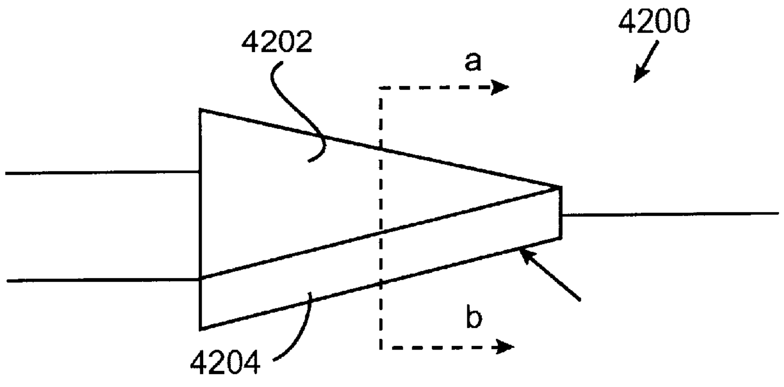
FIGS. 36A and 36B illustrate a chamber having a shallow region for linking fluid plugs with surface tension.
Figure 36B:
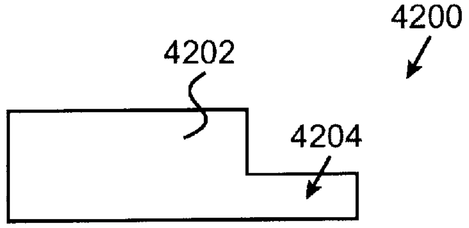

Referring now to FIGS. 35A and 35B, a stalactite chamber 4100 is provided according to the present invention for separating gases and liquids and/or for linking separate fluids. As shown, chamber 4100 includes at least one protrusion 4102 that creates a narrow region 4004 within the chamber. Liquids are introduced into chamber 4000 through one or more passages 4006 and drawn into region 4004 by surface tension. The gases pass through region 4004 into one or more outlet passages 4008. The chamber may include any number or arrangement of protrusions or other geometries that create a narrow region therein.

In another embodiment, a gas-liquid separation system 4200 includes a chamber 4204 having a shallow region 4204 or gutter that creates a narrow region within the chamber 4200. As described above, liquid are drawn into shallow region 4204 while gases flow past. The dead-end, flow-by, flow-through, and gravity-assist modes described above may be used with system 4200.

In other embodiments, gravity may be used to aid in the gas-liquid separation. In addition, the above structures may be used to collect and trap small fluid plugs that are intermittently generates by valves and dead volumes within the genetic analysis system. Alternatively, wetting properties may be controlled by surface treatments, modifications or patterned materials, e.g., plasma-based surface modification, coatings, plasma-based chemical deposition, silation, etc. The chambers and channels in these embodiments may comprise polymers, polycarbonate, polypropylene, glass, etched silicon or the like.

In another aspect of the invention, systems and methods are provided for controlling and removing gas bubbles in miniaturized liquid-handling devices, such as analysis instrumentation. Applicant has found that linker/mixing structures incorporating hydrophobic porous membranes are less than ideal for various reasons. For example, liquid plugs may remain in the conduit leading to the vent, thereby blocking the flow of gas. In addition, surfactants in some reagents coat the hydrophobic vent, rending it partially hydrophilic. As such, a film of liquid coats the vent and plugs the flow of gas therethrough.

Figure 37A:
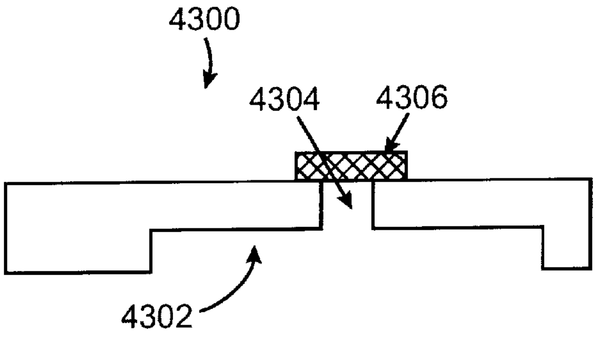
FIG. 37A illustrates a previous fluid mixing/linking structure with a vent membrane.
Figure 37B:
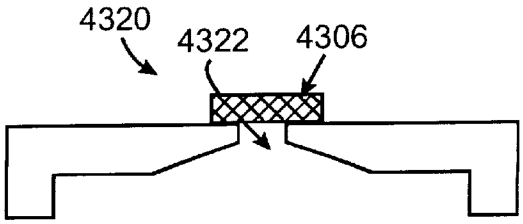
FIG. 37B illustrate the inventive fluid mixing/linking structure with a tapered channel leading to the vent membrane.

FIG. 37A illustrates a previous linker-vent structure 4300 having channel 4302 with a vent conduit 4304. A vent membrane 4306 covers vent conduit 4304. Applicant has found that the amount of liquid trapped in vent conduit 4304 decreases with the conduit length. According to the present invention, the conduit length can be minimized by forming a tapered vent structure 4320 that includes a tapered vent conduit 4322, as shown in FIG. 37B. Tapered vent conduit 4322 can be formed, for example, with a ball-end mill. Alternatively, the vent conduit may also be completely eliminated by mounting the vent material inside the channel or chamber.

Figure 38:
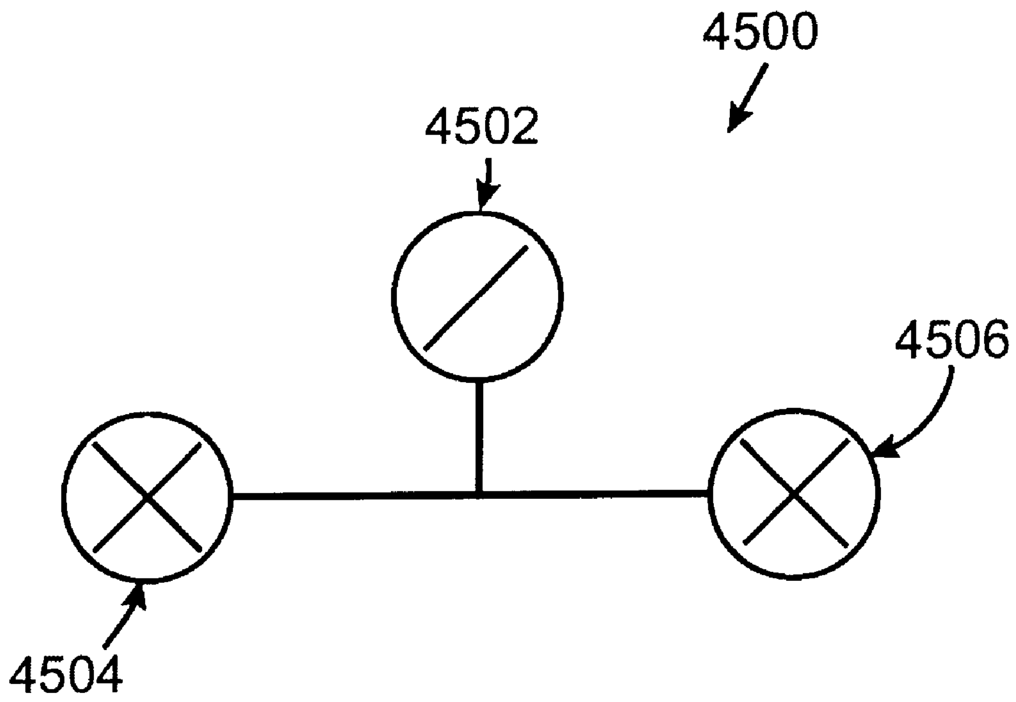
FIG. 38 illustrates the inventive T-shaped linker structure.

Another embodiment of the present invention is shown in FIG. 38. Liquids with surfactants can change the wetting properties of a vent so that a liquid film adheres to and blocks the vent. Experiments have revealed that blowing gas through the back of the vent will redistribute this liquid film and clear the vent. However, a cleared wetted vent will generally revert back to a choked wetted vent when it comes in contact with bulk liquid.

Figure 39A:
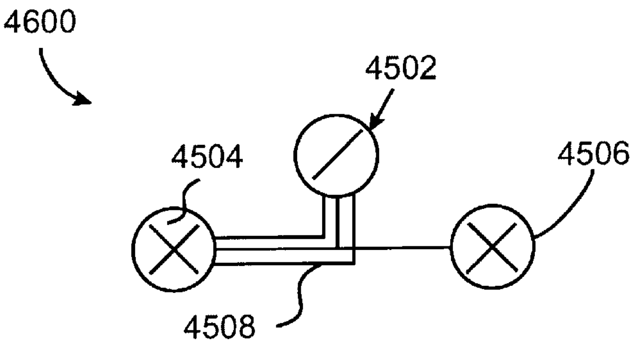
FIGS. 39A–39C illustrate a method for combining fluid plugs with the T-shaped linker structure of FIG. 38.
Figure 39B:
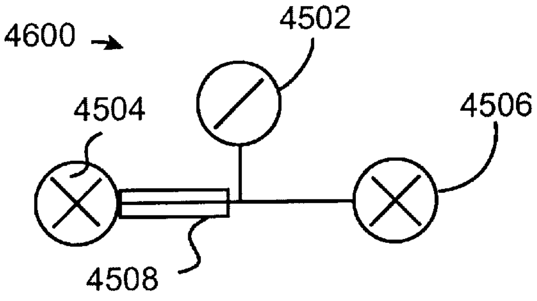
Figure 39C:
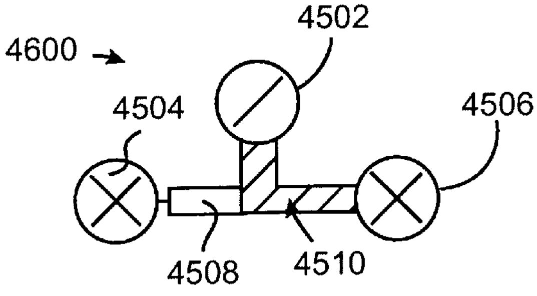

Referring again to FIG. 38, an alternative linker structure 4500 takes advantage of the above described vent behavior. As shown, linker structure 4500 comprises a vent 4502 coupled to first and second valves 4504, 4506 so as to form a T-shaped linker structure. This T-shaped linker structure can be used to link two fluid plugs. For example, a first fluid plug 4508 is introduced through valve 4504 to vent 4502, as shown in FIG. 39A. The vent is then cleared by blowing air therethrough, which expels an excess part of fluid 4508 through the second valve 4506 (FIG. 39B). A second fluid plug 4510 is then introduced through the second valve 4506 to vent 4502 to link the first and second fluid plugs 4508, 4510 (FIG. 39C). This process has been demonstrated hundreds of times without failures using mock PCR mixes, real reagents, and solutions with up to five times the amount of Tween-20.

In other embodiments, a pair of crossed channels may be used for linking (i.e., no vents). Alternatively, the vent conduit may be minimized by fabricating a thin wall, e.g., from a thin sheet of plastic, such as polycarbonate or polypropylene, bonded to the cartridge, or by adhesive tape bonding the wall to the cartridge and mounting the vent there.

7. Device and Methods for Metering Fluids

Figure 32A:
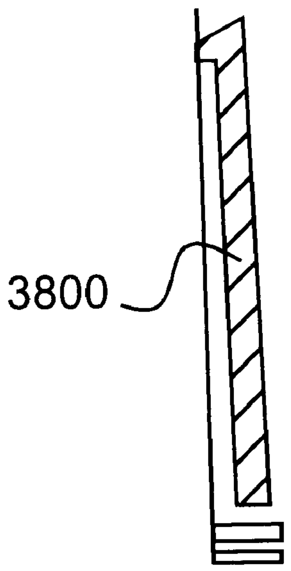
FIGS. 32A, 32B and 32C illustrate a chamber adapted for measuring or metering a variable amount of fluid.
Figure 32B:
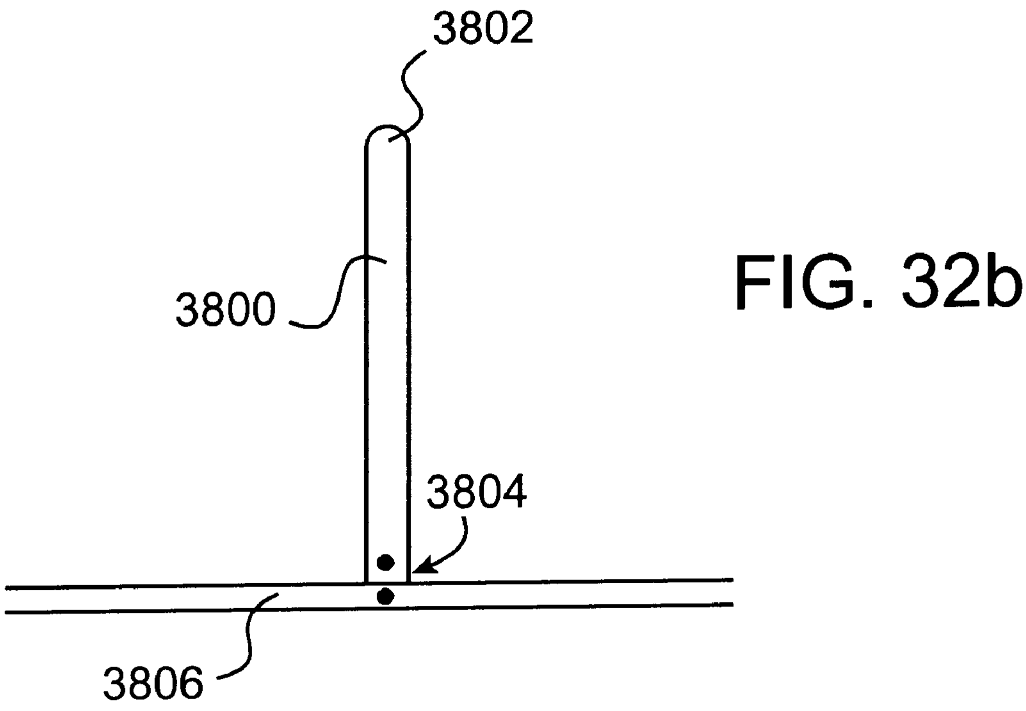

Referring to FIGS. 32 and 33, a system and method for measuring and distributing microliter volumes of fluid in biological cartridge systems will now be described. This newly proposed design generates variable microliter sized fluid plugs. As shown in FIGS. 32A and 32B, a small microliter chamber 3800 is machined out of a suitable material, such as plastic. The chamber 3800 has a ballast end 3802 and an open end 3804 with a valve coupled to a common channel 3806.

Figure 32C:
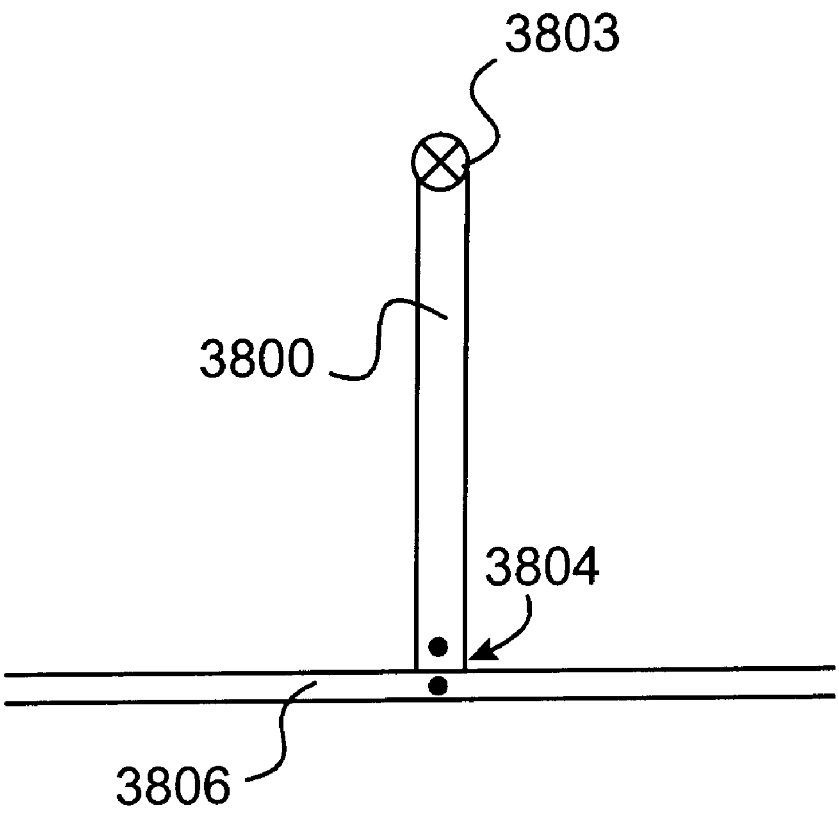
Figure 33A:
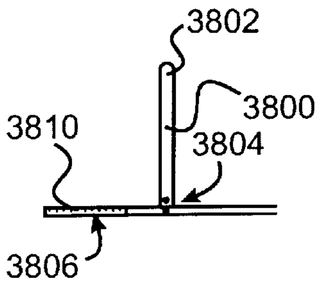
FIGS. 33A–33E illustrate a method for measuring a fluid amount with the chamber of FIGS. 32A and 32B.
Figure 33B:
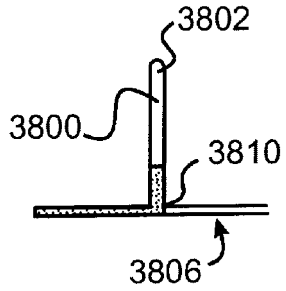
Figure 33C:
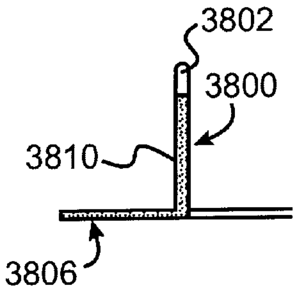
Figure 33D:
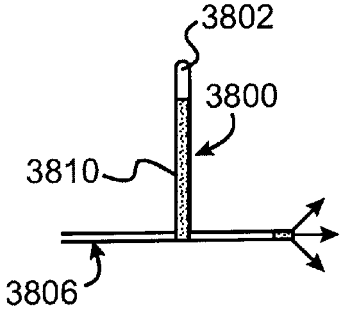
Figure 33E:
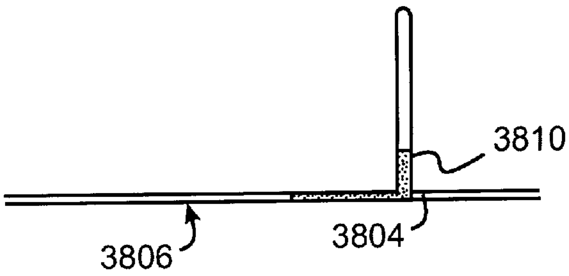

In use, a fluid plug 3810 is pushed from the common channel 3806 into the closed chamber 3800 using applied air pressure (see FIGS. 33A–B). Pressure builds as the plug 3810 moves into the chamber 3800 and the trapped gas in the closed portion is compressed by the incoming fluid (FIGS. 33B and 33C). The fluid will stop when the compressed gas is equal in pressure to the applied pressure (see FIG. 33D). The valve 3804 is closed and the common line 3806 is then blown out. By defining the relationships between input pressure chamber volume and resulting plug volume, increasing the input pressure will increase the plug volume and vice versa. By increasing or decreasing the pressure, one can vary the dose size. Opening the valve 3804 causes the plug 3810 to be expelled with the same pressure as the original input pressure (FIG. 33E). Alternatively, as is shown in FIG. 32C, a valve 3803 can be provided at the end of chamber 3800 to permit purging of chamber 3800.

8. Microdevice for Manipulating Polynucleotides

Figure 19:
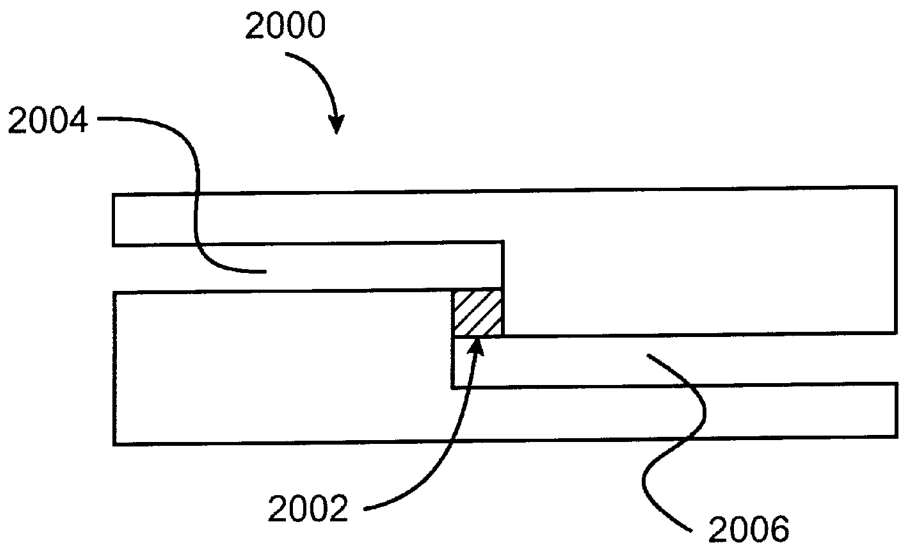
FIG. 19 illustrates an allele-specific purification device according to the present invention.

FIG. 19 schematically illustrates a microdevice 2000 for separating out selected portions of biological samples. Microdevice 2000 may be useful in a variety of applications, but is particularly useful for removing the complex genetic background in a sample, ensuring a constant concentration of DNA or RNA using molar dosing or skewing a sequence population of the mixture by melting point to improve analysis by hybridization array by reducing detection dynamic range requirements. This system can also be used for m-RNA extraction or purification.

Generally, a portion of a sample is selected by hybridization to an array of polynucleotides tethered to a solid support 2200 which may either comprise a porous plug or a binding surface disposed in an affinity chamber. Microdevice 2000 has an input channel 2004 and an output channel 2006, permitting fluid flow through support 2002. Material that is not specifically bound to the array is washed away, and then the purified nucleic acids are eluted from the support. The purification capacity of the solid support medium increases with surface area. Accordingly, a porous medium is advantageous. Sample purification applications may require a large number (e.g. more than 1000) of different well-defined allele's, necessitating use of the light-directed oligomer synthesis methods developed for GeneChip™ technology.

In a preferred embodiment, cleavable linkers are attached to a thin porous layer of polyacrylamide. Light directed synthesis is carried out with large feature sizes, e.g., 400 $\mu$M. The synthesis is terminated with biotin. Oligomers are cleaved from the porous film and purified and concentrated. Glass wool is prepared so that it contains streptavidin linkages. The purified oligomer mixture is then reacted with the glass wool.

As shown in FIG. 19, the support surface of the affinity chamber can be provided by a compressed plug 2200 of glass wool positioned between channels 2004 and 2006 in a fluidic cartridge 2000 such that fluid passing from channel 2004 to 2006, or vice versa, must pass through the plug 2002. Preferably, plug 2002 is positioned in a vertical portion of the channel as shown. In the alternative embodiment where solid support 2000 comprises a binding surface disposed in an affinity chamber, fluid is passed over this binding surface when moving through the affinity chamber.

In operation, the user (or previous processing module) injects the sample nucleic acid mixture in a low stringency buffer such as 6×SSPE. The hybridization mixture is washed back and forth through the porous plug 2002 until sufficient hybridization has taken place. The plug is washed with fresh buffer several times, and then filled with a high stringency buffer such as DI water. The purified nucleic acids are eluted into this buffer by, for example, raising the temperature to 60° C.

This device can be used to remove the complex background of a genetic sample. In a different application, DNA or RNA in a sample can be dosed (i.e., measured) by hybridizing to a set of random oligomers (e.g., hexamers at a controlled denisty) on a controlled surface area.

In a third application, it may be desirable to skew the population of a mixture of DNA or RNA target towards fragments with a low melting point. This would help to match the allowable stringencies of a mixture for hybridization-based sequence analysis. For example, a fragmented target mixture would be hybridized to a porous plug with a subset of oligo's from the analysis GeneChip™ array or random hexamers rich is A's and T's nucleotides, but with a larger number of the A-T sequences represented. This purification-probe population would be designed so that the eluted population is appropriately enriched with low-melting point fragments. When this new target mixture is hybridized to the GeneChip array, the system will provide improved discrimination.

The oligomers may be manufactured using standard DMT based oligo synthesis on CPG, standard GeneChip technology with cleavable linkers and appropriate termination or localized detritylation using electrochemical hydrolysis, either separately or directly on the porous medium.

In alternative embodiments, the oligos may be tethered to the capture medium by antibodies, sequences of RNA or DNA, or chemical bonds. The capture medium may be a porous material comprising a gel such as polyacrylamide or agarose, a zeolite, a porous silicon, a controlled-pore glass (CPG), a woven fiberglass, glass wool, magnetic beads, cellulose particles, a porous polymer gel, or a roughened polymer. Alternatively, the capture medium may be a non-porous surface, such as a GeneChip™, glass spheres, magnetic beads, micromachined glass or silicon textures/structures, roughened glass or silicon, or a polyacrylimide gel layer on glass.

The oligos may be synthesized on CPG beads with DMT chemistry. In this embodiment, the CPG beads are used directly as a separation medium. Alternatively, the nucleic acids may be moved through and eluted from the capture medium using electrophoresis.

9. System for Rapid Thermal Cycling of Microreactive Chambers

Sample preparation generally requires amplification, usually involving a thermal cycling reaction such as PCR or RT-PCR. The time consumed for this reaction can be significant, as shown below in Table 1. The first line shows some typical parameters for PCR carried out in a PE2400 machine, while the second line shows the same reaction with 10 times the thermal ramp rate (10° C./sec versus 1° C./sec) and reduced denature and anneal times. As shown in the table, significant reduction in processing time is provided by rapid thermal cycling. Also, the temperature of the reaction chamber should be uniform throughout the reactant mixture to maintain product specificity.

TABLE 1

Effect of Rapid Thermal Cycling on PCR Reaction Time

| denature (seconds) | ramp (seconds) | anneal (seconds) | ramp (seconds) | extend (seconds) | ramp (seconds) | 35 cycles (minutes) |
|---|---|---|---|---|---|---|
| 20 | 39 | 20 | 10 | 30 | 29 | 86 |
| 0 | 3.9 | 0 | 1 | 30 | 2.9 | 22 |

Miniaturization provides opportunities for enhanced uniformity and rapid cycling. Smaller reaction chambers will tend to be more isothermal and cool faster than their larger-volume counterparts. A thermal cycling device generally should meet two competing criteria: (1) maintain wall temperatures without excessive heat dissipation; and (2) have the ability to change temperature rapidly. According to the present invention, this is accomplished by providing arrays of separately addressable heaters over an insulating layer that is in contact with a cooler (e.g. thermoelectric cooler).

Figure 20:
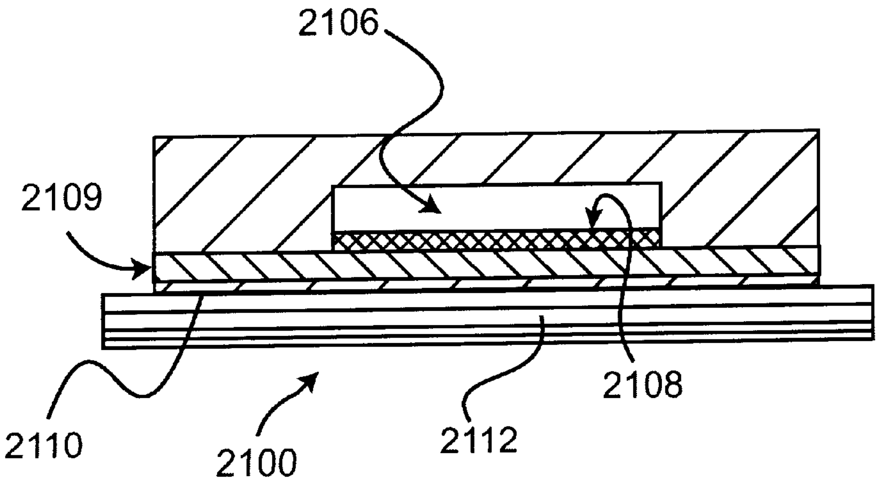
FIG. 20 is a schematic representation of a miniaturized device for performing rapid thermal cycling reactions, such as PCR or RT-PCR.

FIG. 20 is a schematic illustration of one embodiment of this principle. As shown, a cartridge 2100 includes a reaction chamber 2106 having at least one relatively thin wall 2108 on at least one side of chamber 2106. The thicknesses of the reaction chamber and walls are minimized to provide reduced thermal mass. The temperature in reaction chamber 2106 is controlled with a thin heater 2109 pressed against the thin wall 2108 of the reaction chamber 2106. The heater 2109 may comprise an inconel or NiCr alloy, carbon, platinum, nickel or their alloys. The heater 2109 may also include a temperature sensor (not shown) such as an RTD made of platinum or nickel, a thermocouple, or a heating element that functions similarly to an RTD.

A thermal insulator 2110 (e.g., a polycarbonate sheet) is placed under the heater 2109 to reduce steady state power consumption. The heater 2109 may be integrated on the cartridge 2100 or on insulator 2110. In an alternative embodiment, the insulator material may comprise a thin polymeric film, porous polymer or fabric, a porous ceramic such as porous silicon, a sintered plug, xerogel, aerogel, or a very thin layer of air. A cooler 2112 is in contact with the insulator 2110, so that the reactor can be cooled by turning OFF the heater. The cooler may comprise a large heat sink, a water core structure, a refrigerator structure, or an air cooled structure. In one embodiment, the cooler is a thermoelectric cooler.

In an exemplary embodiment, the thickness and properties of the thermal insulator 2110 are optimized to provide substantially uniform reactor temperature, rapid thermal cycling, and reasonable power consumption. In this optimization, it has been assumed that the reaction chamber is thin enough and the convective heat loss through the top of the chamber is low enough to be considered isothermal. In addition, it is assumed that the thermoelectric cooler is kept on constantly.

Figure 21A:
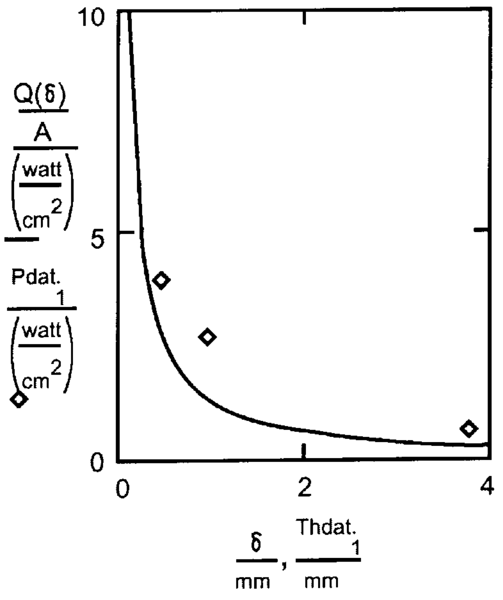
FIGS. 21A and 21B are graphs of steady state power and cooling time versus thermal insulator thickness, respectively, for the device of FIG. 20.
Figure 21B:
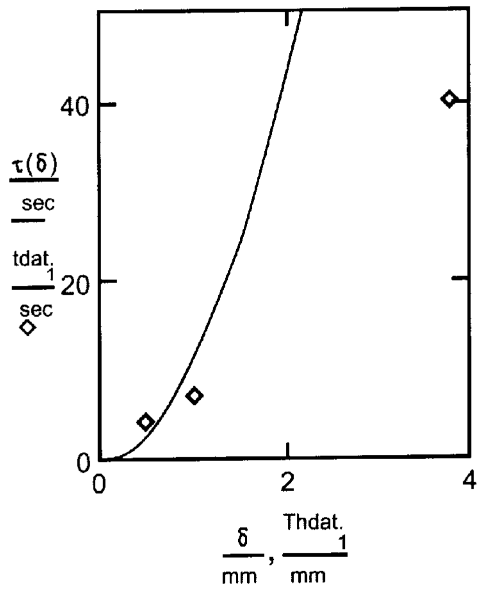

Given these assumptions, the steady state heat loss Q through the thermal insulator is given by $$Q=(kA/x)\ (T-T_{cooler})$$

where k and x are the thermal conductivity and thickness of the thermal insulator, A is the heater area, T is the heater temperature, and $T_{cooler}$ is the surface temperature of the thermoelectric cooler. If we assume that the thermal mass of the cartridge and reaction chamber contents are small, the time constant t for cooling is given by $$t=(x^2C\rho)/k$$

where C and ρ are the heat capacity and density of the thermal insulator, respectively. These equations are graphed in FIGS. 21A and 21B using the properties of phenolic resin, along with experimental results using the cooling time from 100° C. to 50° C. as t, while $T_{cooler}$=0° C.

These limited data show reasonable agreement with experiment, except for the timepoint for 3.8 mm thick insulator; in this case cooling through the air may have been more significant. These results demonstrate the validity of this simple analytical model. Clearly there is a tradeoff between power dissipation and cooling time; thinner insulating layers provide a rapid cooling rate at the expense of higher power dissipation. Since the cooling time t is a function of C and ρ, but the heat loss Q is not, the choice of insulating material is important. If we were to assume that the thermal conductivity k was proportional to density $$k=b\rho$$

where b is a constant, then the equations become $$Q=(kA)/x\quad t=x^2C/b$$

It turns out that the heat capacity C is fairly independent of material selection. By selecting materials with a small thermal conductivity k, the insulator thickness x can be proportionally reduced for a dramatic reduction in t. Low thermal conductivity porous materials can be used to improve the performance of such a reactor.

Figure 22:
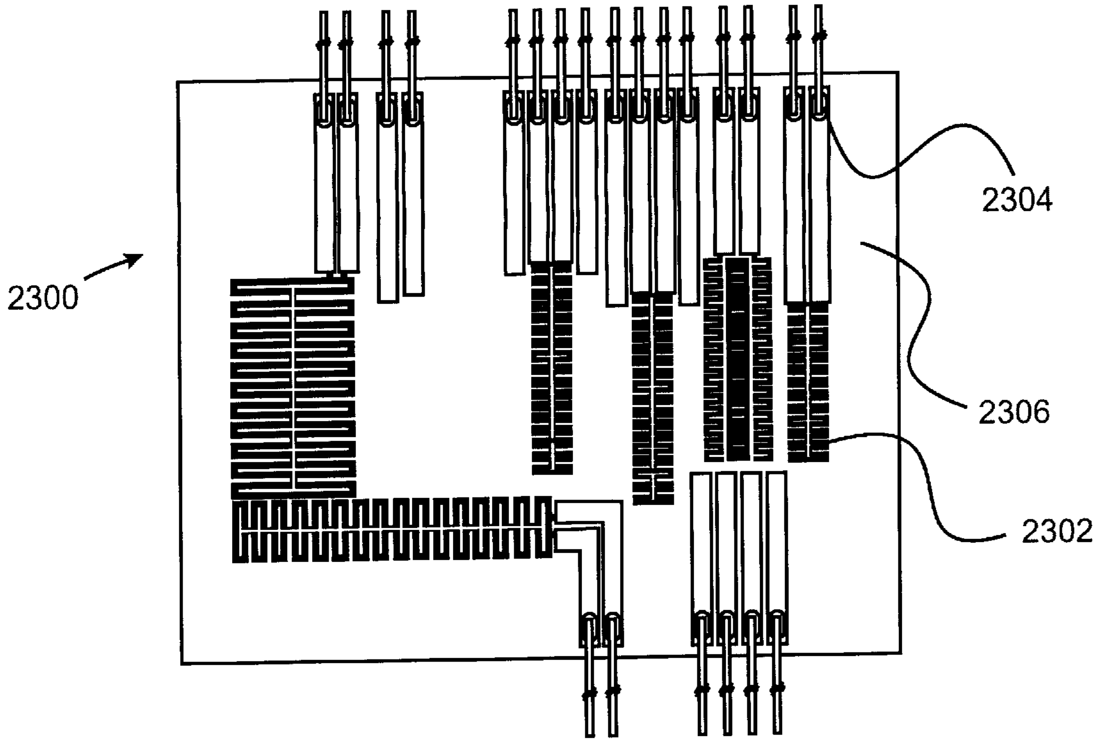
FIG. 22 is a top view of an array of thin-film heaters mounted on a single thermoelectric cooler for independent rapid thermal cycling reactions in the miniature device of FIG. 20.

Referring now to FIG. 22, a heater array layout 2300 for use with a miniaturized genetic analysis system will now be described. As shown, an array of separately addressable, thin-film inconel heaters 2302 are encapsulated in kapton film. These heaters are commercially available from Trans-Logic of Huntington Beach, Calif. The heater array 2302 is mounted on a single thermoelectric cooler 2306 with a thermal insulator (not shown) on top (e.g., polycarbonate film 0.5 mm thick), as shown in FIG. 20. The reaction chamber height is relatively small (e.g., about 0.0.1 to 1.0 mm) and the reaction chamber upper and lower walls are relatively thin, (e.g., about 0.1 mm).

In use with the present invention, each heater within the array 2302 is used to control the temperature of an individual reaction chamber within the genetic analysis system. The thermoelectric cooler 2306 functions to provide rapid cooling to all of the reaction chambers. During a rapid thermal reaction, such as PCR, the cooler 2306 is ON throughout the entire reaction. The heater is turned ON to maintain the reaction temperature. When the reaction temperature should be lowered, the heater is turn OFF, and the cooler 2306 rapidly decreases the temperature within the chamber.

10. Hermetically Sealed Microfluidic System

Figure 24:
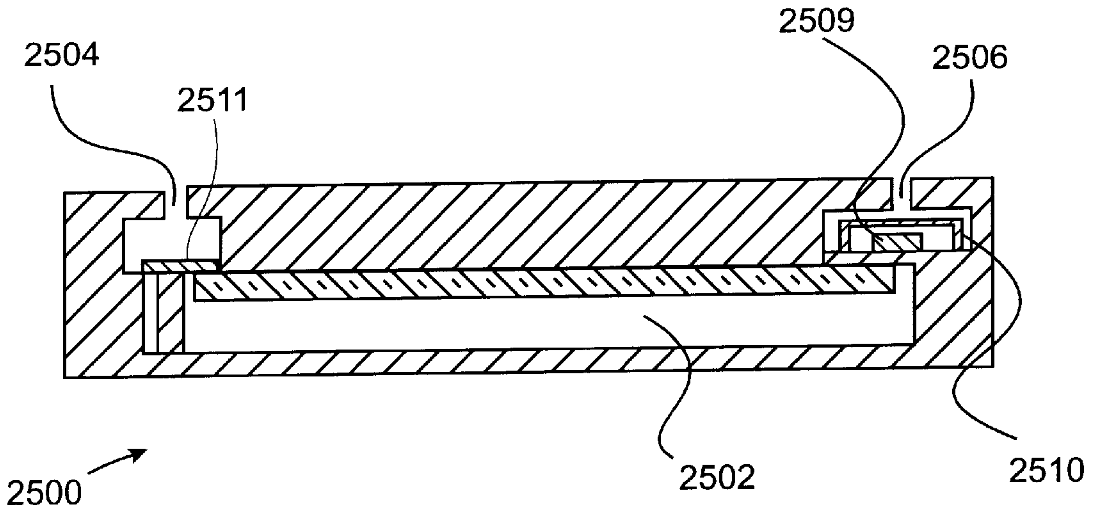
FIG. 24 is a schematic illustration of a sealed pneumatic cartridge having a deformable diaphragm for drawing fluid into or ejecting fluid from a chamber.
Figure 25:
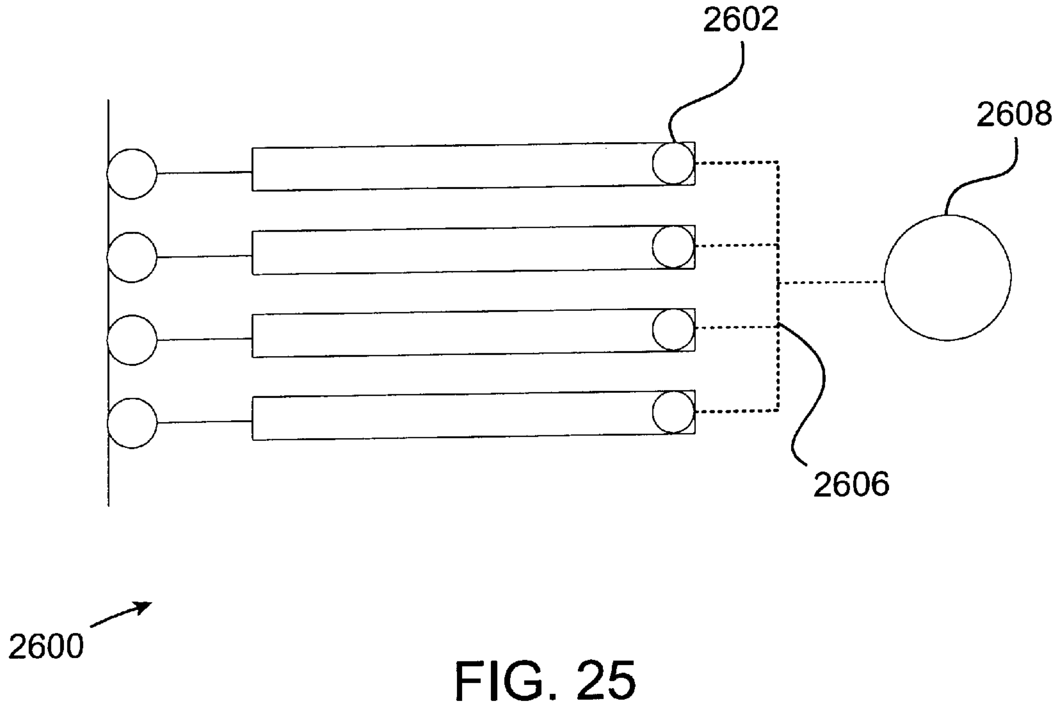
FIG. 25 schematically illustrates an array of sealed pneumatic chambers on disposable cartridges.

FIGS. 24 and 25 are schematic illustrations of hermetically sealed microfluidic systems for genetic analysis according to the present invention. In general, PCR reactions are extremely sensitive, but produce a high concentration of DNA product. This combination creates the danger of cross-contamination leading to erroneous results. A disposable cartridge may, for example, contaminate an instrument through PCR-product aerosols that could find their way into cartridges used in subsequent tests.

According to the present invention, a miniaturized sample-preparation system comprises chambers for reagent storage, reactions, and/or hybridization. The chambers are preferably defined in an injection-molded package that forms a cartridge (as discussed above in previous embodiments). Similar to above, movement of liquid between the chambers is carried out by pneumatic signals provided to the cartridge by a base instrument. In this embodiment, the chambers are so constructed to prevent any passage of gasses or liquids between the instrument and the disposable cartridge.

Two approaches appropriate for disposable cartridges are described herein. In the first approach shown in FIG. 25, a disposable cartridge 2500 defines a reaction chamber 2502 with first and second pneumatic ports 2504, and 2506. A hydrophobic vent 2509 extends between one of the ports 2506 and reaction chamber 2502. A deformable diaphragm seal 2510, such as latex or polyimide, covers the porous hydrophobic vent 2509. Fluids can be drawn into, or ejected from, the chamber by applying vacuums or pressures to the pneumatic ports 2504, 2506. Because deformation of the diaphragm seal 2510 is limited, the it must be positioned in the desired orientation before liquid enters the reaction chamber 2502. For example, diaphragm seal 2510 can be positioned in a "fully exhausted" state by pressurizing pneumatic port 2506 and opening diaphragm valve 2511 to eject gas into an empty chamber. This approach can be extended to a linking/mixing chamber structures (described herein).

In a second approach shown in FIG. 25, a disposable cartridge 2600 comprises both fluidic and pneumatic channels. Single vents 2602 or sets of vents are linked to a pneumatic driving chamber that is addressed by a disposable pneumatic manifold 2606. As with the first approach, a driving chamber membrane 2608 must be appropriately positioned by exhausting gas into other chambers (e.g., a corresponding driving chamber connected to a second chamber cluster). The driving membrane 2608 is addressed by a non-disposable pneumatic port (not shown).

11. Hybridization Cartridge

A nucleic acid sample, (target) requirements for hybridization can typically be reduced by decreasing the hybridization chamber volume. Hybridization is currently carried out in a cartridge with an internal volume of about 250 ul and a 10 nM target, requiring about 2.5 pmoles. By decreasing the chamber volume to about 10 ul, only about 100 fmoles of target is required to maintain a 10 nM concentration.

Typically, aggressive mixing is necessary to achieve rapid and reproducible hybridization with sufficient signal and discrimination. One method of reducing the chamber volume is to decrease the distance between the oligonucleotide probe array and the opposite surface of the cartridge. Maintaining fluidic control while providing aggressive mixing can be challenging in this geometry because capillary forces can begin to dominate, resulting in poor convection and trapped bubbles. The present invention provides a system and method for removing bubbles and providing uniform, aggressive convection uniformly across the probe array.

Figure 29:
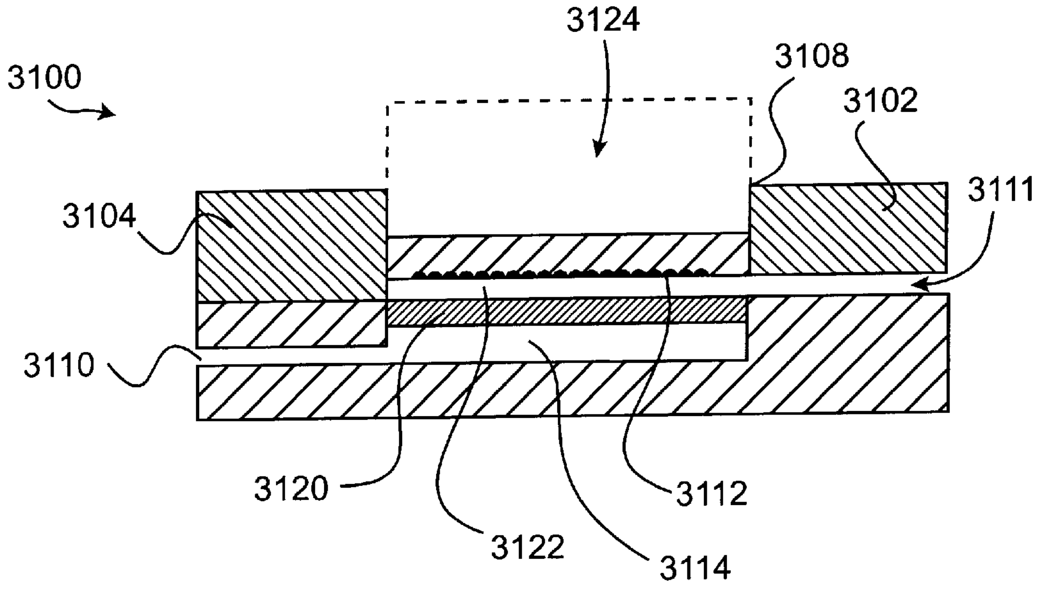
FIG. 29 is a partial sectional view of a cartridge adapted for low volume hybridization of high density oligonucleotide arrays.

As is seen in FIG. 29 a hybridization system 3100 includes a base 3102 that defines a hybridization chamber 3122 with a pneumatic port 3110 and a fluidic port 3111. The probe array 3112 is mounted to base 3102 and a thermal control block 3124 for controlling the temperature of probe array 3112 during hybridization. According to the present invention, a composite porous membrane 3120 is positioned a relatively small distance (e.g., 10 to 100 um) from probe array 3112 to create a smaller chamber 3122 therebetween. The porous membrane 3120 preferably comprises a sandwich of hydrophobic material, such as Versapore 200 from Gelman associates, and a thin membrane with neutral wetting properties, such as particle-track etched polycarbonate from Poretics.

After the target solution is introduced into hybridization chamber 3122, complete filling is effectively ensured by pulling a vacuum on pneumatic port 3110. The pneumatic port 3110 is then pressurized to inject a high density of bubbles substantially uniformly into hybridization chamber 3122. The bubbles provide mixing by expanding, coalescing, and impacting the oligonucleotide array 3112. Further mixing may be induced by pulling a vacuum on port 3110 and withdrawing the bubbles from the chamber. Alternatively, injecting and withdrawing gas from the hybridization chamber results in aggressive uniform convection to the entire oligonucleotide array surface.

Current hybridization chambers typically have a volume of 250 ul. However, lower volume hybridization chambers would provide greater sensitivity and shorter assay time. Unfortunately, when attempting to design hybridization chambers having very small height dimensions, surface tension and wetting effects become problematic, thereby making the control of fluids and bubbles within the chamber difficult, especially when the chamber height is reduced below 0.5 mm. Specifically, capillary pressures increase inversely with the chamber height, so that a 0.1 mm high chamber with non-wetting walls corresponds to 0.2 psi for water. Pressures in this range are typically sufficient to frustrate fluid control.

The low volume hybridization systems of the present invention, as set forth herein, are adapted to operate at volumes in the range of 0.1 to 100 $\mu$l, and more preferably in the range of 1 to 20 $\mu$l, and most preferably, in the range of 5 to 10 $\mu$l.

Figure 41:
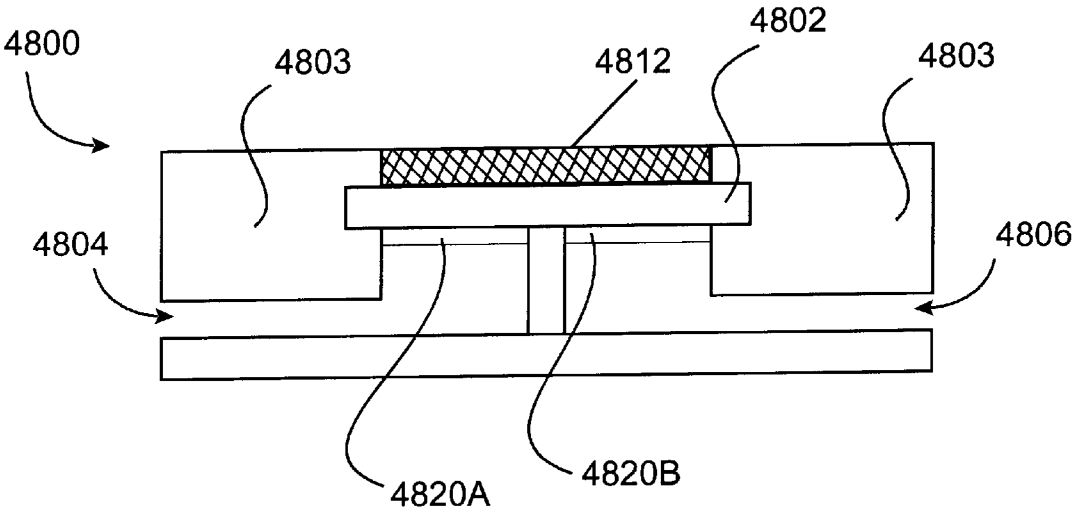
FIG. 41 illustrates a low volume hybridization system having a movable pneumatically-controlled wall.

FIG. 41 illustrates an embodiment of a low volume hybridization system 4800 which avoids the above limitations. Specifically, hybridization system 4800 includes a hybridization chamber 4802 and pneumatic ports 4804 and 4806. A probe array 4812 is mounted to base 4803. A flexible diaphragm 4820 is included and is addressed by pneumatic ports 4804 and 4806 such that movement of flexible diaphragm 4820 operates to decrease the height of hybridization chamber 4802 such that the chamber volume can be expanded for draining and filling operations and contracted for hybridization. Draining and filling of chamber 4802 is accomplished by simultaneously applying a pressure or a vacuum to pneumatic ports 4804 and 4806. Mixing in chamber 4802 during the hybridization stage can be accomplished by alternatively applying pressures or vacuums to pneumatic ports 4804 and 4806, thus causing separate portions 4820A and 4820B of diaphragm 4820 [proximal pneumatic ports 4804 and 4806, respectively] to flex in a manner such that fluid is squeezed back and forth within the hybridization chamber as the chamber height above diaphragm portions 4820A and 4820B is varied.

Figure 42:
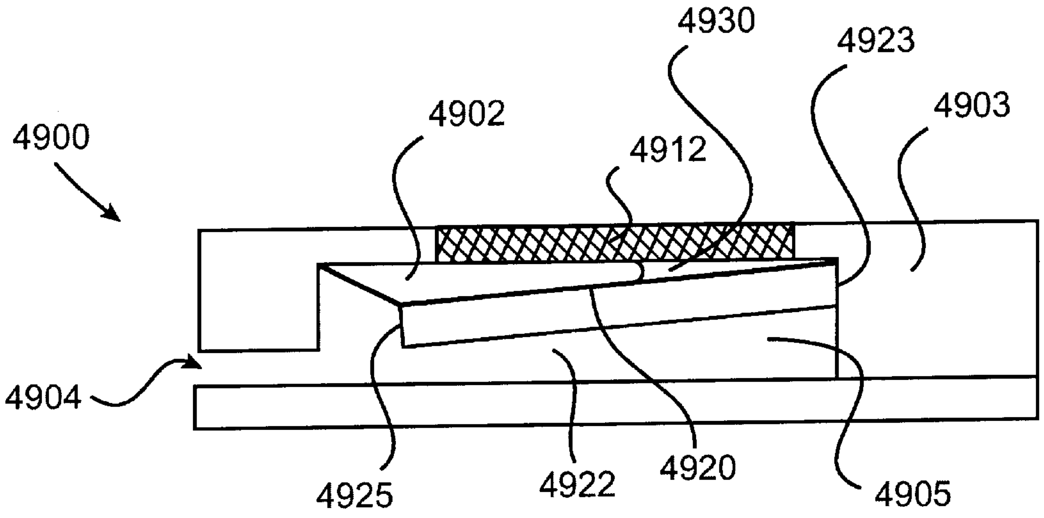
FIG. 42 illustrates a low volume hybridization system having a movable pneumatically-controlled pivoting wall.

FIG. 42 illustrates an alternative embodiment of a very low volume hybridization system 4900 which includes a hybridization chamber 4902 and a pneumatic port 4904. Probe array 4912 is mounted to base 4903. A flexible diaphragm 4920 mounted to a rigid plate 4922 is also included. Flexible diaphragm 4920 extends fully across the top and thereby seals pressure chamber 4905. Rigid plate 4922 has a hinged end 4923 and a free end 4925. Accordingly, rigid plate 4922 pivots about hinged end 4923 as a pressure differential is applied to pneumatic port 4904. Specifically, as the pressure in pressure chamber 4905 is decreased, rigid plate 4922 pivots downwardly at its free end 4925. Correspondingly, as the pressure in pressure chamber 4905 is increased, rigid plate 4922 pivots upwardly at its free end 4925. As such, the dimension of hybridization chamber 4902 can easily be varied by tilting rigid plate 4922 by applying a pressure differential at pneumatic port 4904. Due to the effects of surface tension, hybridization fluid 4930 will tend to collect at the narrow end of hybridization chamber 4902, as shown. Therefore, decreasing the volume of hybridization chamber 4902 by tilting rigid plate 4922 upwardly will cause the fluid to spread across the surface of the flexible diaphragm. As a consequence, repetitive application of a pressure differential in chamber 4902 will cause the rigid plate 4922 to tilt upwardly and downwardly will cause mixing in the fluid as it repetitively spreads out and then retracts across the diaphragm surface. In addition, upward tilting of rigid plate 4922 also reduces the volume of the hybridization chamber 4902. Draining and filling can be accomplished by applying a vacuum to pneumatic port 4904.

In another embodiment, motion of the membrane is provided using forces other than pneumatic (e.g., electrostatic, magnetic, or piezoelectric). For example, plate 4925 is metallic and a moving magnetic field moves the plate.

12. Systems for Removal of Excess Nucleic Acid Material After Hybridization

In another embodiment, systems and methods are provided for removing excess nucleic acid material after hybridization. In this aspect of the invention, the nucleic acid target material is washed away after hybridization to remove mismatches and to reduce fluorescence background. Since most of the match/mismatch discrimination occurs during this step, it is important that the stringency (i.e., temperature and salt concentration) of the material is carefully controlled. Also, there are advantages to performing this wash step without the use of moving parts.

Figure 23:
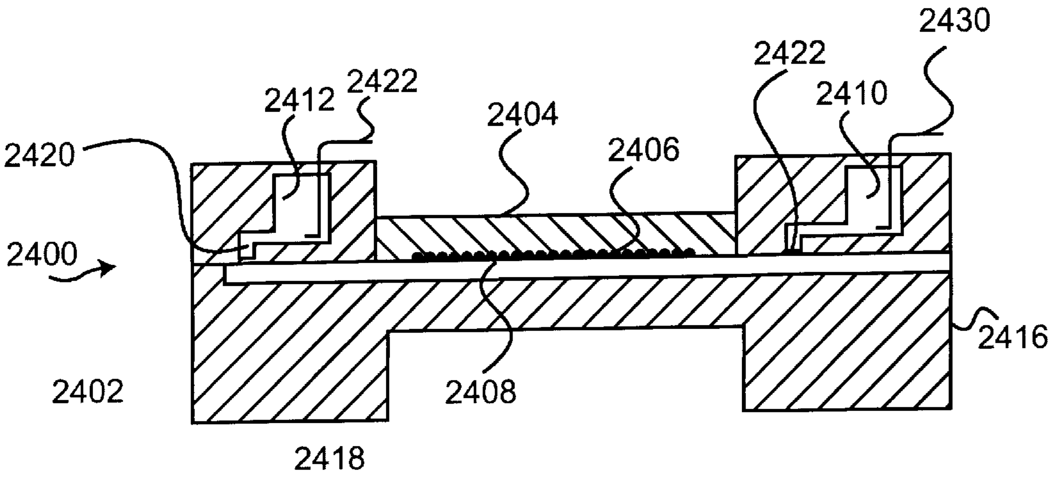
FIG. 23 is a cross-section view of a hybridization cartridge.

As shown in FIG. 23, a polycarbonate base cartridge 2402 includes a hybridization chamber 2408 and at least one (preferably two) additional electrolysis chambers 2410, 2412 on either side of the hybridization chamber 2408. Electrolysis chambers 2410, 2412 have positive and negative electrodes 2430, 2432, respectively, (preferably platinum screens) mounted therein. Electrodes 2430, 2432 may also comprise metals other than platinum, carbon, graphite or pyrolitic forms of these materials, conductive polymers and the like. Alternatively, the electrolysis chambers 2410, 2412 may be filled with a solid polymer electrolyte. Electrolysis chambers 2410, 2412 are sealed from the hybridization chamber 2408 with barriers or membranes 2420, 2422. (Barriers 2420 and 2422 can comprise dialysis membranes). As in previous embodiments, the oligonucleotide array 2406 is mounted to cartridge 2402 within chamber 2408, and a fluidic port 2416 fluidly couples chamber 2408 with the remainder of the system.

In use, the electrolysis chambers 2410, 2412 are filled with a buffer solution and the probe array undergoes hybridization as previously described. After hybridization, the target is electrophoretically swept from the hybridization chamber 2408 by passing a current between electrodes 2430, 2432. Eventually, the target nucleic acid will be trapped on the barrier 2422 covering the positive electrolysis chamber 2410 (i.e., the anode), or will enter into chamber 2410.

In alternative embodiments, the electrolysis chambers and/or the channels leading to them may be filled with a gel, or the dialysis membranes may be replaced with a gel.

13. Vent Structures for Sensorless Fluid Positioning

In another aspect of the present invention, systems and methods are provided for sensorless fluid positioning in microfluidic vent structures. Previous microfluidic chambers typically use chambers terminated with hydrophobic vents. In some cases, evaporation occurs from reaction chambers at elevated temperatures and liquid remnants near the vent coalesce over time and choke the vent. In addition, small unintended liquid plugs may be forced into the chamber ahead of the sample, where they block the vent.

Figure 40:
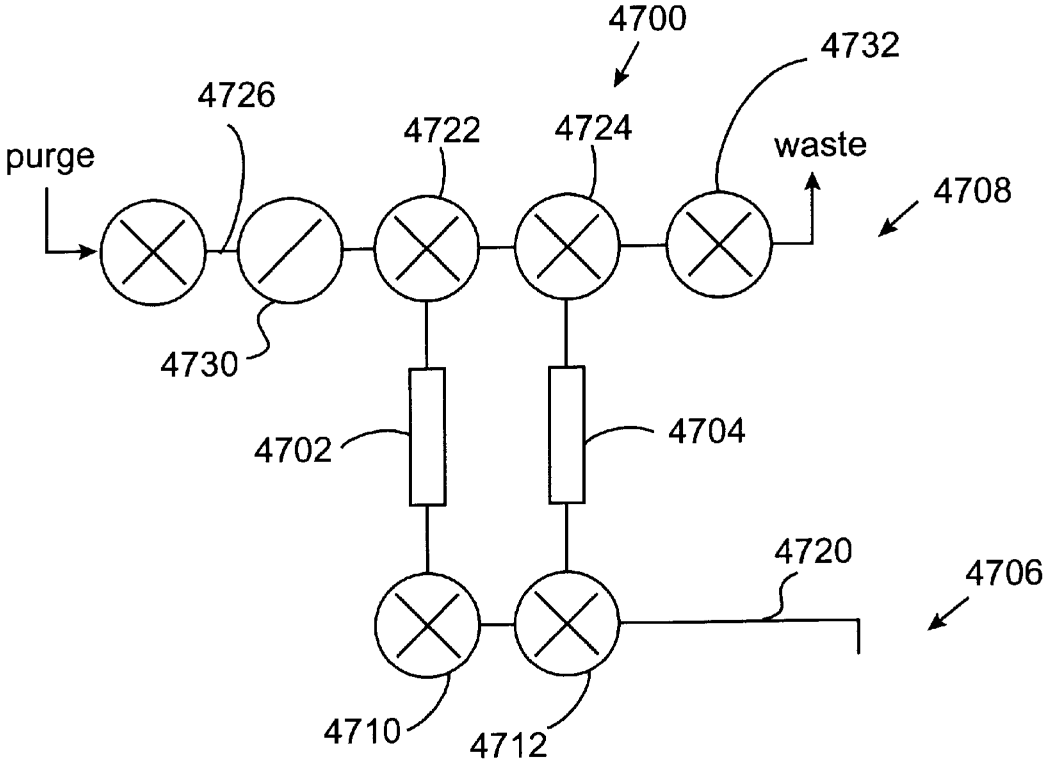
FIG. 40 illustrates a microfluidic system incorporating a vented common line.

As shown in FIG. 40, a microfluidic vent structure 4700 includes first and second chambers 4702, 4704 each coupled to first and second vented common assemblies 4706, 4708. First vented common assembly 4706 includes a pair of valves 4710, 4712 coupled to chambers 4702, 4704 and each other along a common line 4720. Second vented common assembly 4708 also includes a pair of valves 4722, 4724 coupled to the other end of chambers 4702, 4704, respectively, along a common line 4726. In addition, a vent 4730 is positioned along line 4726 between valve 4722 and a purge line, and a third valve 4732 is positioned along line 4726 between valve 4724 and a waste line. Of course, it will be recognized that this system can be modified to include a single reaction chamber, or more than two. In addition, a network of common lines and vented common lines may be used with this system.

In use with the present invention, fluid is directed through chambers 4702, 4704 through common line 4720 and sensorless positioning is accomplished through common line 4726. For example, first chamber 4702 is loaded through common line 4720 by opening its inlet and outlet valves. Fluid would stop flowing once it contacts vent 4730 in common line 4726. The inlet and outlet valves are then closed and excess fluid is purged from common line 4726 into the waste line. Evaporation from chamber 4706 is minimized or eliminated because the fluid is contained by the valves in common line 4726. Vent choking by the coalescence of liquid remnants is minimized or eliminated because the vented common line 4726 has a flow through arrangement, and can be purged. Unintended liquid plugs moving ahead of the sample enter the vented common line 4726, and are purged from the system 4700. Also, wash solutions may be introduced through the purge vent.

In other embodiments, tapered vent conduits may be used in the vented common line. Alternatively or additionally, the vent 4730 may also be used as a flow-through debubbler. In another embodiment, the purge line and valve in the vented common line is eliminated, and the fluid is purged from vent 4730 through common 4706.

14. Pneumatic Stepper

A limitation of employing externally applied pressures and hydrophobic vents to move and stop fluid segment movement flow is that the applied pressure must be high enough to initiate fluid-segment motion, but low enough to prevent fluid segment break up. Both of these minimum and maximum pressures are a function of cartridge geometry, fluid location, and cartridge history.

Figure 43:
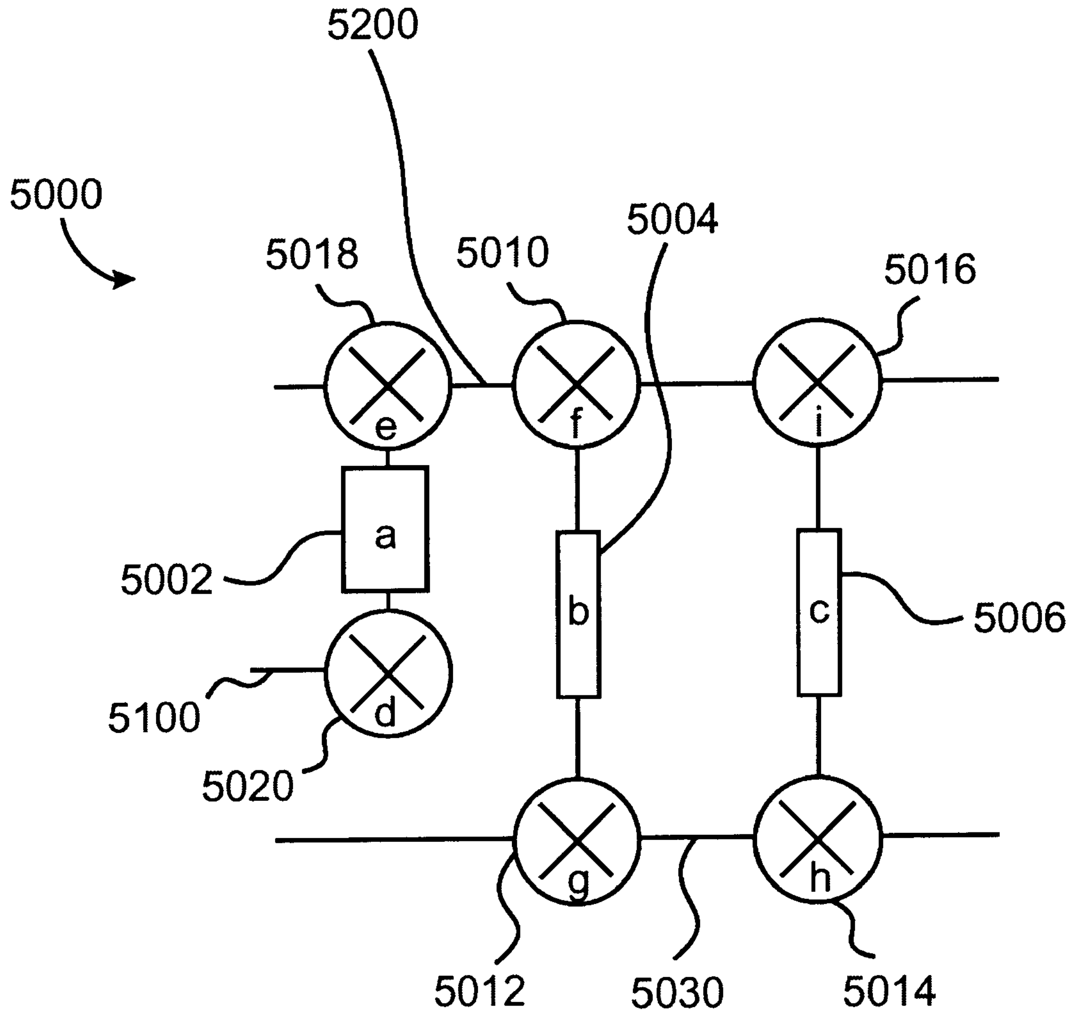
FIG. 43 illustrates a fluid distribution device using a pneumatic stepper.

In another embodiment of the invention, as shown in FIG. 43, a pneumatic stepper 5000 is provided to precisely control fluid movement in microfluidic chambers having hydrophobic vents. Pneumatic stepper 5000 overcomes the above discussed limitations of evaporation from reaction chambers at elevated temperatures, liquid remnants near the vent and small unintended liquid plugs being forced into the chamber ahead of the sample. This is accomplished by providing gas packets with high enough pressure to always initiate fluid movement, yet having a self-limiting displacement which avoids fluid break up. As such, pneumatic stepper 5000 is specifically adapted for delivering packets of pressurized gas into a flow channel.

Pneumatic stepper 5000 comprises first, second and third chambers 5002, 5004 and 5006, respectively. Valves, 5010, 5012, 5014, 5016, 5018 and 5020 are provided with valves 5010 and 5012 being connected to opposite ends of chamber 5004 and valves 5014 and 5016 being connected to opposite ends of chamber 5006 and valves 5018 and 5020 being connected to opposite ends of chamber 5002 as shown. A Pressure line 5100 is connected to a pressure source, not shown. A first common line 5200 runs between valves 5018 and 5010. A second common line 5030 runs between valves 5012 and 5014.

The moving of a liquid sample from chamber 5004 to 5006 is accomplished by the following sequential steps. First, valves 5010, 5012, 5014 and 5016 are opened. Secondly, valve 5018 is closed. Thirdly, valve 5020 is opened and a pressure is received through line 5100 thereby increasing the pressure in chamber 5002. Valve 5020 is then closed, sealing chamber 5002. Fourthly, valve 5018 is then opened, thus permitting a volume of gas to be expelled from chamber 5002 into common line 5200 and thus into chamber 5004. The gas pressure entering chamber 5004 through valve 5010 can be used to force a liquid segment to move from chamber 5004 through line 5030 to chamber 5006. Repetitive "stepping" of the fluid can be accomplished by repeatedly pressurizing chamber 5002 through line 5100 and then expelling the pressure into common line 5200 by opening and closing valve 5018 and 5020.

The volume displaced by a repeated cycle of the above steps is given by the equation:

$$dV_{step}=[P_{source}/P_{channel}]*V_{ballast}$$

where $P_{source}$ is the pressure in line 5100, $P_{channel}$ is the minimum pressure required to move a fluid segment through chamber 5004, and $V_{ballast}$ is the volume of chamber 5002. The optimal selection of the volume of chamber 5002 thus ensures reliable fluid movement from chamber 5004 to 5006.

15. Flow Through Thermal Treatment Device

Microfabricated silicon devices for flow-through processing of biological reactions provide the opportunity for integrating heaters into their designs, however, several limitations to such techniques are known to occur. For example, the high thermal conductivity of silicon makes it difficult to create distinct thermally isolated zones. Moreover, although it is possible to define fluid volumes below 1ul in silicon devices, many assays require volumes of 10 ul and above, and it is sometimes preferable to treat liquid volumes on the order of 1 ml. Furthermore, such processed silicon parts are expensive relative to alternative injection molded parts.

Figure 44A:
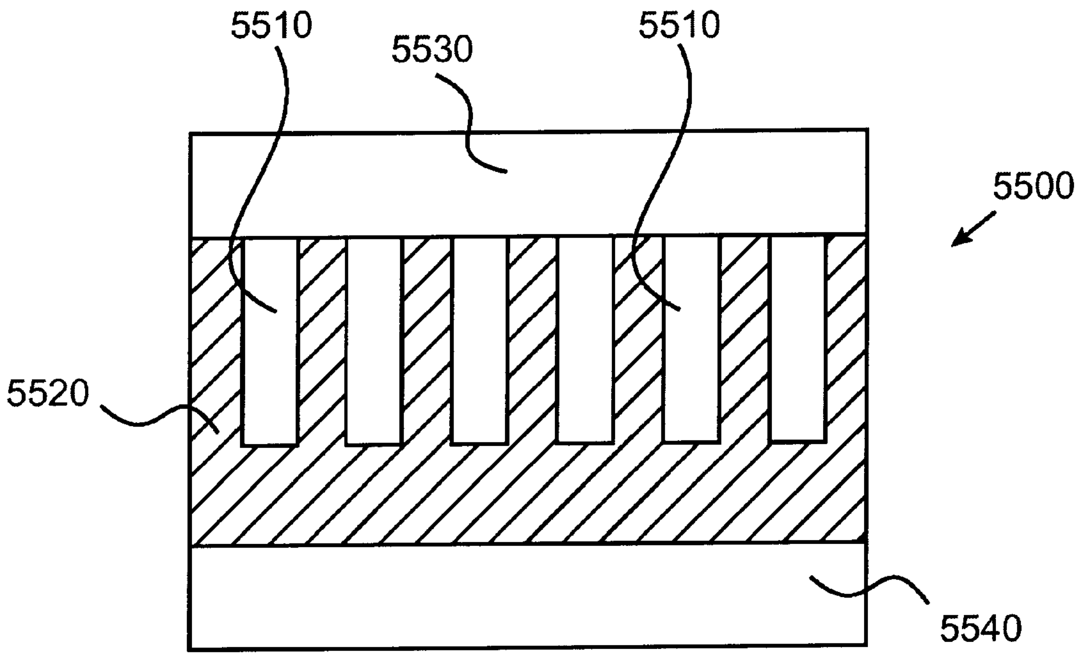
FIG. 44A illustrates a sectional view of a flow through thermal treatment device.
Figure 44B:
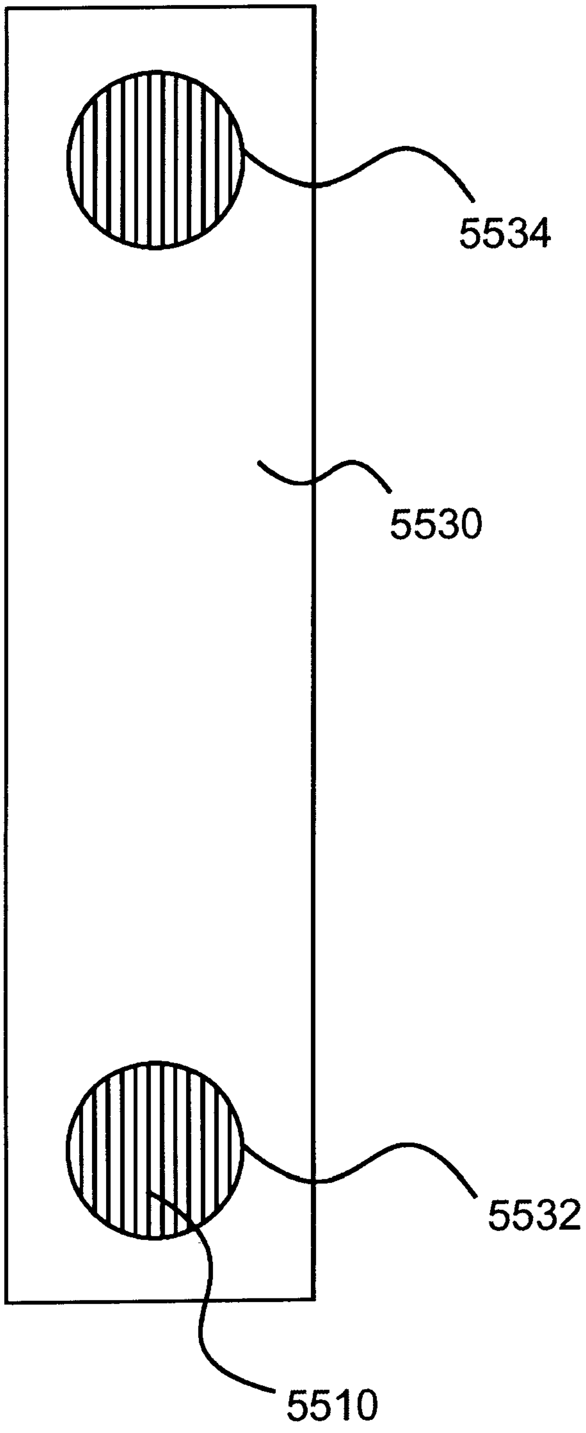
FIG. 44B illustrates a top view of the flow through thermal treatment device of FIG. 44A.

In another aspect of the invention, as is shown in the sectional view of FIG. 44A and the top view of FIG. 44B, a flow through thermal treatment device 5500 provides precise thermal control in a fluid while minimizing processing area, thus overcoming these above limitations, as follows. A series of small parallel flow-through silicon chambers 5510 are formed within a silicon cartridge 5520, as shown. Chambers 5510 are preferably etched in a silicon surface using photolithography and etching techniques such as reactive ion etching [RIE]. Alternately, device 5500 can be mounted on a polymeric cartridge (not shown). A coverslip 5530 having inlet hole 5532 and outlet hole 5534 is preferably formed from Pyrex and is anodically bonded over chambers 5510. In one embodiment, coverslip 5530 could instead be made of silicon, preferably being fusion bonded to the device. Chambers 5510 are preferably 10 to 200 um tall and 1 to 20 um wide and have a length from inlet 5532 to outlet 5534 of 0.2 to 5 mm. In an alternate embodiment, chambers 5510 could be replaced by a single large silicon channel, on the order of 500 $\mu$m wide and 1 to 100 $\mu$m deep. Inlet and outlet ports 5532 and 5534 which pass through coverslip 5530, have a preferable diameter of 0.05 to 2 mm. In alternate embodiments, the inlet and outlet ports can instead pass through the sides of device 5500, rather than through its cover plate on thrrough silicon cartridge 5520. The fluid path through chambers 5510 and ports 5532 and 5534 can preferably be coated with silicon or parylene or surface modified with silanes. Heating and temperature sensing elements 5540, which may comprise thin film sputtered metal resistors, [such as aluminum, platinum, NiCr or nickel], semiconductors, or hybrid structures such as conductive polymer or thin film heaters on kapon, suitable both for heating and sensing, or thermoelectric coolers may also be fabricated on the non-bonding side of the silicon, as shown. The assembled thermal treatment device 5500 is then preferably adhesively bonded to a fluidic control system [not shown] with its cover glass side facing downwardly. Alternatively, attachment of device 5500 to the fluidic control structure can be accomplished by wax, silicone, epoxy, melted polymer, eutectic materials and solder.

The precise thermal control provided by the device is especially important for (1) denaturation of DNA, particularly as a cycle in PCR, (2) annealing of DNA templates with primers, particularly with PCR, (3) heat denaturization of enzymes, and (4) lysing cells. Advantages of flow-through thermal treatment device 5550 include (1) coverslip 5530, when made of glass, allows easy observation of fluidics, (2) the high thermal conductivity of the silicon ensures that the fluids in chambers 5510 are generally at a uniform temperature, (3) the liquid volume of the device is minimized, (4) the silicon construction the integration of heating, sensing, and control functions.

Figure 44C:
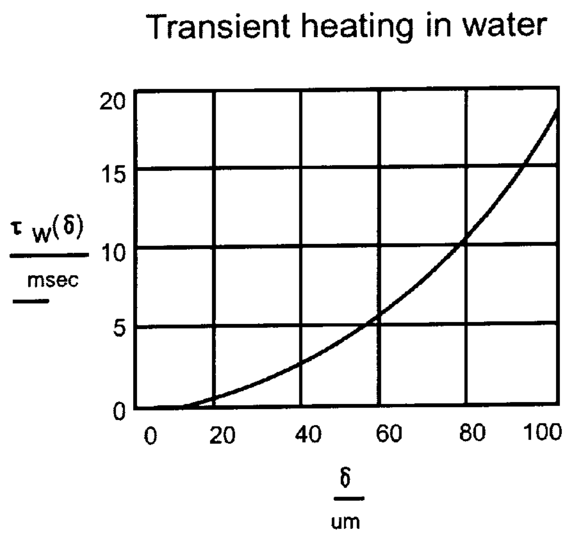
FIG. 44C shows the time constant for transient heating through a flow-through thermal device.

Chambers 5510 must be designed so that the sample flowing therethrough reaches thermal equilibrium. Assuming laminar flow, the time constant T for this transient heating process is given by the equations:

$$\tau=\delta^2/Dth \text{ and } Dth=C\rho/k$$

where Dth is the thermal diffusivity, δ is the channel half-distance, C is the heat capacity, ρ is the density, k is the thermal conductivity of the liquid and the transient time for water as shown in FIG. 44C. To ensure equilibrium, the space time $t_{space}$ must be at least 10 times the time constant τ. FIG. 55D shows the half-gap required in flow-through heating structure for water, where L=1 mm, w=10, 100 and 500 um.

Figure 44D:
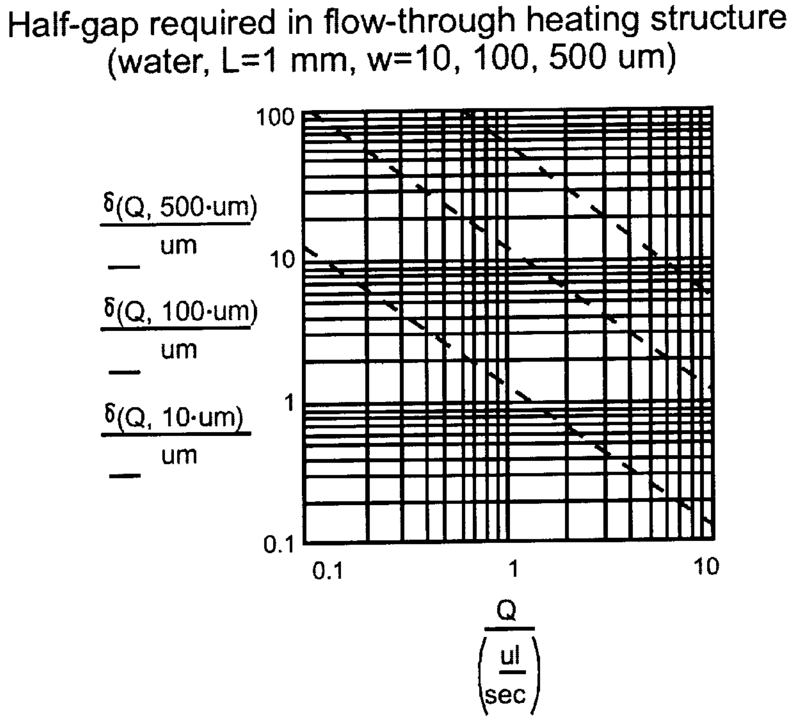
FIG. 44D shows the half-gap required in a flow-through thermal device

$T_{space}$ and δ are calculated from the equations:

$$T_{space}=[2Lw\delta]/Q=10\tau$$

and $$\delta=[LwD_{th}]/5Q$$

where L is the channel length, w is the channel depth, δ is the half-channel depth, and Q is the flow rate. As can be seen from FIG. 44D, for a flow rate of 1 ul/sec, channel gaps 5510 on the order of 1 to 10 um are therefore required. Even smaller gap widths are required as the channel length is decreased from 1 mm. By using multiple channels in parallel, the flow rate in each channel is reduced, allowing for larger gaps and shorter channels.

16. Molded Microcapillaries

In yet another embodiment, a microfluidic reaction system is fabricated based on surface molded polymeric capillary (SURF-CAP) technology. SURF-CAP technology allows structure to be fabricated on polymeric, e.g., polycarbonate substrates that may be disposable and thus eliminates wall joining (assembly) problems. In addition, it eliminates wall joining problems because the capillary is fabricated in place. In addition, vent assembly can be eliminated because the vents can be integrated on the device. This technology provides a mechanism for lithographically defining small features and a bridge to MEMS technology. In addition, this technology enables integration with heaters and controllers.

A similar technology using a sacrificial photoresistic layer can be found in P. F. Man et al. "Microfluidic Plastic Capillaries On Silicon Substrates: A New Inexpensive Technology For Bioanalysis Chips", 1997 MEMS Conference, Jan. 26–30, 1997, Nagoya, Japan. When fabricating the capillaries on a parylene substrate, a layer of photoresist first needs to be deposited on the substrate. Depositing such a photoresist layer thicker than 100 um is difficult and it limits system geometry. Moreover, the acetone used to remove the photoresist layer alters the surface properties of the parylene so that instead of being hydrophobic, it becomes hydrophilic after photoresist removal.

Figure 45A:
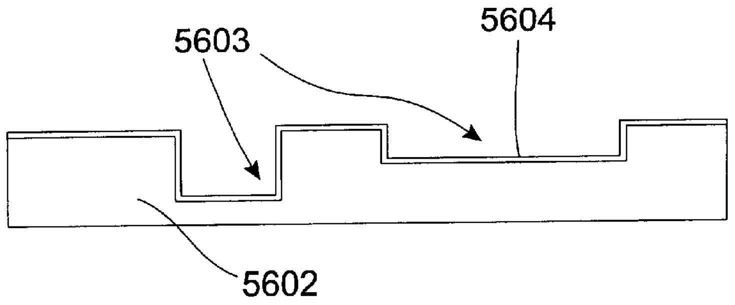
FIGS. 45A, 45B, and 45C illustrate sequential steps in the fabrication of a molded parylene microcapillary.
Figure 45B:
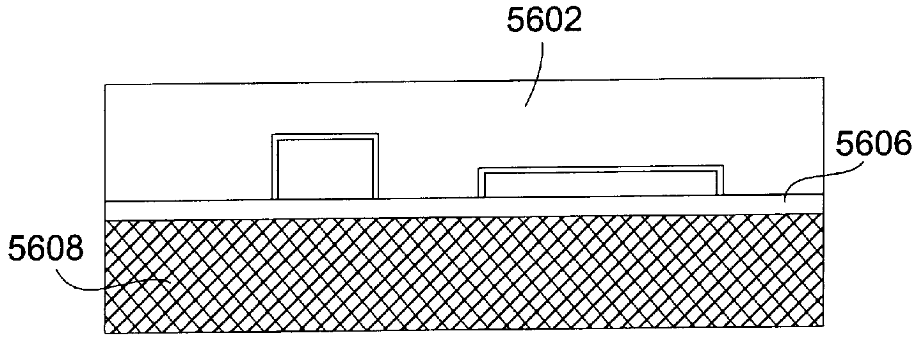
Figure 45C:
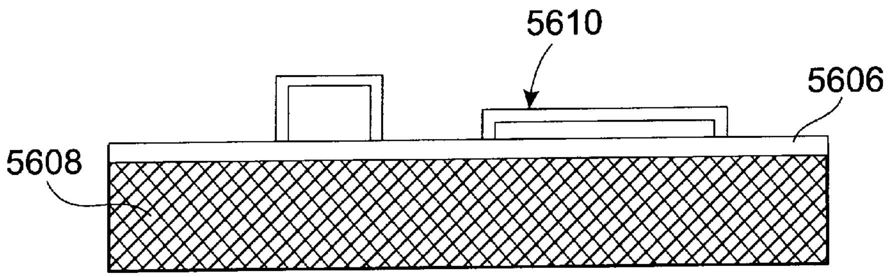

In another embodiment of the present invention, SURF-CAP molded parylene microcapillary 5600 is fabricated by the sequentially performed steps shown in FIGS. 45A, 45B, and 45C, respectively.

Referring first to FIG. 45A, a mold part 5602 having etched cavities 5603 is formed from silicon, glass, or other materials using microfabrication techniques such as annisotropic etching, wet chemical isotropic etching, plasma etching or reactive-ion etching [RIE]. Alternatively, mold part 5602 can be machined from plastic or metal. A release layer 5604, preferably comprising a soap film, silane, wax, photoresist, oil or thin layer of parylene N, is then optionally coated onto mold part 5602, by spinning, dipping or vapor phase coating.

Referring next to FIG. 45B, a first layer of parylene 5606 is then deposited on a substrate 5608 which is preferably comprised of polycarbonate, silicon, glass, polypropylene or acrylic. Next, mold part 5602 is positioned over substrate 5608 and is preferably held thereon using a clamp or other alignment fixture. Alternately, the weight of the mold part may alone be sufficient to hold mold part 5602 onto substrate 5608.

Referring next to FIG. 45C, a second parylene layer 5610 is then deposited into the mold cavities 5603. Following this, mold part 5602 is carefully removed from substrate 5608. Accordingly, as shown in FIG. 45C, a finished structure having raised parylene areas is provided, with these regions of raised parylene corresponding to the locations where the second parylene layer 5610 was deposited into the mold cavities 5603.

Alternatively, the removal of mold part 5602 from substrate 5608 can be facilitated by heating which would cause differential expansion of the mold or to melt the release layer. In other embodiments, the release layer 5604 and mold part 5602 could also be chemically etched or dissolved away, for example, with the entire structure being immersed in 10% KOH at 80° C. If not destroyed by the removal process, mold part 5602 could be reused, thus yielding cost savings. Thereafter, optional subsequent coatings such as polyimide, photoresist or epoxy can be deposited for additional structural stability. In alternate embodiments, multiple molds could be applied sequentially to create capillaries on top of capillaries. Post-release operations such as photolithography and plasma etching could be used to pattern holes in the parylene layer. In addition, fluids can be manipulated within the various chambers and channels by deforming walls or by providing valves and vents as described herein.

17. Acoustic Manipulation of Biological Particles

Microfluidic devices for integrated cell handling typically encounter the problem of the cells adhering to the walls of the device, making the processing of biologic materials quite laborious, especially when separating different cell types. Although hydrodynamic focussing can be used to avoid wall contact by confining the cells within a narrow stream, such hydrodynamic focussing is limited in terms of cell positioning and thus it is difficult to achieve two-dimensional positioning. In another aspect of the present invention, an acoustic manipulation device is provided to position and move cells, viruses, other biological particles and beads including solid or porous gels, thus overcoming the above limitations as will be set forth below. As such, the present acoustic manipulation devices offers the advantages that: (1) particles can be arbitrarily moved, positioned and held in place, (2) particles can be sorted by buoyancy, and (3) contact between the wall of the device and the particles can be minimized.

An acoustic manipulation device, which may alternately comprise a surface-acoustic wave (SAW) device and/or a flextural plate wave (FPW) device is provided. A SAW device generally radiates more energy into a liquid as compared to a FPW device, which instead generally tends to act at the interface of the liquid. In one approach, standing waves are generated. Particles collect at nodes in such standing waves (e.g. due to their buoyancy). The particular transducer design employed determines the position and movement of these nodes. Accordingly, particle sorting by size and chemical receptor is possible, thus improving on existing equipment such as FACS cell sorters, Coulter Counters and centrifuges.

Figure 46A:
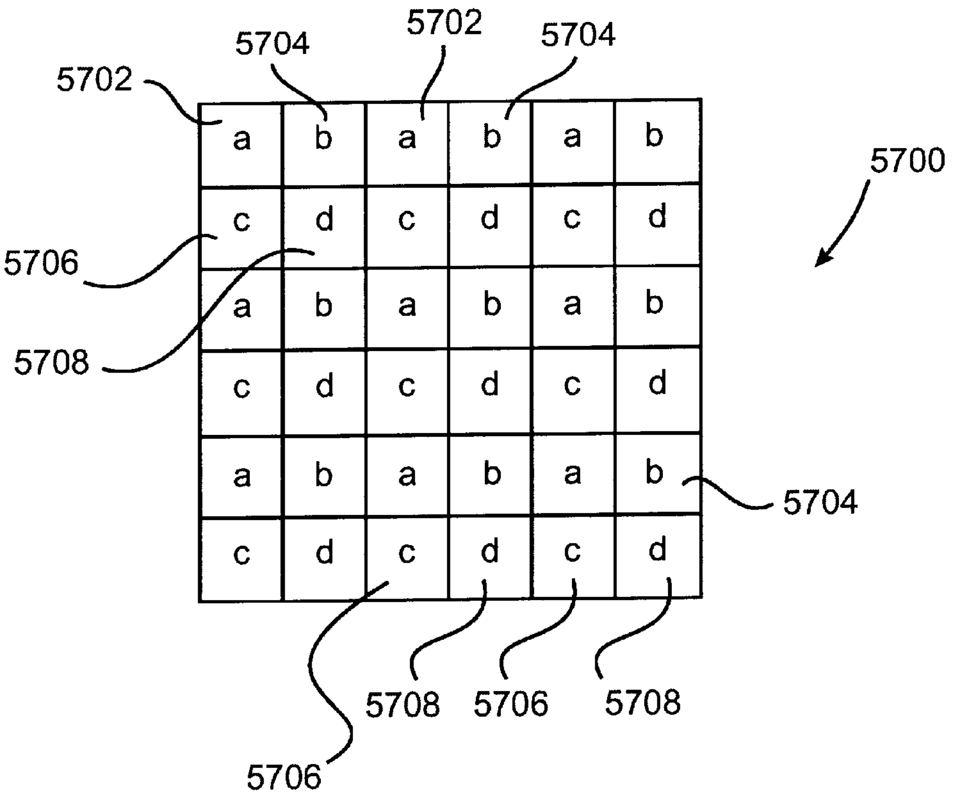
FIG. 46A illustrates a surface-acoustic wave transducer matrix.

FIG. 46A illustrates first embodiment employing a SAW transducer matrix 5700 according to the present invention, having its transducers positioned in a square-grid pattern. Specifically, transducers 5702 are positioned at locations "a". Similarly, transducers 5704 are positioned at locations "b", transducers 5706 are positioned at locations "c" and transducers 5708 are positioned at locations "d". As transducer pairs 5702:5704, 5702:5706, 5702:5708, 5704:5706, 5704:5708, and 5706:5708 are selectively activated, standing waves are created at node locations between a:b, a:c, a:d, b:c, b:d, and c:d, respectively. Similarly, a particle can be stepped in a second direction (perpindicular to the first direction) by sequentially activating transducer pari 5702:5704 and then 5706:5708. The creation of these standing waves induces the particles to collect at these nodes.

Particles can therefore be stepped in a first direction, for example, moving from location a:c by first activating transducer pair 5702:5706 and then by activating transducer pair 5704:5708. Consequently, as can be appreciated, the SAW transducer matrix of FIG. 46A can be used to move particles back and forth in mutually perpendicular directions. Moreover, activating transcuder pairs 5702:5708 or 5704:5706 can be used to localize particles in the node a:d and switch from horizontal to vertical movement, or vice versa.

In another embodiment, numerous particles scattered over the array are induced to move in a uniform direction by applying an additional biasing force such as, for example, mechanical gating or valving, pressure driven flow, dielectrophoresis, electrosmosis or electrophoresis may also be provided to ensure the particles step in the preferred uniform direction.

Alternatively, the various transducers could be designed asymmetrically to create dirrerent shaped nodes. In yet other alternative embodiments, additional physical forces can be combined with acoustics. For example, dielectrophoresis can be used to assist in positioning particles. Electrophoresis or electroosmosis can also be combined with these techniques.

Figure 46B:
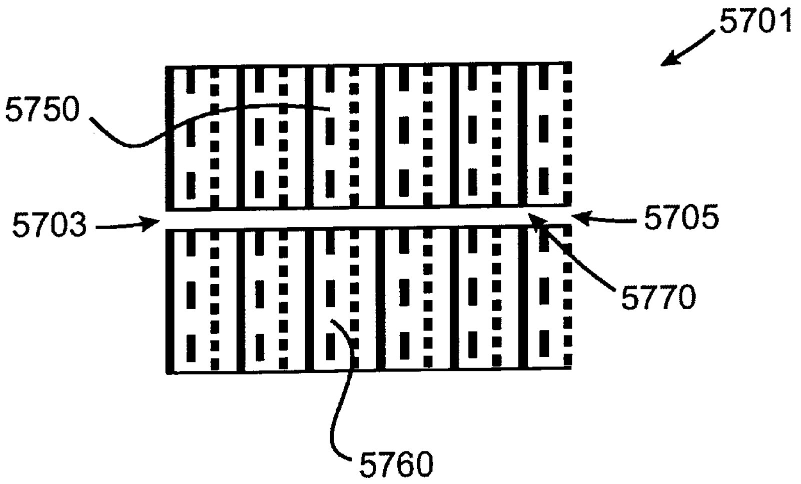
FIG. 46B illustrates a flexural plate wave matrix device.

FIG. 46B shows a FPW transducer arrangement 5701 for collecting, moving and sorting particles, optionally functioning as a FACS cell sorter, according to the present invention as follows. First and second 3-phase transducers 5750 and 5760, respectively, are positioned next to one another as shown and are driven such that an acoustic streaming velocity passes therealong forming a longitudinally-extending node at region 5770. Biological particles entering at end 5703 of transducer arrangement 5701 are induced to gather at region 5770, move along through the device, and then exit at end 5705. The particles can then be detected optically or electrically as they pass through the device along region 5770. Optionally, the particles may instead be deflected based upon sorting criteria as they exit the device at its end 5705.

In alternative embodiments, particles can be sorted by density, wherein higher density particles collect at peaks rather than nodes. In addition, nodes of varying intensity can be created by the transducer design, thus causing cells to segregate by density. Moreover, tags can be used to alter particle density.

18. Microfabricated Hydrophobic Vent

Figure 47A:
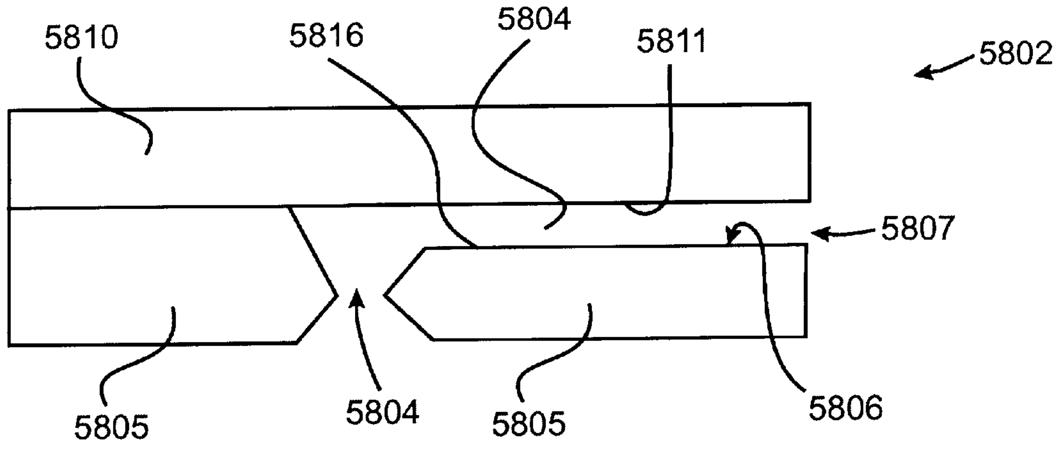
FIG. 47A illustrates a sectional side view of a silicon and glass hydrophobic vent.
Figure 47B:
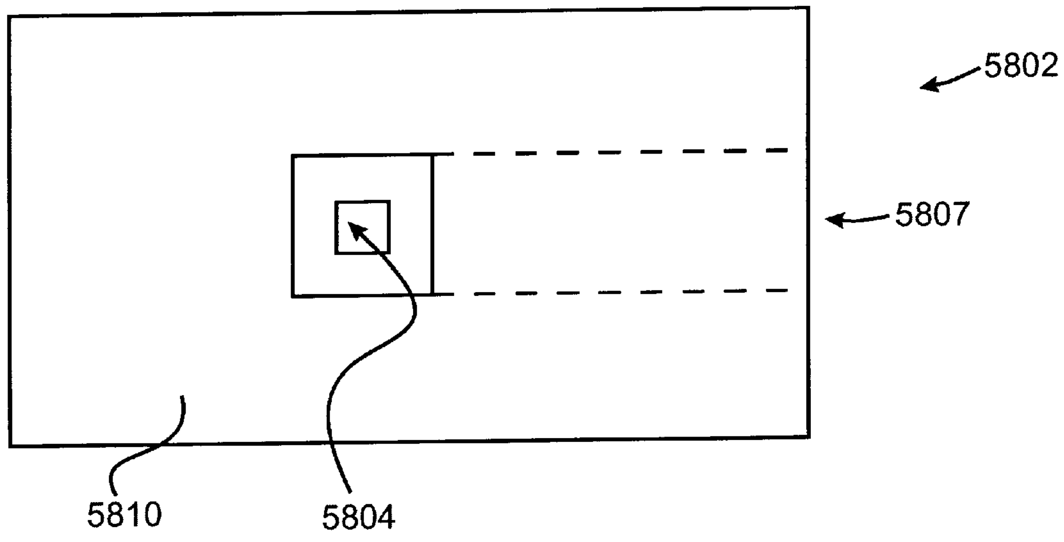
FIG. 47B illustrates a top view of the gas-liquid separator of FIG. 47A.

As is shown in FIGS. 47A and 47B, a hydrophobic vent structure 5802 is provided. Hydrophobic vent structure 5802 can be fabricated from silicon and glass by a two-step etching process as follows. First, a gap 5804 is etched to pass through silicon substrate 5805 and a depression 5806 is etched thereupon. The dimension of gap 5804 is preferably on the order of 0.1 to 10 um, as controlled by the etching process. A Pyrex glass cap 5810 is then attached on top of silicon substrate 5805, preferably using anodic bonding or adhesives such as epoxy, RTV, or cyannoacrylate. Surface 5811 of glass cap 5810 and surface 5816 of depression 5806 of substrate 5805 are then optionally rendered hydrophobic by silation with hexamethldisilazane (HMDS), or other appropriate silane. It is preferred that the exposed ligand on the silane is a polyfluorinated hydrocarbon. Alternatively, the surfaces can be made hydrophobic by plasma based CVD, followed by a chemical treatment or the deposition of a polymer film (e.g., silicone from a solvent or vapor phase paylene deposition). Accordingly, hydrophobic vent structure 5802 permits gas to pass freely through gap 5804, along the gap between depression 5806 and glass cap 5810 and out exit port 5807. In contrast, fluid flow through this passage is prohibited both by the very small dimensions of this passageway, and the hydrophobic coating of surface 5811 of glass cap 5810 and surface 5816 of depression 5806 of substrate 5805.

Figure 47C:
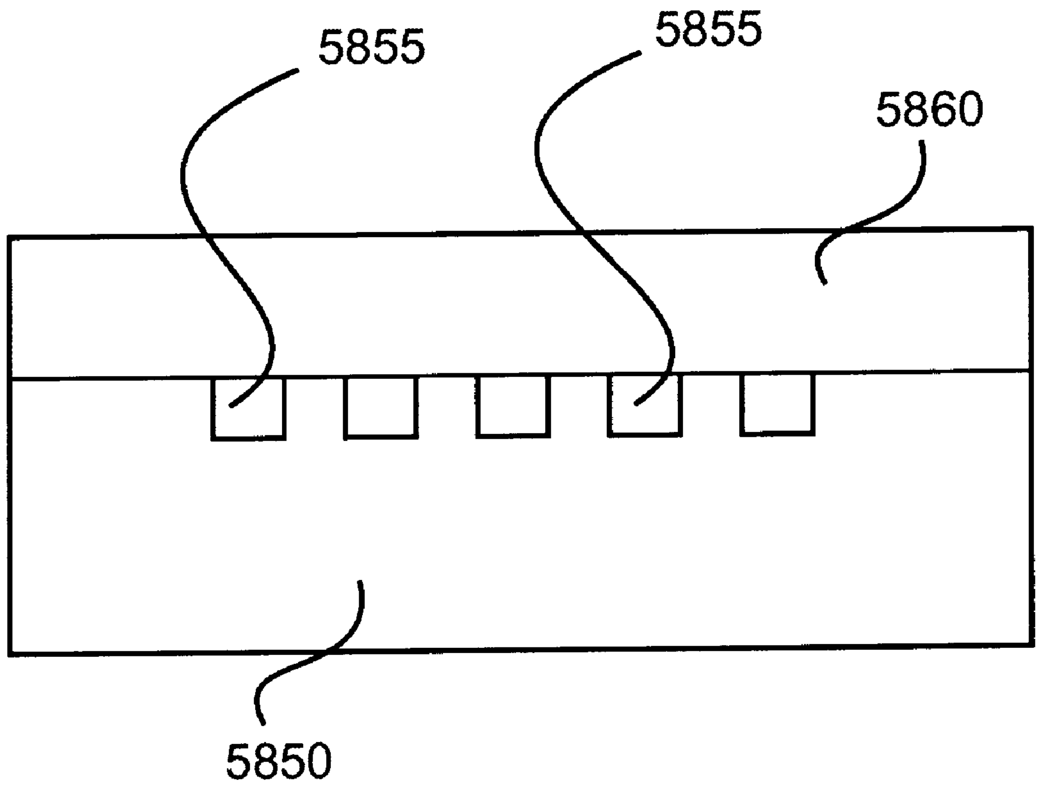
FIG. 47C illustrates a sectional view of a hydrophobic vent fabricated from two silicon substrates.

In yet another embodiment, as shown in FIG. 47C, a hydrophobic vent is fabricated of two silicon substrates, 5850 and 5860. Vent capillaries 5855 are annistropically cut through substrate 5850. Photolithography and reactive-ion etching (RIE) or chemical etching are then used to define the vent capillaries, preferably etching them to a depth of 2 to 10 um with capillary width of 0.5 to 10 um. Silicon substrate 5860 is then joined to silicon substrate 5850, preferably using silicon fusion bonding or adhesives such as epoxy, RTV, or cyannoacrylate.

Although the very small dimensions of vent capillaries 5855 prevents fluid flow therethrough while permitting gas flow therethrough, the surfaces of vent capillaries 5855 are also preferably rendered hydrophobic using a vapor phase silation. In yet another embodiment, a hydrophobic vent is made of porous silicon which is made hydrophobic using a vapor phase silation. In yet other embodiments, the hydrophobic vent can be made from a CVD deposited film of either silicon nitrite or polycrystaline silicon with a series of holes etched therein using either photolithography, particle-track etching or chemical etching. A silicon oxide layer can optionally be applied, covered with a thin film such as CVD polycristalline silicon or silicon nitride and then removed with a chemical etch such that the capillary dimension can be defined by the silicon oxide thickness. Alternatively, anisotropic etching can be carried out in a KOH solution.

19. Low Dead Volume Valves

Several limitations exist when using miniaturized diaphragm type valves to control the movement of liquid plugs through various reaction chambers and channels. For example, the dead volumes of the inlet and outlet ports to the valve become significant and adversely affect the control of the liquid at such low volumes. The relatively large area of the flexible diaphragm contacting such liquid further complicates this problem.

Figure 48:
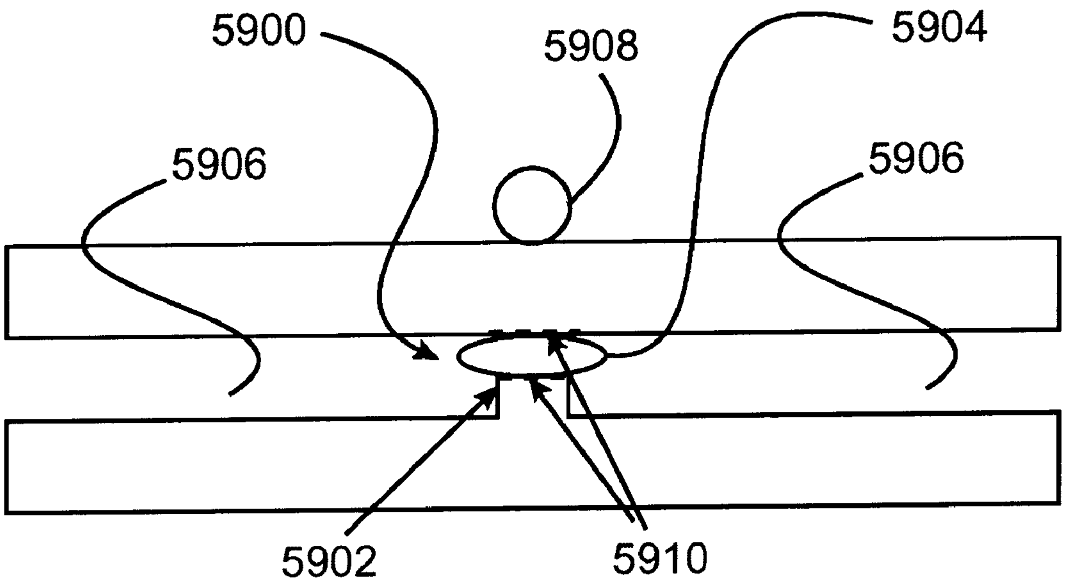
FIG. 48 illustrates a sectional side view of a microfluidic particle suspension valving arrangement having minimal dead volume.

In an additional embodiment of the present invention, as is shown in the sectional view of FIG. 48, a microfluidic particle suspension valving arrangement 5900 having minimal dead volume and diaphragm contact area is provided, thus overcoming the above limitations. In valving arrangement 5900, an emulsion of particles 5902 is suspended in a liquid which is immiscible with water, [for example, magnetic particles being suspended in oil]. Alternatively, the emulsion can be replaced by a large polymer linked to the particles. As is shown in the side sectional view of FIG. 48, the emulsion is positioned to be trapped in a shallow hydrophobic region 5904 which occludes a flow channel 5906. When valving arrangement 5900 is in an "open" position, fluid and gas flow past the occluding emulsion by temporarily displacing the emulsion. By applying a magnetic field by way of magnet 5908, [or alternately by applying an electric field], the viscosity of emulsion 5902 is dramatically increased and occludes gas and fluid passage through flow channel 5906.

In a first embodiment, comprising a magnetic device, the emulsion is either an oil based ferrofluid, or coated paramagnetic beads in silicon oil, fluorinert, or mineral oil. The magnetic field is modulated at the valve location by using a coil or by moving the magnet relative to the valve location. The magnetic field causes alignment and linking of the magnetic beads which increases the fluid viscosity and interrupts flow.

In an alternative embodiment, comprising an electrorheological device, the emulsion comprises particles with a high dielectric constant, [for example, lead-zirconium-titanate, nickel or corn starch], suspended in silicon oil, fluorinert, or mineral oil. An electric field is applied through insulated electrodes 5910 which are preferably fabricated within the valve portion of the channel.

In alternate embodiments, valving arrangement 5900 can be made of silicon or glass, and the valve region can be made fully or selectively hydrophobic with two hydrophobic regions separated by a hydrophillic zone. In this approach, an aqueous plug can be used as the high dielectric emulsion. In alternative embodiments, electrodes 5910 can be made of polycrystaline silicon insulated with CDV deposited silicon oxide or silicon nitrite or alternatively be fabricated in the silicon using doping and passivated by thermally grown oxide.

Using either of the above magnetic or electrorheological valving arrangements, a valve array can be fabricated by combining several of these devices in parallel.

20. Electronic Detection of Binding Using Tethered Particles

Figure 49:
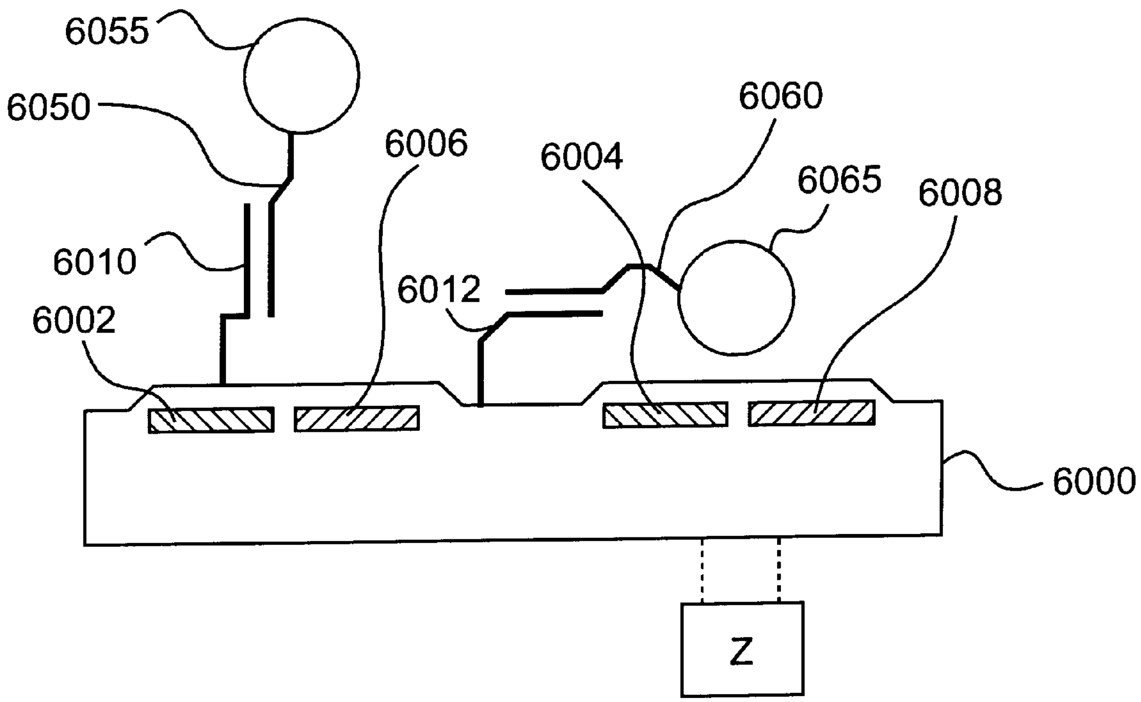
FIG. 49 illustrates a device for direct electronic detection of hybridization locations on an oligonucleotide probe array.
Figure 50:
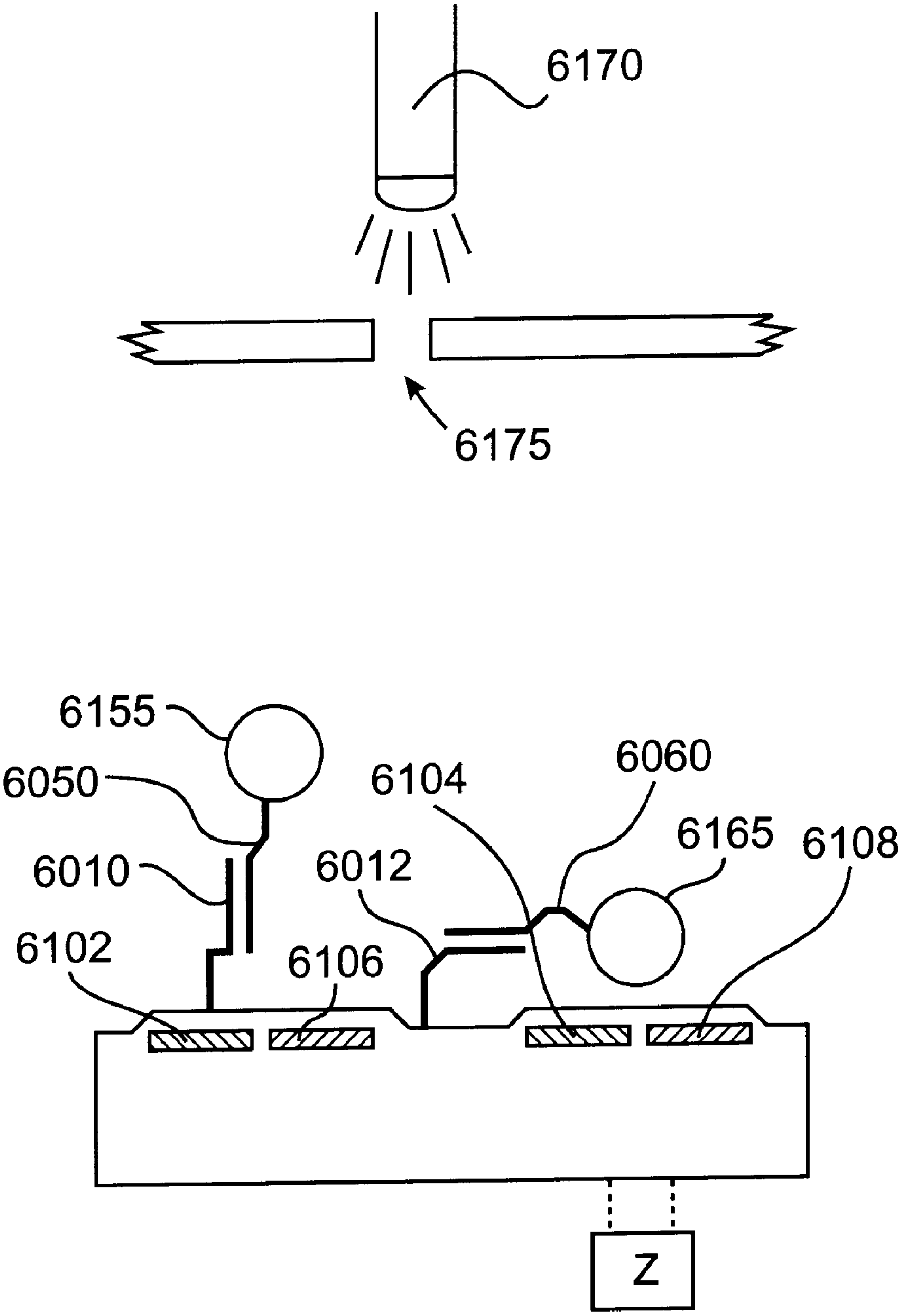
FIG. 50 illustrates the device of FIG. 49, further comprising a laser or light source for modifying particle impedance.

In an alternative embodiment of the present invention, as shown in FIGS. 49 and 50, direct electronic detection of the hybridization is achieved, as follows. A substrate 6000 has an oligonucleotide probe array positioned thereon. [For ease of illustration, a close-up view of the region containing only two of the individual probes in this array, being probes 6010 and 6012, is shown.] A series of active electrodes 6002 and 6004 and common electrodes 6006 and 6008 are positioned proximal probes 6010 and 6012, respectively, as shown. Unknown target sequences 6050 and 6060 are each tethered to metal particles 6055 and 6065, as shown. Alternatively, the target sequences 6050 and 6060 have a biotin label, and after hybridization, applied thereon with metal particles after hybridization with streptavidin ligands. Hybridization on the array are detected by sensing a shift in the dielectric properties at the locations where the target sequences bind with the probes. In a preferred embodiment, the electrodes are used to measure the complex impedance proximal a location where binding takes place, with the tethered metal particles dramatically changing the impedance between the electrodes. An important advantage of such direct electronic detection of hybridization locations is that it further enables the scanning process to be miniaturized. A further advantage is that the present system can also be adapted to alternately detect antigen-antibody or receptor binding instead of hybridization.

In a preferred embodiment of this system, particles 6055 and 6065 are gold particles, however, platinum or nickel particles may also be used. The relative permitivity of these particles is extremely high compared to the solution. The complex impedance of a target sequence as measured between a pair of electrodes 6002 and 6006 or 6004 and 6008 will shift in the presence of the metallic particles. Some variation will appear in the location of the hybridized particle relative to the electrodes. This is illustrated in FIG. 49 by the relative position of metal particles 6055 and 6065 tethered to unknown target sequences 6050 and 6060, as shown. Accordingly, a distribution of sensitivities exist, with the conformation of metal particle 6065 and target 6060 expected to give a higher signal than the conformation of metal particle 6055 to target 6050.

In a second embodiment of this system, as shown in FIG. 50, the particle conductivity [and thus the measured impedance] of target sequences 6150 and 6160 is modified using a laser or other light source 6170. In this embodiment, semiconductor particles 6155 and 6165 which have a low doping density are tethered to target molecules 6150 and 6160 using known art such as silation or post hybridization staining of biotinalated target as described above. Particles 6155 and 6165 are illuminated by light source 6170 which produces a modulated light, thereby generating carriers in the silicon resulting in a time dependent impedance as measured between electrodes 6102 and 6106 or 6104 and 6108. Conductivity modulation of the semiconductor particles provides the following advantages: (1) increased sensitivity by locking in on the light modulation frequency, and (2) multicolor detection using semiconductor particles with different band gaps. An additional advantage of assisting with spacial localization of binding detection is possible, for example, where a line of electrodes run in one direction and a line of light excitation scans perpendicular to these electrode lines by passing a moving slit opening 6175 over the array.

21. Polycarbonate Target-Preparation Cartridge

Figure 51:
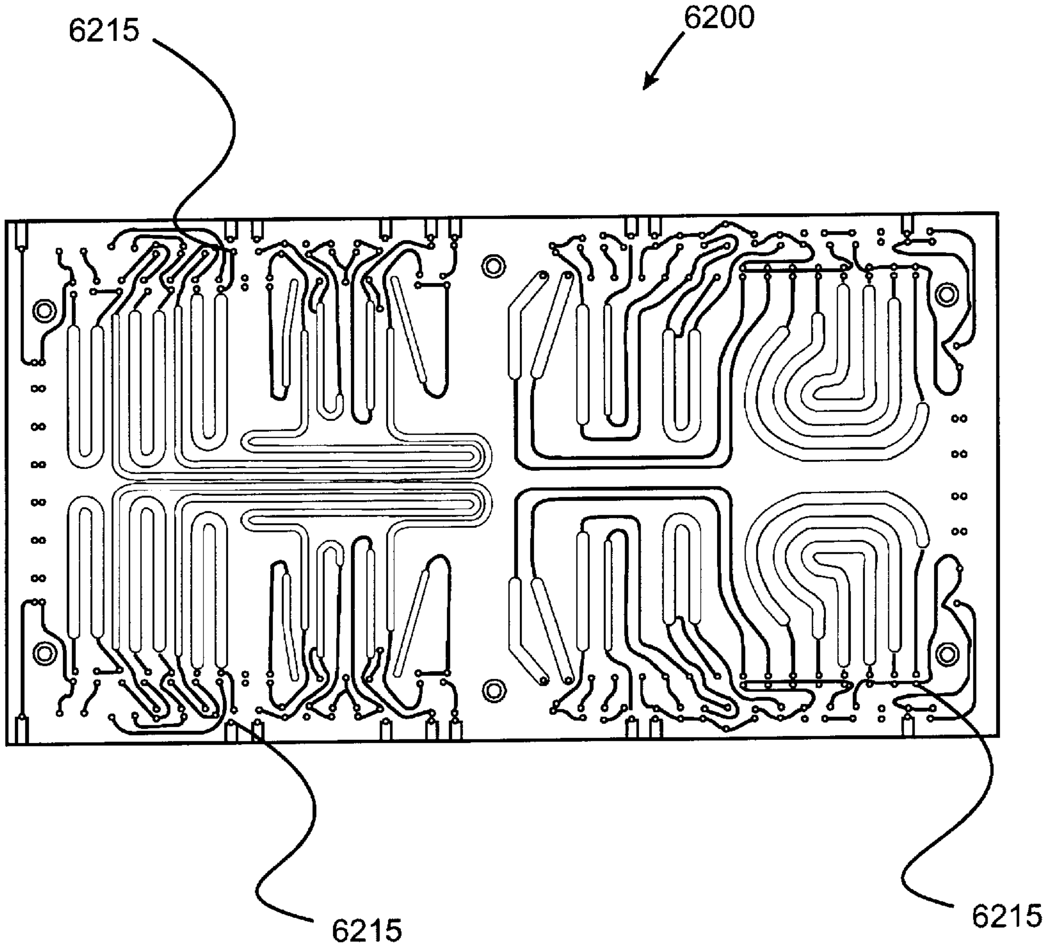
FIG. 51 illustrates a top view of a polycarbonate cartridge for simultaneously performing preparative reactions including PCR, fragmentation, and labeling on four separate samples. PCR reactions.
Figure 52:
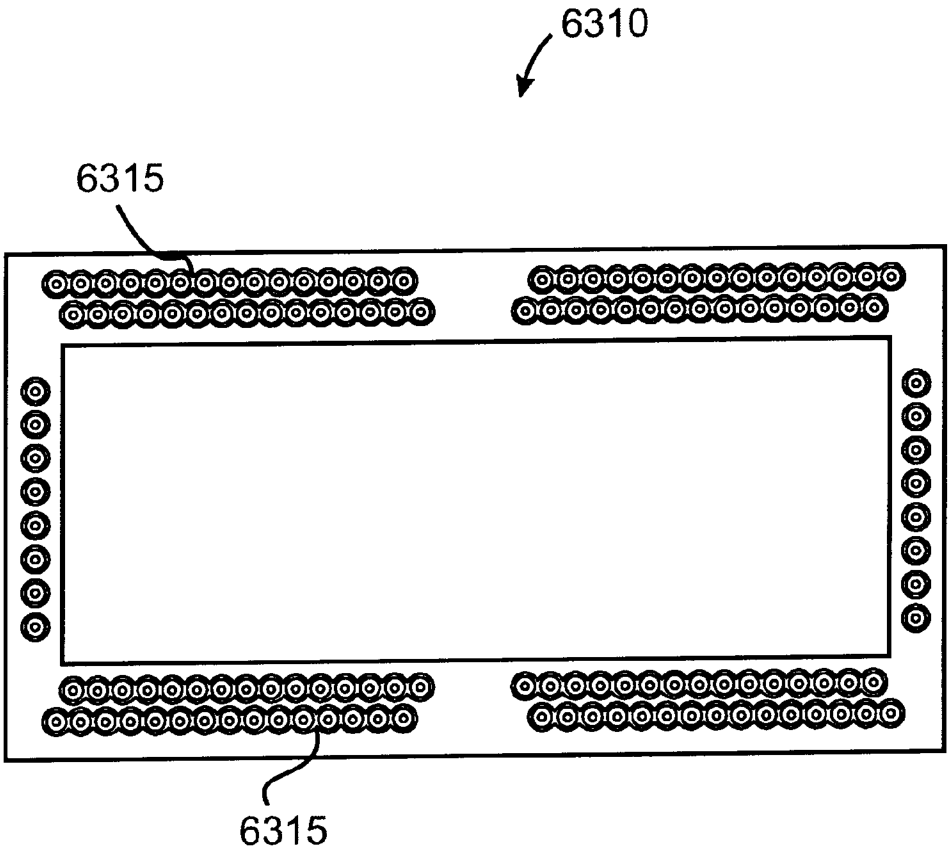
FIG. 52 illustrates a valve plate adapted to cover the polycarbonate cartridge of FIG. 51.

In another aspect of the invention, as shown in FIG. 51, a polycarbonate cartridge 6200 for performing PCR reactions is provided. When operating with associated instrumentation under computer control, the cartridge is adapted to simultaneously perform the following on four different samples: (1) store DNAse/calf alkaline phosphatase (CIAP) reagent mix (at 4° C.), (2) store TdT reagent Mix (4° C.), (3) carry out P450 multiplex PCR, (4) store sample of PCR product, (5) join and mix PCR product with DNAse/CIAP mix, (6) incubate mixture, (7) store sample of reaction product, (8) join and mix reaction product with TdT reagent mix, and (9) incubate mixture.

The polycarbonate cartridge 6200 has plurality of liquid control ports 6215 which are generally disposed around the perimeter of the cartridge, as shown. The polycarbonate cartridge 6200 of FIG. 62 is adapted to be covered by a valve plate 6310 which is shown in FIG. 63. Valve plate 6310 has a plurality of pneumatic ports 6315 disposed therein, as shown. Valve plate 6310 is adapted to be positioned over cartridge 6200 such that each of the valve plate's pneumatic ports 6315 overlap and mate with a liquid control port 6215 of cartridge 6200. Pneumatic ports 6315 can be used either as valves or vents interchangeably.

Figure 53:
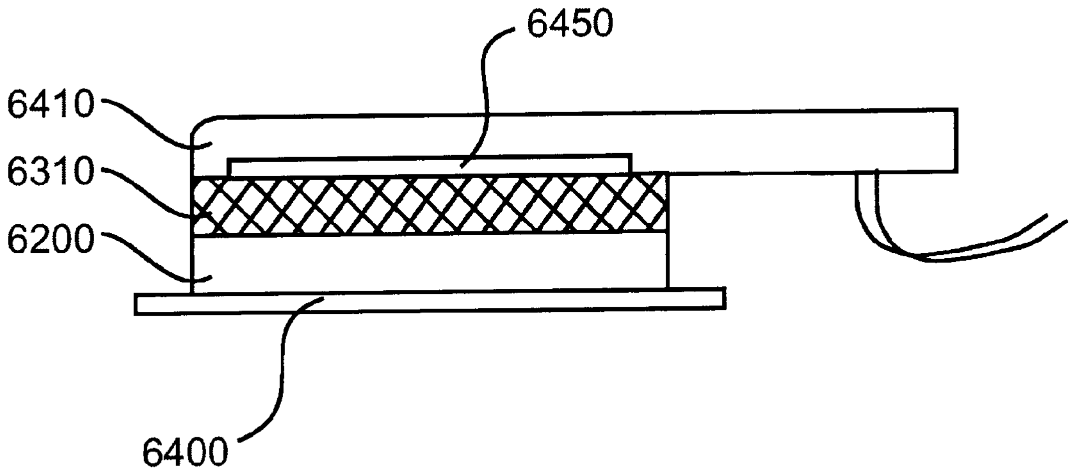
FIG. 53 illustrates a side sectional view of a reaction cartridge sandwiched between the valve plate of FIG. 53 and a temperature control fixture.

As is shown in the sectional side sectional view of FIG. 53, cartridge 6200 is preferably sandwiched between valve plate 6310 and a temperature control fixture 6400. A pneumatic manifold 6410 is positioned over valve plate 6310 and is adapted to individually control the pressure in each of the pneumatic ports 6315. In addition, a sealed air plenum 6450 is formed between manifold 6410 and valve plate 6310. Air plenum 6450 provides both thermal isolation and a downwards pressure force which is desirable for maintaining thermal contact and ensuring cartridge sealing. In one embodiment, air plenum 6450 includes a sealed membrane to prevent gas leakage. In another embodiment, the air plenum is disposed within the valve plate 6310.

Figure 54:
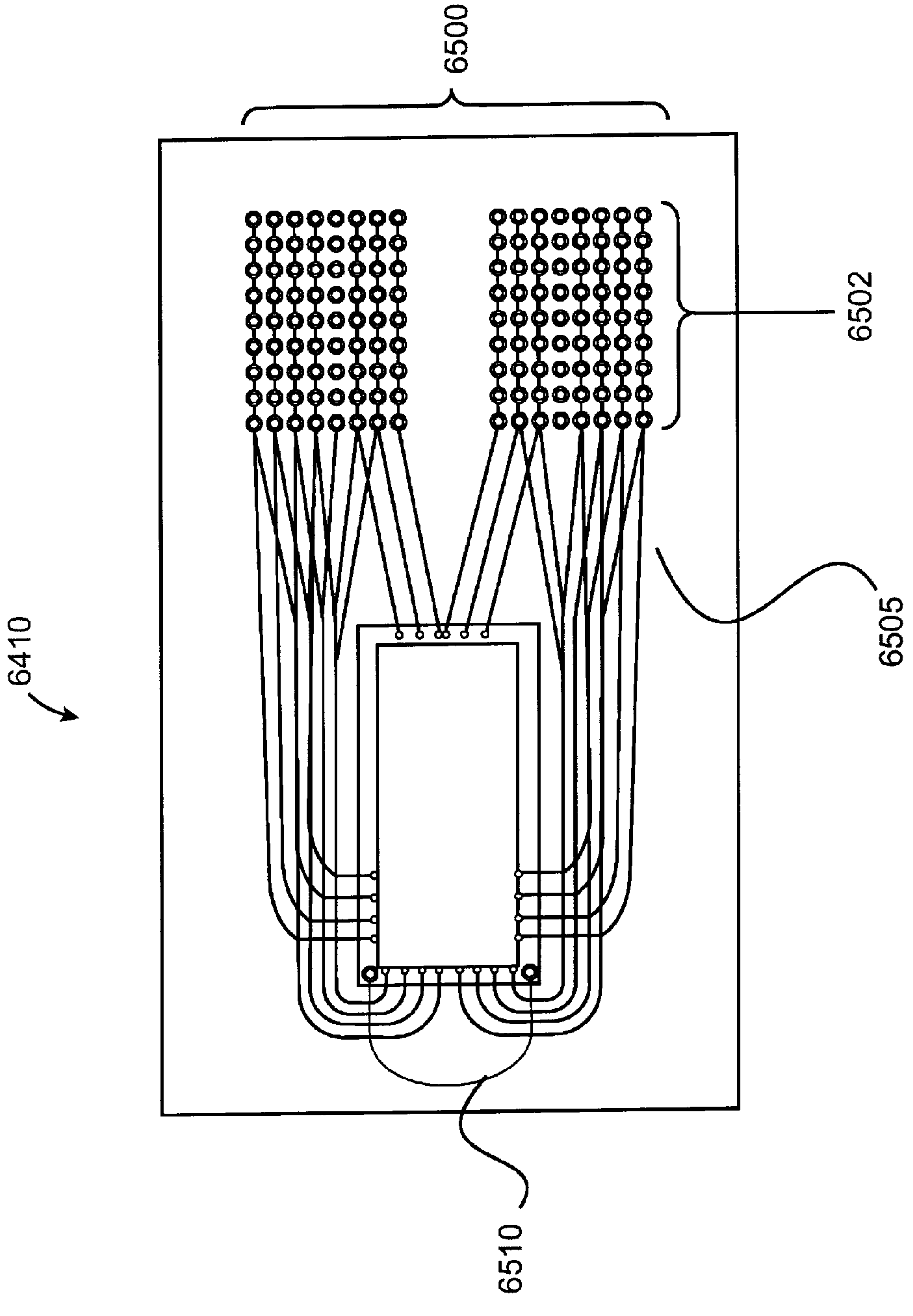
FIG. 54 illustrates a pneumatic manifold for positioning on top of the valve plate of FIG. 52.

FIG. 54 shows a top view of the pneumatic manifold 6410 of FIG. 53. Pneumatic manifold 6410 is preferably comprised of multiple layers of acrylic bonded together so as to form an array of pneumatic input ports 6502 which are individually linked by various channels 6505 to output ports 6510. Pneumatic manifold 6410 is dimensioned such that pneumatic output ports 6510 are adapted mate with the array of pneumatic ports 6315 of valve plate 6300. Accordingly, pneumatic output ports 6510 are adapted to distribute gas through pneumatic ports 6315 of each of valve plate 6300 affecting the liquid control ports 6215 of cartridge 6200.

22. Microfluidic Mixing Using Capillary Recirculation

Figure 55A:
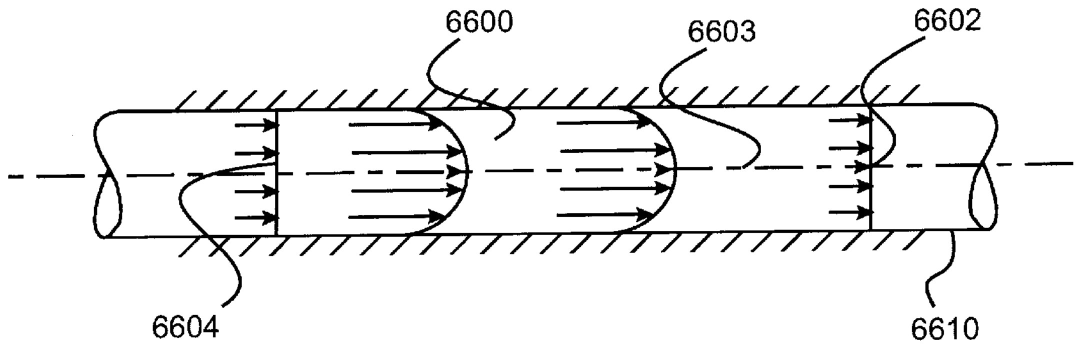
FIG. 55A illustrates a velocity profile in a fluid plug moving through a capillary.

Homogeneous mixing can be critical to the performance of enzymatic and other reactions. Under capillary flow conditions, however, mixing is difficult as turbulent flow is difficult to achieve. Experimentation has revealed that fluid plugs moving through capillaries experience a recirculating flow as shown in FIG. 55A which illustrates a velocity profile in a fluid plug moving through a capillary, and FIG. 55B which illustrates the paths of fluid re-circulation in the fluid plug.

Figure 55B:
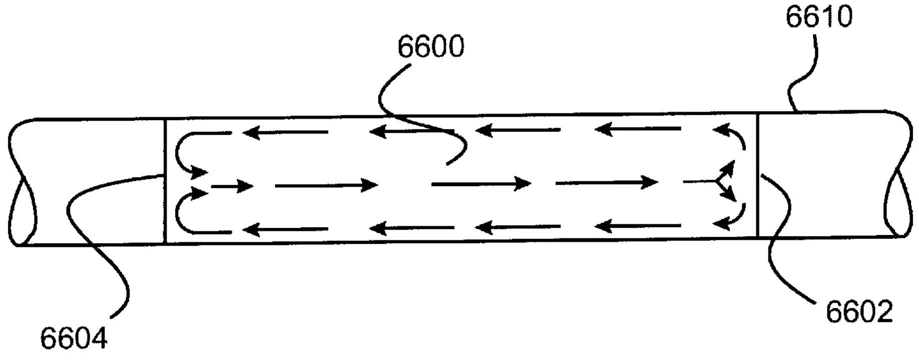
FIG. 55B illustrates paths of fluid re-circulation in a fluid plug moving through a capillary.

The movement of a fluid plug 6600 through a capillary 6610 must have a net uniform velocity at its leading edge 6602 and also at its trailing edge 6604. As is shown in the velocity profile of FIG. 55A, a parabolic profile is approached across the fluid plug away from the leading and trailing edges, with the fluid moving fastest along centerline 6603 of the fluid plug, and progressively slowing as the side edges of the fluid plug are approached. Observation has revealed that the fluid flows radially outward at its leading edge 6602 and radially inward at its trailing edge 6604, as illustrated in FIG. 55B to balance the flow. The recirculation process scales with the length of the fluid plug so that moving the fluid plug a distance equal to half its length will cause a dye initially placed at the fluid plug's leading edge 6602 to move to centerline 6603 of the plug. Similarly, moving fluid plug 6600 a distance equal to its length causes a dye initially placed at leading edge 6602 to move to its trailing edge 6604, or vice versa.

In an embodiment of the present invention, homogeneous mixing of fluid plug 6600 is achieved by moving the fluid plug in a capillary by a distance of greater than three times the plug length. In alternative embodiments, after moving a distance half its length, fluid plug 6600 can be moved through a narrow portion of a capillary such that hydrodynamic focussing will take place, thereby creating smaller lamina in the laminar fluid flow. By ensuring the residence time in the narrowed region is of sufficient duration, specifically being $x^2/D$, where x is the lamina half distance and D is the diffusivity of the reagent, good reagent mixing can be achieved.

23. Silicone and Parylene Coating of Polymeric Enzyme-Reaction Cartridges

In another embodiment of the present invention, PCR reactions are enhanced when carried out in reaction chambers fabricated from polycarbonate plate, and coated with silicon and parylene, as follows.

A polymeric, (eg: polycarbonate), cartridge is preferably first cleaned with detergent and rinsed with deionized water and dried either in an oven at approximately 90° C. or by blowing with nitrogen. The milled sides of the cartridge are then covered by tape and then annealed in an oven, preferably at about 90° C. Thereafter, the cartridge can then be coated in silicone, [preferably being one part silicone RTV adhesive (eg: Dow Corning 3140) diluted in three parts hexane], then heated to 90° C. under vacuum conditions for about 15 minutes. Alternatively, the cartridge can be coated by a layer of parylene, preferably being in the range of 1 to 100 microns, and more preferably in the range of 5 to 20 microns, and most preferably in the range of 10 to 15 microns in thickness.

Using such a polycarbonate cartridge coated with silicone and parylene, respectively, a PCR reaction was carried out for Cyp450 multiplex PCR comprising: an initial departure step of 95° C. for 3 minutes, 45 cycles of 95° C. for 45 seconds, 65° C. for 25 seconds and 72° C. for 35 seconds. The extension step of 72° C. was increased by one second after each cycle. The ramping time from annealing (65° C.) to extension (72° C.) was set at 5% for about 40 seconds. Agarose gel (2%) electrophoresis was used to separate DNA bands. The signals were recorded after staining the gel with ethidium bromide. The yield of the cartridge were found to improve significantly as compared to that carried out in PCR in standard format.

Alternatively, a thin-flim polymer is attached to the cartridge using adhesive or heat lamination in place of adhesive tape.

24. Deformable Reaction Chambers

In another aspect of the present invention, as shown in the side sectional view of FIG. 16, and the top plan vies of FIGS. 17A and 17B, a deformable chamber device 1700 having a pneumatic portion 1701 and a fluid portion 1703 is provided. A plurality of reaction chambers 1702, 1704, 1706 and 1708 are formed in fluid portion 1703, as shown. Chambers 1702, 1704, 1706 and 1708 are provided with various fluid input/output channels 1801, enabling fluid to enter and exit these chambers. Pneumatic portion 1701 and a fluid portion 1703 are bonded together, with a deformable member 1705, which is preferably fabricated from polypropelene or laytex, being disposed therebetween, acting as a flexible chamber wall which seals the pneumatic chamber. Pneumatic chambers 1722, 1724, 1726 and 1728 are provided in pneumatic portion 1701. These pneumatic chambers 1722, 1724, 1726 and 1728 are positioned directly over each of reaction chambers 1702, 1704, 1706 and 1708, respectively, with deformable member 1705 sealing these chambers.

As pneumatic chambers 1722, 1724, 1726 and 1728 are each pneumatically addressed, the respective portion of deformable member 1705 disposed within and thus sealing reaction chambers 1702, 1704, 1706 and 1708 will move such that the volume of these chambers can be controllably altered. Accordingly, to move fluid into a selected chamber, the pressure is decreased in its corresponding addressable port such that the deformable member moves to cause the volume of the chamber to increase. As such, fluid can be drawn into the reaction chambers through channel 1803. Inversely, to remove fluid from a reaction chamber, the pressure is increased in its corresponding pneumatic chamber such that the deformable member moves to cause the volume of the chamber to decrease. As such, fluid can be expelled from the reaction chamber through various channels 1803.

IV. Applications

The various reaction chambers and cartridge systems set forth in the present invention, including those made from polycarbonate, polypropylene, silicon and glass and coated with parylene, silicone, and silicon nitride of the present invention may be used for a variety of enzymatic reactions. In these reactions, templates, primers and monomers may be unlabeled, labeled, or analogs. Templates and primers may be in solution or tethered to a surface of the base cartridge.

For example, the microfluidic devices described above have been used to carry out RNA polymerization, i.e., reverse and in vitro transcription. In other embodiments, RNA modification has been carried out in microfluidic devices, such as Poly A polymerase (AMP added to 3' end of RNA, can be used for labeling), polynucleotide kinase (transfer gamma-phosphate of ATP to 5' of DNA or RNA, can be used for labeling) and alkaline phosphatase (removes free 5'OH). RNA fragmentation, such as RNA-DNA duplex nicking (e.g., RNAase H) and RNAase digestion has also been carried out.

In other embodiments of the present invention, DNA polymerization has been carried out with the microfluidic devices described above. Examples of such polymerization include isothermal amplification (NASBA, 3SR, etc), PCR amplification (deep vent, amplitaq gold, taq) and cycle sequencing amplification (with labeled dideoxy terminators, or with labeled primers (e.g., energy transfer dyes). In addition, DNA modification, such as terminal deoxytransferase (TdT), ligation (including chimeric ligation with RNA) and alkaline phosphatase (removes free 5'OH). Other DNA applications includes DNA fragmentation, such as double stranded DNA (DNAase or restriction endonucleases) or single stranded DNA (nuclease S1) and peptide manipulation, such as in vitro translation and protease digestion.

The device and system of the present invention has a wide variety of uses in the manipulation, identification and/or sequencing of nucleic acid samples. These samples may be derived from plant, animal, viral or bacterial sources. For example, the device and system of the invention may be used in diagnostic applications, such as in diagnosing genetic disorders, as well as diagnosing the presence of infectious agents, e.g., bacterial or viral infections. Additionally, the device and system may be used in a variety of characterization applications, such as gene expression, forensic analysis, e.g., genetic fingerprinting, bacterial, plant or viral identification or characterization, e.g., epidemiological or taxonomic analysis, and the like.

Although generally described in terms of individual devices, it will be appreciated that multiple devices may be provided in parallel to perform analyses on a large number of individual samples. Because the devices are miniaturized, reagent and/or space requirements are substantially reduced. Similarly, the small size allows automation of sample introduction process using, e.g., robot samplers and the like.

In preferred aspects, the device and system of the present invention is used in the analysis of human samples. More particularly, the device is used to determine the presence or absence of a particular nucleic acid sequence within a particular human sample. This includes the identification of genetic anomalies associated with a particular disorder, as well as the identification within a sample of a particular infectious agent, e.g., virus, bacteria, yeast or fungus.

The devices of the present invention may also be used in de novo sequencing applications. In particular, the device may be used in sequencing by hybridization (SBH) techniques. The use of oligonucleotide arrays in de novo SBH applications is described, for example, in U.S. application Ser. No. 08/082,937, filed Jun. 25, 1993, now abandoned.

EXAMPLES

Example 1

Extraction and Purification of Nucleic Acids

In separate experiments, HIV cloned DNA was spiked into either horse blood or a suspension of murine plasmacytoma fully differentiated B-cells derived from BALBc mice. Guanidine isothiocyanate was added to a concentration of 4 M, to lyse the material. In separate experiments, the lysate was passed through a cartridge containing glass wool (20 $\mu$l), a cartridge with soda glass walls (20 $\mu$l), and a glass tube. After 30 minutes at room temperature, the remaining lysate was washed away with several volumes of ethanol:water (1:1) and the captured DNA was eluted at 60° C. using 1× TBE. The yield of eluted DNA was measured using ethidium bromide staining on an agarose gel, and purity was tested by using the eluted material as a template for a PCR reaction. Elution yields ranged from 10% to 25% and PCR yields ranged from 90 to 100% as compared to controls using pure template.

Example 2

RNA Preparation Reactions in Miniaturized System

A model miniature reactor system was designed to investigate the efficacy of miniaturized devices in carrying out prehybridization preparative reactions on target nucleic acids. In particular, a dual reaction chamber system for carrying out in vitro transcription and fragmentation was fabricated. The device employed a tube based structure using a polymer tubing as an in vitro transcription reactor coupled to a glass capillary fragmentation reactor. Reagents not introduced with the sample were provided as dried deposits on the internal surface of the connecting tubing. The experiment was designed to investigate the effects of reaction chamber materials and reaction volume in RNA preparative reaction chambers.

The sample including the target nucleic acid, DNA amplicons containing a 1 kb portion of the HIV gene flanked with promoter regions for the T3 and T7 RNA primers on the sense and antisense strands, respectively, RNA polymerase, NTPs, fluorinated UTP and buffer, were introduced into the reactor system at one end of the tubing based system. In vitro transcription was carried out in a silicone tubing reactor immersed in a water bath. Following this initial reaction, the sample was moved through the system into a glass capillary reactor which was maintained at 94° C., for carrying out the fragmentation reaction. The products of a representative time-course fragmentation reaction are shown in the gel of FIG. 10A. In some cases, the tubing connecting the IVT reactor to the fragmentation reactor contained additional $MgCl_2$ for addition to the sample. The glass capillary was first coated with BSA to avoid interactions between the sample and the glass. Following fragmentation, the sample was hybridized with an appropriately tiled oligonucleotide array, as described above. Preparation using this system with 14 mM $MgCl_2$ addition resulted in a correct base calling rate of 96.5%. Omission of the $MgCl_2$ gave a correct base calling rate of 95.5%.

A similar preparative transcription reaction was carried out in a micro-reaction chamber fabricated in polycarbonate. A well was machined in the surface of a first polycarbonate part. The well was 250 $\mu$m deep and had an approximate volume of 5 $\mu$l. A second polycarbonate part was then acoustically welded to the first to provide a top wall for the reaction chamber. The second part had two holes drilled through it, which holes were positioned at opposite ends of the reaction chamber. Temperature control for the transcription reaction was supplied by applying external temperature controls to the reaction chamber, as described for the tubing based system. 3 $\mu$l samples were used for both transcription and fragmentation experiments.

Figure 9A:
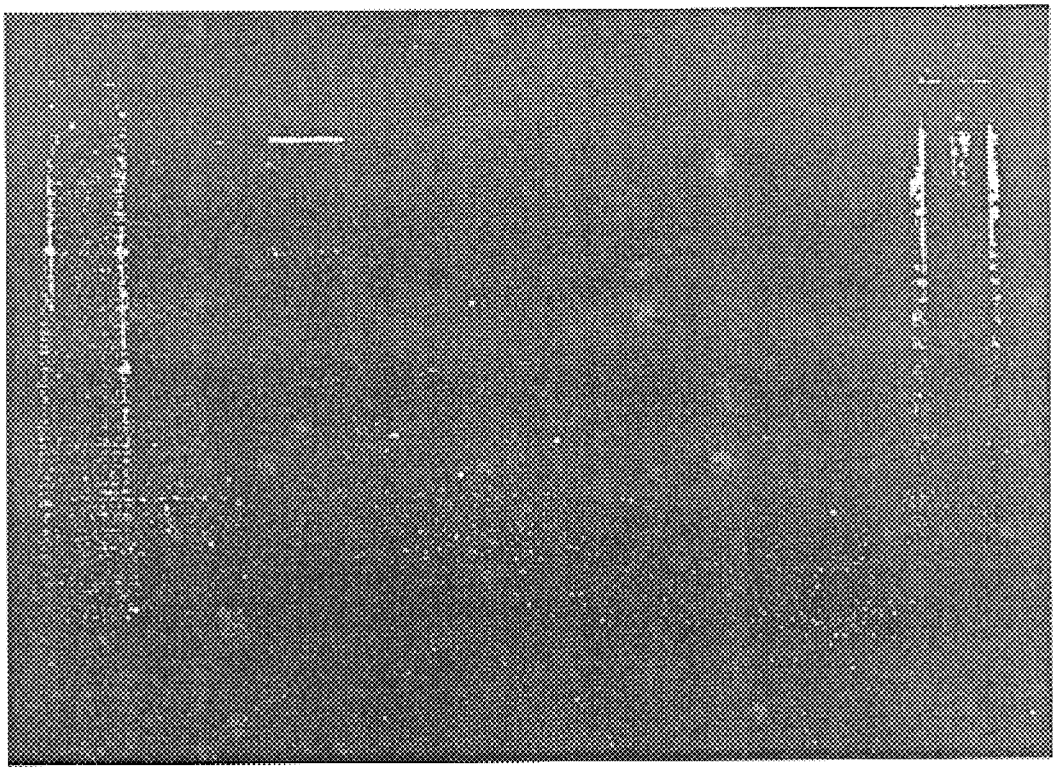
FIG. 9A is a gel showing a time course of an RNA fragmentation reaction.
Figure 9B:
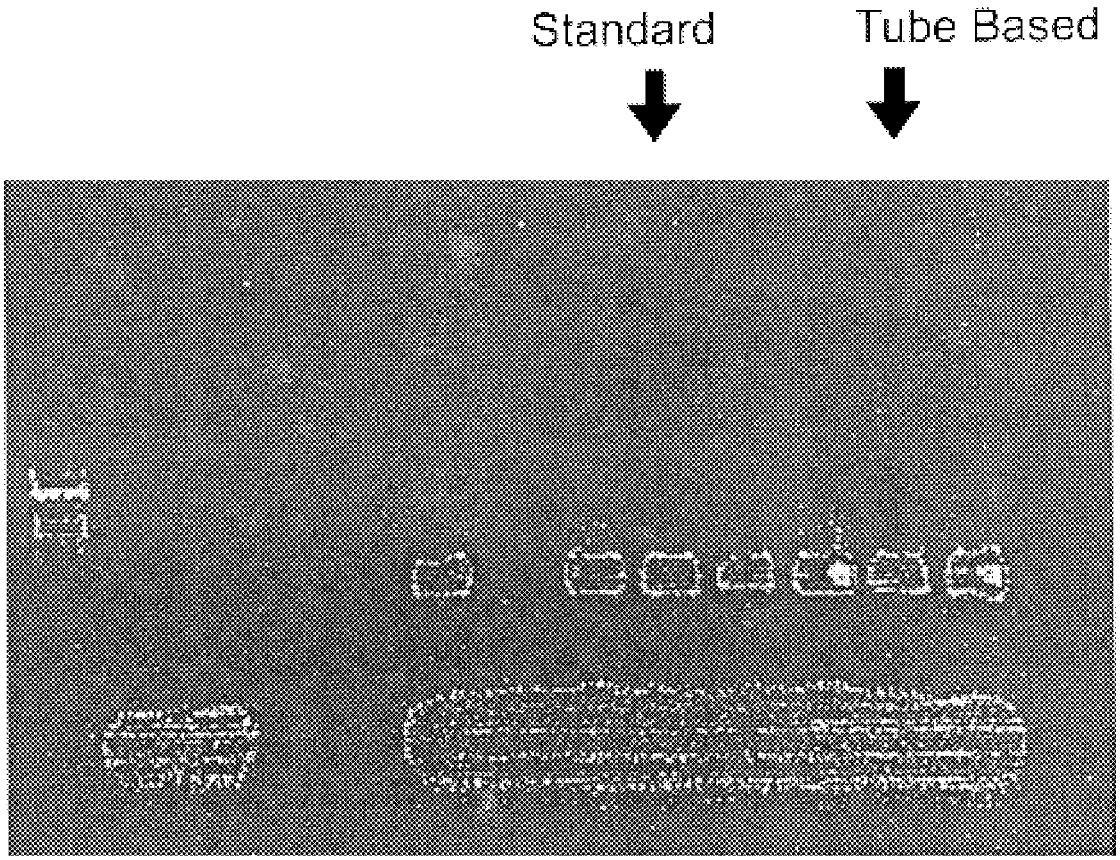
FIG. 9B is a gel showing a comparison of the product of an in vitro transcription reaction in a microchamber vs. a control (test tube).

Transcription reactions performed in the micro-reactor achieved a 70% yield as compared to conventional methods, e.g., same volume in microfuge tube and water bath or PCR thermal cycler. A comparison of in vitro transcription reaction products using a microchamber versus a larger scale control are shown in FIG. 9B.

Example 3

PCR Amplification in Miniaturized System

The miniature polymeric reaction chamber similar to the one described in Example 2 was used for carrying out PCR amplification. In particular, the chamber was fabricated from a planar piece of polycarbonate 4 mm thick, and having a cavity measuring 500 $\mu$m deep machined into its surface. A second planar polycarbonate piece was welded over the cavity. This second piece was only 250 $\mu$m thick. Thermal control was supplied by applying a peltier heater against the thinner second wall of the cavity.

Figure 9C:
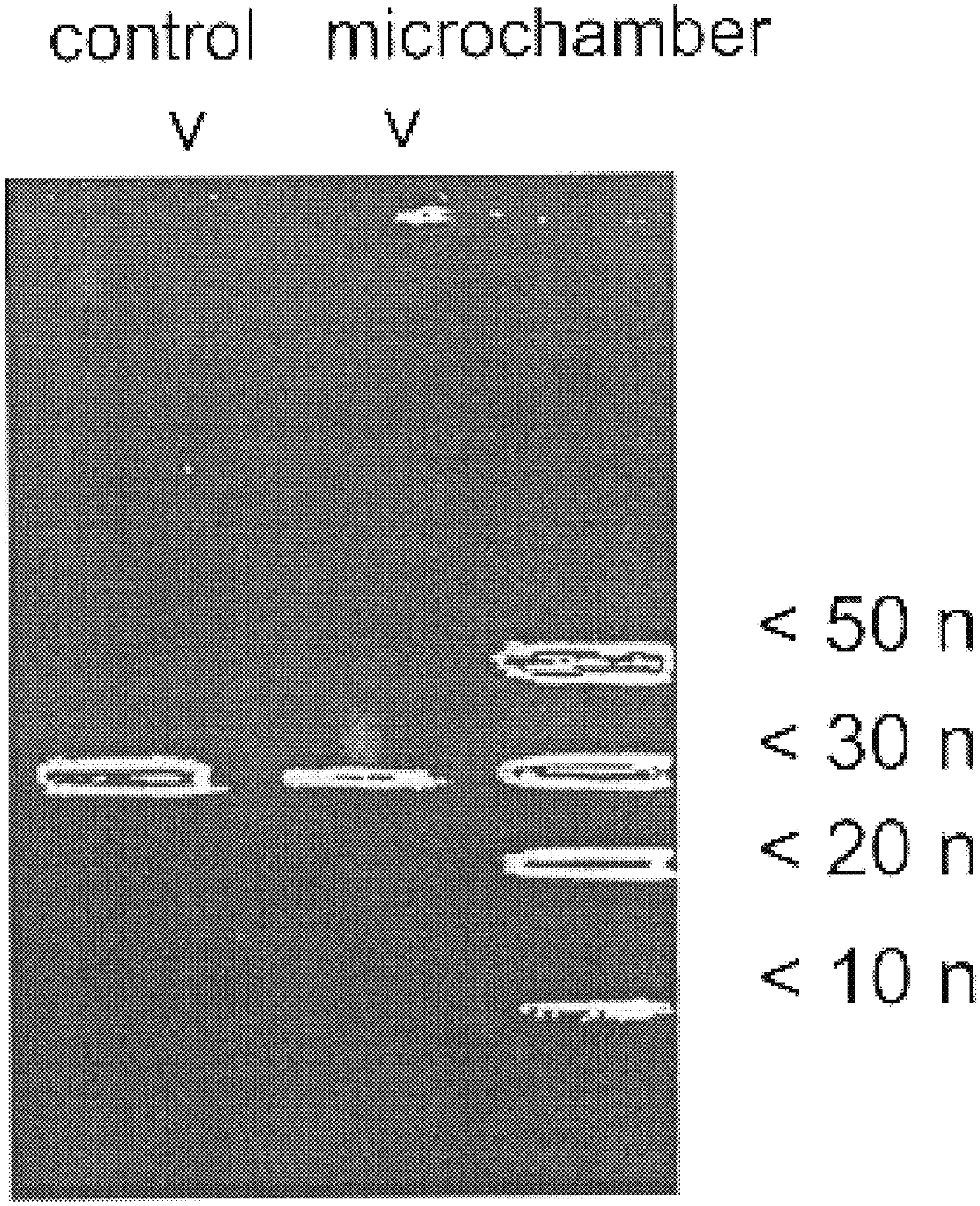
FIG. 9C is a comparison of the PCR product produced in a PCR thermal cycler and that produced by a microreactor.

Amplification of a target nucleic acid was performed with Perkin-Elmer GeneAmp® PCR kit. The reaction chamber was cycled for 20 seconds at 94° C. (denaturing), 40 seconds at 65° C. (annealing) and 50 seconds at 72° C. (extension). Amplification of approximately $10^9$ was shown after 35 cycles. FIG. 9C shows production of amplified product in the microchamber as compared to a control using a typical PCR thermal cycler.

Example 4

System Demonstration, Integrated Reactions

Figure 14A:
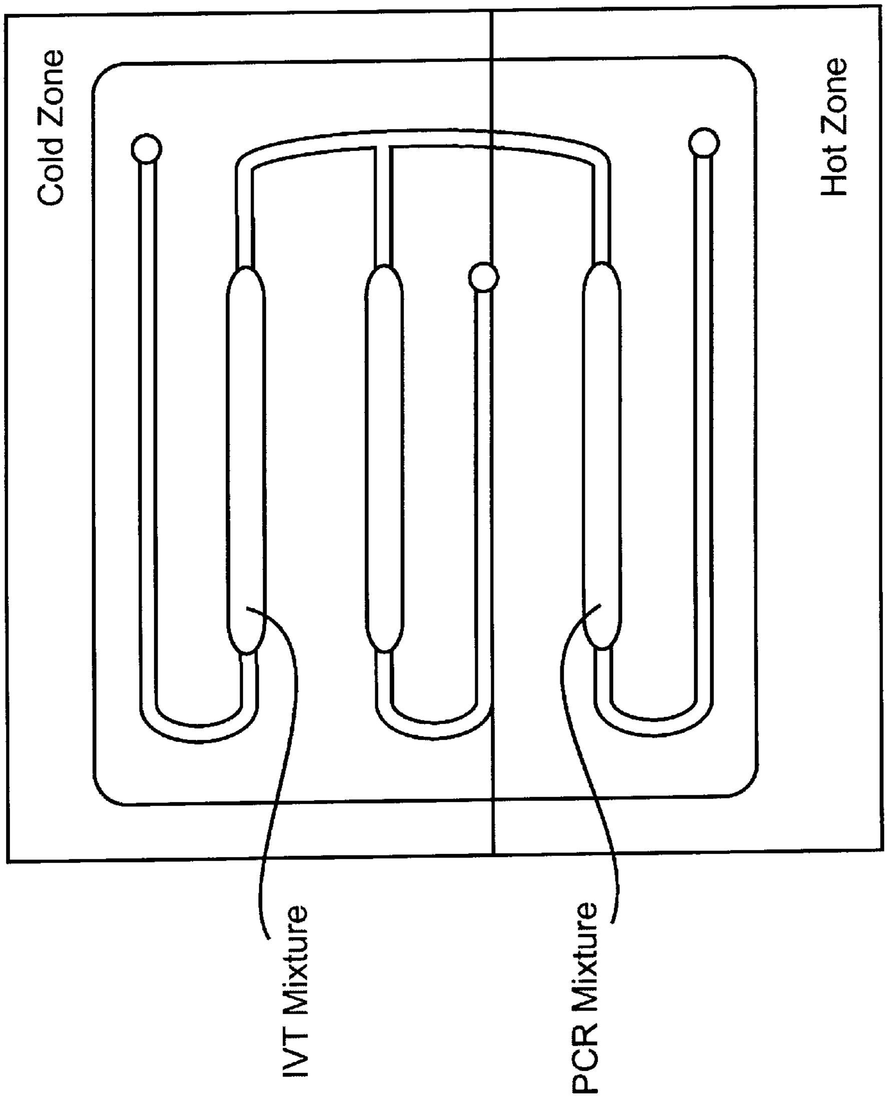
FIG. 14A shows the layout of the device including the thermal configuration of the device.

A microfabricated polycarbonate device was manufactured having the structure shown in FIG. 14A. The device included three discrete vented chambers. Two of the chambers (top and middle) were thermally isolated from the PCR chamber (bottom) to prevent any denaturation of the RNA polymerase used in IVT reactions at PCR temperatures. Thermal isolation was accomplished by fabricating the chambers more than 10 mm apart in a thin polycarbonate substrate and controlling the temperatures in each region through the use of thermoelectric temperature controllers, e.g., peltier devices.

The reactor device dimensions were as follows: channels were 250 $\mu$m wide by 125 $\mu$m deep; the three reaction chambers were 1.5 mm wide by 13 mm in length by 125 to 500 $\mu$m deep, with the reactor volumes ranging from 2.5 to 10 $\mu$l. Briefly, PCR was carried out by introducing 0.3 units of Taq polymerase, 0.2 mM dNTPs, 1.5 mM $MgCl_2$, 0.2 $\mu$M primer sequences, approximately 2000 molecules of template sequence and 1× Perkin-Elmer PCR buffer into the bottom chamber. The thermal cycling program included (1) an initial denaturation at 94° C. for 60 seconds, (2) a denaturation step at 94° C. for 20 seconds, (3) an annealing step at 65° C. for 40 seconds, (4) an extension step at 72° C. for 50 seconds, (5) repeated cycling through steps 2–4 35 times, and (6) a final extension step at 72° C. for 60 seconds.

Following PCR, 0.2 $\mu$l of the PCR product was transferred to the IVT chamber (middle) along with 9.8 $\mu$l of IVT mixture (2.5 mM ATP, CTP, GTP and 0.5 mM UTP, 0.25 mM Fluorescein-UTP, 8 mM $MgCl_2$, 50 mM HEPES, 1× Promega Transcription Buffer, 10 mM DTT, 1 unit T3 RNA polymerase, 0.5 units RNAguard (Pharmacia)) that had been stored in a storage chamber (top). Fluid transfer was carried out by applying pressure to the vents at the termini of the chambers. IVT was carried out at 37° C. for 60 minutes.

Figure 14B:
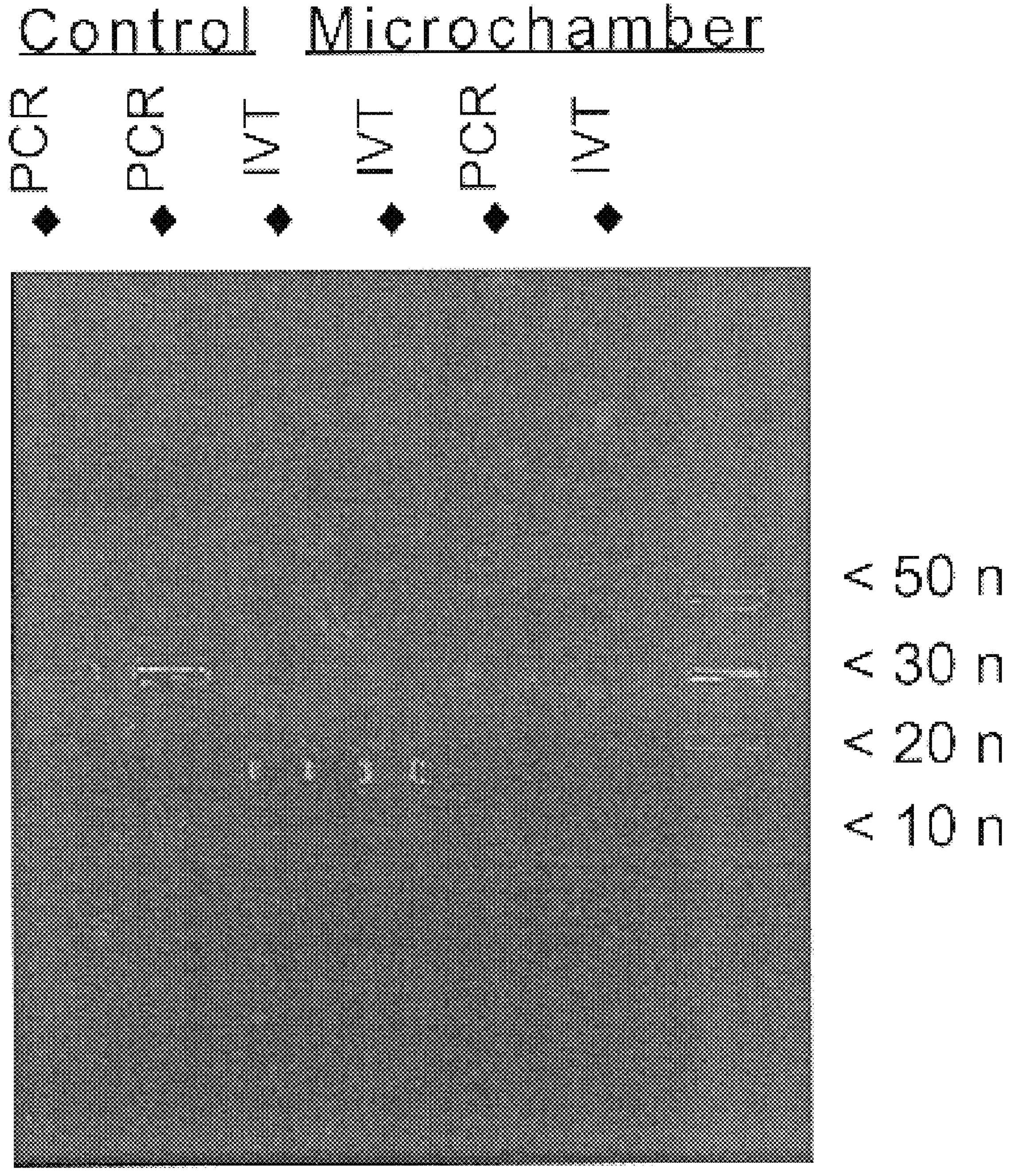
FIG. 14B shows the results of PCR amplification and subsequent in vitro transcription within the chambers of the device.

The results of PCR and IVT are shown in FIG. 14B, compared with control experiments, e.g., performed in eppendorf tubes.

Example 5

Acoustic Mixing

The efficacy of an acoustic element for mixing the contents of a reaction chamber was tested. A 0.5"×0.5"×0.04" crystal of PZT-5H was bonded to the external surface of a 0.030" thick region of a planar piece of delrin which had cavity machined in the surface opposite the PZT element. An oligonucleotide array synthesized on a flat silica substrate, was sealed over the cavity using a rubber gasket, such that the surface of the array having the oligonucleotide probes synthesized on it was exposed to the cavity, yielding a 250 $\mu$l reaction chamber. The PZT crystal was driven by an ENI200 High Frequency Power Supply, which is driven by a function generator from Hewlett Packard that was gated by a second function generator operated at 1 Hz.

Figure 7B:
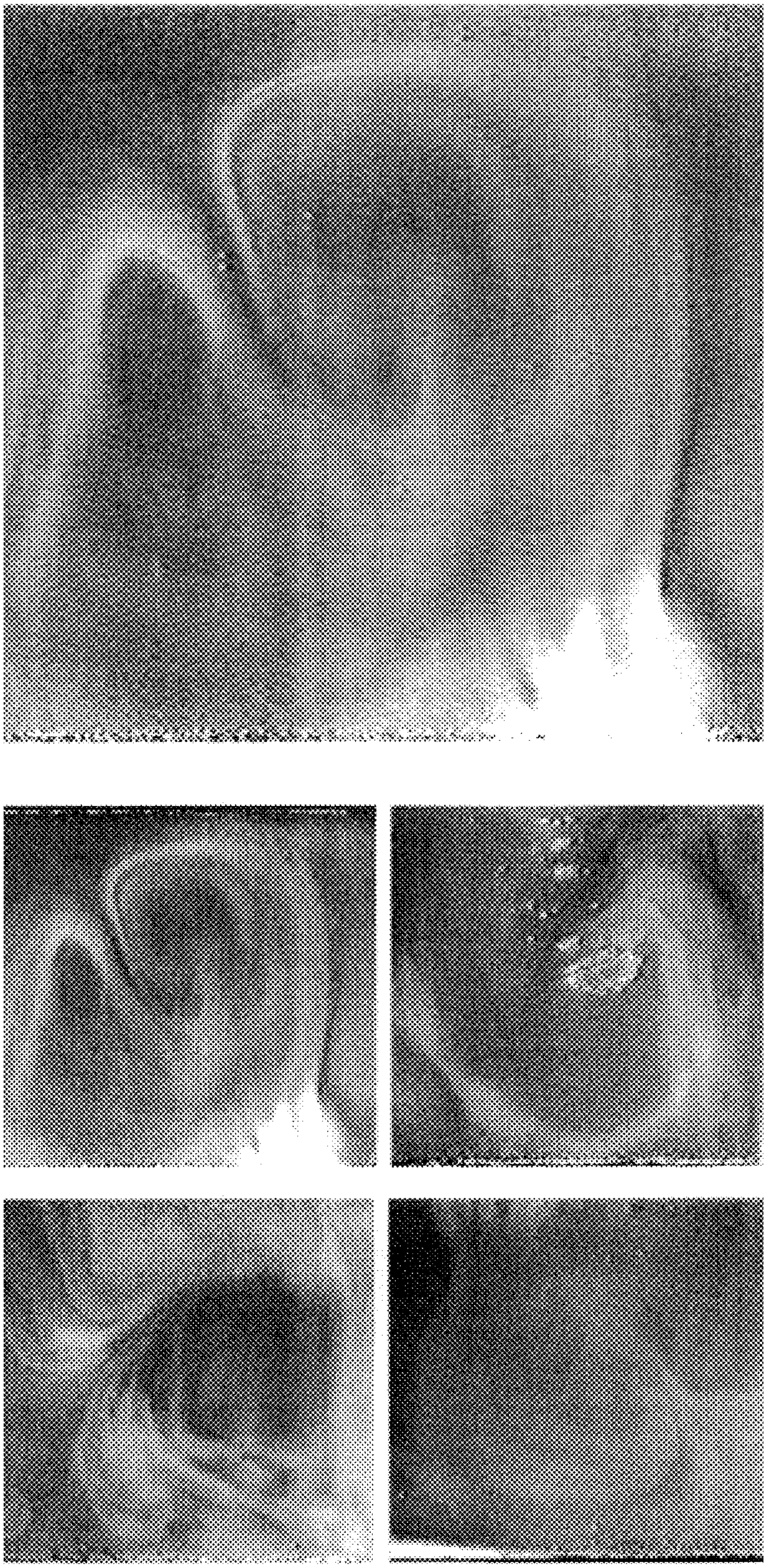
FIG. 7B shows mixing within a reaction chamber applying the PZT mixing element as shown in FIG. 7A.
Figure 7C:
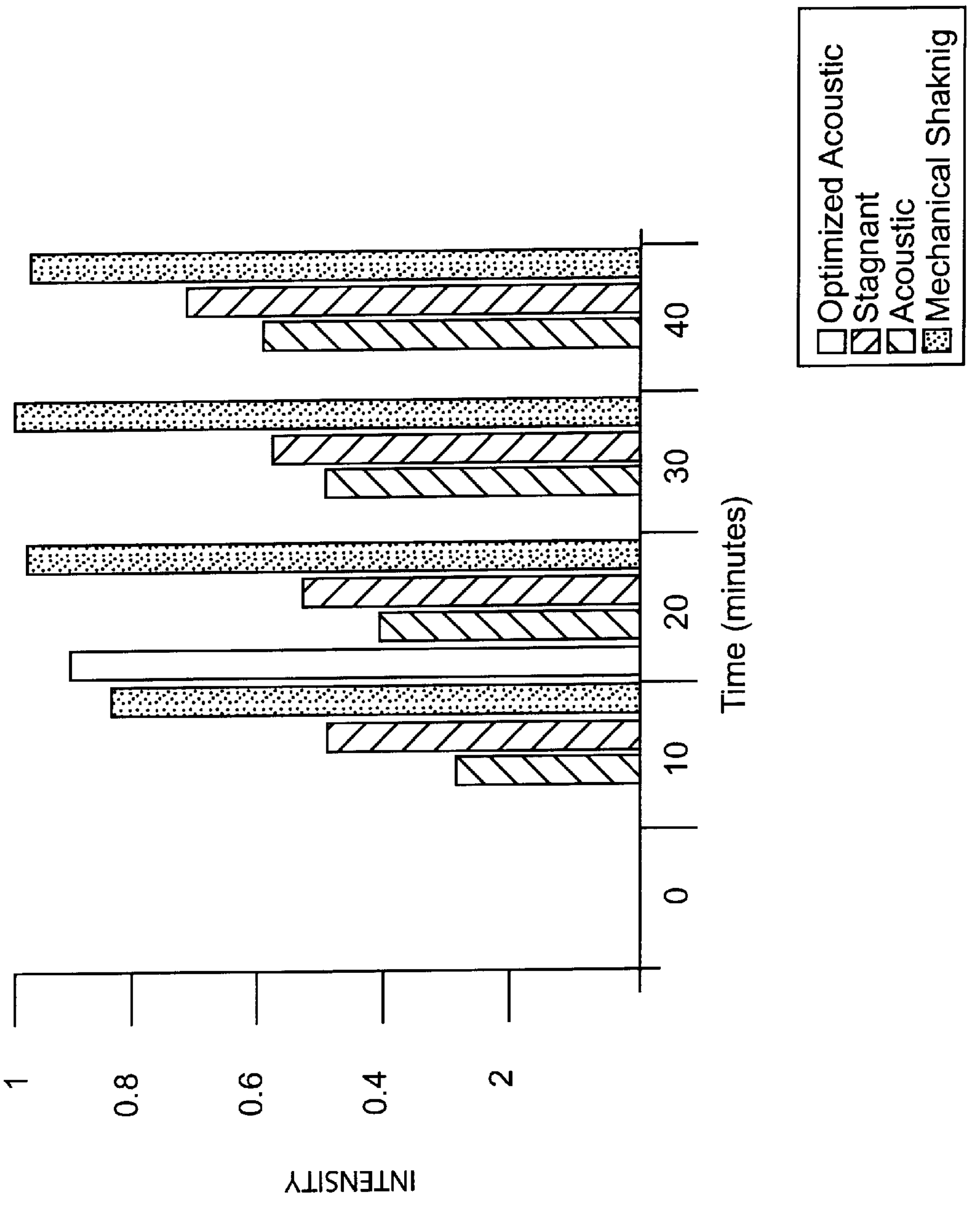
FIG. 7C is a bar graph showing a comparison of hybridization intensities using mechanical mixing, acoustic mixing, stagnant hybridization and optimized acoustic mixing.

In an initial test, the chamber was filled with deionized water and a small amount of 2% milk was injected for visualization. The crystal was driven at 2 MHZ with an average power of 3 W. Fluid velocities within the chamber were estimated in excess of 1 mm/sec, indicating significant convection. A photograph showing this convection is shown in FIG. 7B.

The efficacy of acoustic mixing was also tested in an actual hybridization protocol. For this hybridization test, a fluorescently labeled oligonucleotide target sequence having the sequence 5'-GAGATGCGTCGGTGGCTG-3' and an array having a checkerboard pattern of 400 μm squares having complements to this sequence synthesized thereon, were used. Hybridization of a 10 nM solution of the target in 6×SSPE was carried out. During hybridization, the external surface of the array was kept in contact with a thermoelectric cooler set at 15° C. Hybridization was carried out for 20 minutes while driving the crystal at 2 MHZ at an average power of 4 W (on time=0.2 sec., off time=0.8 sec.). The resulting average intensity was identical to that achieved using mechanical mixing of the chamber (vertical rotation with an incorporated bubble).

Additional experiments using fluorescently labeled and fragmented 1 kb portion of the HIV virus had a successful base calling rates. In particular, a 1 kb HIV nucleic acid segment was sequenced using an HIV tiled oligonucleotide array or chip. See, U.S. patent application Ser. No. 08/284,064, filed Aug. 2, 1994, now abandoned, and incorporated herein by reference for all purposes. Acoustic mixing achieved a 90.5% correct base calling rate as compared to a 95.8% correct base calling rate for mechanical mixing.

Example 6

Demonstration of Fluid Direction System

A polycarbonate cartridge was fabricated using conventional machining, forming an array of valves linking a common channel to a series of channels leading to a series of 10 μl chambers, each of which was terminated in a hydrophobic vent. The chambers included (1) an inlet chamber #1, (2) inlet chamber #2, (3) reaction chamber, (4) debubbling chamber having a hydrophobic vent in the center, (5) a measuring chamber and (6) a storage chamber. Elastomeric valves were opened and closed by application of vacuum or pressure (approx. 60 psi) to the space above the individual valves.

In a first experiment, water containing blue dye (food coloring) was introduced into inlet chamber #1 while water containing yellow dye (food coloring) was introduced into inlet chamber #2. By opening the appropriate valves and applying 5 psi to the appropriate vent, the following series of fluid movements were carried out: the blue water was moved from inlet chamber #1 to the reaction chamber; the yellow water was moved from inlet chamber #2 to the storage chamber #6; the blue water was moved from the reaction chamber to the measuring chamber and the remaining blue water was exhausted to the inlet chamber #1; The measured blue water (approximately 1.6 μl) was moved from the measuring chamber to the debubbling chamber; the yellow water is then moved from the storage chamber into the debubbling chamber whereupon it linked with the blue water and appeared to mix, producing a green color; and finally, the mixture was moved from the debubbling chamber to the reaction chamber and then to the storage chamber.

Functioning of the debubbling chamber was demonstrated by moving four separate plugs of colored water from the reaction chamber to the debubbling chamber. The discrete plugs, upon passing into the debubbling chamber, joined together as a single fluid plug.

The functioning of the measuring chamber was demonstrated by repetitively moving portions of a 10 μl colored water sample from the storage chamber to the measuring chamber, followed by exhausting this fluid from the measuring chamber. This fluid transfer was carried out 6 times, indicating repeated aliquoting of approximately 1.6 μl per measuring chamber volume (10 μl in 6 aliquots).

Example 7

Intergrated Sample-Preparation Demonstrations

1. SYS-01 PCR-through Hybridization

The following reactions were carried out under computer control: PCR[i], measurement, mixing, in-vitro transcription (IVT)[ii], fragmentation, target dilution, hybridization, and then washing. This system consisted of a modified target-preparation cartridge (model AFFX16) connected to the hybridization cartridge (model AFFX15) along with a pressurized vessel containing 6×SSPE. Temperature and fluid movement were controlled using a computer connected peltier devices, solenoid valves, and cartridge-based diaphragm valves and hydrophobic vents. First, the user injects the PCR mixture with template and the IVT reaction mixture into the cartridge. The PCR mix is thermally cycled in the reaction chamber while the IVT mixture is stored in an adjacent chamber held at 3° C. by a second peltier device. After the PCR is completed, part of the mixture is measured in a dosing chamber and the rest expelled. The measured PCR product is combined with the IVT mixture in the debubbling chamber where mixing takes place. This new mixture is transferred back to the reaction chamber where the IVT reaction is carried out at 37° C. generating fluorescently labeled RNA. After 1 hour the temperature is raised to 94° C. for 30 minutes to fragment the RNA. This fragmented product is injected into the hybridization cartridge through tubing addressed by a cartridge-based diaphragm valve. Next, 6× SSPE solution enters from a pressurized container, also controlled by a diaphragm valve, and mixes with the labeled RNA target. This liquid is moved into and out of the hybridization chamber for 1 hour. Afterwards, the target mixture is expelled to waste, and several volumes of 6× SSPE are injected into the hybridization chamber for washing. Finally, the cartridge is removed for scanning. In this system demonstration, the cumulative PCR and IVT yields were 16% and 40%, respectively, as compared to the control reactions. The GeneChip call rate was 94.4% correct, performance equivalent to that achieved using standard sample preparation.

2. SYS-02 Extraction through Fragmentation

The sequence consisting of DNA extraction, PCR, measurement, mixing, in-vitro transcription (IVT), and fragmentation was carried out. This system consists of a modified version of the DNA extraction cartridge described in a previous section, where one of the chambers has a wall made of borosilicate glass. Pressurized vessels containing 50:50 ethanol:water and 1×TBE were connected to diaphragm-valve controlled ports on the cartridge for washing and elution, respectively. As in the first system, all thermal control and fluid movement are all accomplished using a computer connected to peltier devices, solenoid valves, cartridge-based diaphragm valves and vents. First, the PCR and IVT mixtures are loaded into storage chambers and maintained at 3° C. Next, a lysate solution with a plasmid containing the HIV sequence (HXB2) in 0.1% BSA and 7 μg/μL hematin and 4M guanidine isothiocyanate is injected into the cartridge and loaded into the extraction chamber. After a 10 minute room-temperature extraction the lysate is automatically ejected to waste. Several volumes of a wash solution (1:1 ethanol; water) are automatically cycled through the extraction chamber and exhausted to waste. The 1× TBE is loaded into the chamber and elution carried out at 60° C. for 20 minutes. The eluted template is combined with the PCR mixture in the debubbling chamber, loaded into the reaction chamber and thermally cycled. A portion of the PCR product is combined with the IVT mixture in the debubbling chamber, and this new mixture is shuttled back to the reaction chamber. Incubation at 37° C. for 1 hour generates the labeled RNA target, and the temperature is raised to 94° C. for 30 minutes to fragment the RNA. Finally the target RNA was removed and hybridized manually using conventional methods. For this demonstration, the cumulative IVT yield was 49% as compared with the control, and subsequent hybridization of the fragmented target gave a call rate of 96.5%, equivalent to that achieved using standard methods.

3. SYS-03 PCR through Hybridization in One Cartridge

A cartridge was designed that accommodates a GeneChip array (model AFFX-19) and a similar assay to SYS-01 was performed. The net PCR and IVT yields were 50% and 20%, respectively. The call rate on the HIV chip was 97.1% using the probability method.

4. SYS-04 Extraction through Hybridization

Th AFFX-19 cartridge was modified to include a glass-walled extraction chamber. All reactions and processes were carried out: extraction, PCR, in vitro transcription, fragmentation, sample dilution, hybridization, and washing. A simulated blood lysate spiked with HXB2 plasmid, similar to SYS-02 was used as the sample, The net PCR and IVT yields were each approximately 10%. The call rate on the HIV chip was 94.4%.

Example 8

Reaction Demonstrations

1. RXN-01 PCR

PCR was performed in ultrasonically welded polycarbonate and polypropylene cartridges. The 10 $\mu$L reaction chambers were pretreated with a PCR solution for 30 minutes at room temperature. All reaction yields were equivalent to the control.

2. RXN-02 Reverse Transcription

The reverse transcription reaction was demonstrated in polycarbonate cartridges. The reaction mix was treated as follows: first 10.5 $\mu$L water, 3 $\mu$L mRNA (polyA+2.3 kB, Gibco), and 3 $\mu$L primer (T7, 100 pM/$\mu$L) were mixed and denatured at 70° C. for 10 minutes. This mixture was quenched, and the following were added with the indicated final concentrations: DTT 10 mM, dNTP's 0.5 mM, and Gibco Superscript buffer 1×. After incubation for 2 minutes reverse transcriptase added to a concentration of 4 units/$\mu$L. This mixture was injected into 10 $\mu$L polycarbonate reaction chambers and incubated at 37° C. for 1 hr. The reaction yields were identical to the control.

I PCR reaction mixture consists of 40 pg/$\mu$L of 1.1 kB template DNA, 0.3 units of TAQ polymerase, 1.5 mM $MgCl_2$, 0.2 mM dNTP's, 0.2 uM primers, and 1× Perkin Elmer PCR buffer. Thermal program includes: (1) an initial denature at 94° C. for 60 seconds, (2) a denature at 94° C. for 20 seconds, (3) an anneal at 65° C. for 40 seconds, (4) an extend at 72° C. for 50 seconds, (5) steps 2 through 4 repeated 35 times total, (6) a final extend at 72° C. for 60 seconds.

ii IVT reaction mixture consists of 2.5 mM each of ATP, CTP, GTP, and 0.5 mM UTP, 0.25 mM Fluomscein-UTP, 8 mM $MgCl_2$, 50 mM HEPES, IX Promega Transcription Buffer, 10 mM DTT, 1 unit T3 RNA polymerase, 0.5 units RNAguard (Pharmacia). Thermal program consists of 37° C. for 60 minutes.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A nucleic acid extraction device, comprising:

a body having at least one chamber with at least one inlet channel;

a porous flow-through deformable plug disposed within the chamber, the deformable plug having nucleic acid binding properties; and a flexible diaphragm for compressing said plug thereby removing trapped liquids.

2. The nucleic acid extraction device of claim 1, wherein the flexible diaphragm is disposed between a pneumatic port and the deformable plug, the device further comprising a pressure system for displacing the flexible diaphragm to draw a sample through the inlet channel into the chamber.

3. A nucleic acid extraction device, comprising:

a body having at least one chamber with at least one inlet channel, wherein the chamber comprises a textured interior wall surface having nucleic acid binding properties;

a porous flow-through plug disposed within the chamber, the plug having nucleic acid binding properties, and a piezoelectric crystal adapted to acoustically agitate a nucleic acid sample, and wherein the piezoelectric crystal is mounted to the chamber opposite the textured interior wall surface of the chamber.

4. A biological sample refinement device, comprising:

a body having at least one microchamber with at least one inlet channel;

a structure disposed within the microchamber, the structure having binding sites thereon; and a fluid distribution system for delivering a biological sample into the microchamber such that at least a portion of the sample contacts the binding sites, the fluid distribution system being adapted to deliver an adjustable volume of metered elution buffer into the microchamber.

5. The device of claim 4, wherein the structure comprises a substantially planar wall with a plurality of beads attached thereto.

6. The device of claim 4, wherein, the binding sites comprise agents selected from the group consisting of acids, bases, silanes, polylysine, tethered antibodies, nucleic acids and Poly-T DNA.

* * * * *